(12) United States Patent
Littman et al.

(10) Patent No.: US 9,505,798 B2
(45) Date of Patent: Nov. 29, 2016

(54) STEROID COMPOUNDS AS RORYT MODULATORS AND USES THEREOF

(75) Inventors: Dan R. Littman, New York, NY (US); Jun R. Huh, Newton, MA (US); Nicolas Gabriel Albert Manel, Paris (FR); Daniel A. Ryan, San Diego, CA (US); David Y. Gin, Pelham, NY (US); Mary S. Gin, legal representative, Pelham, NY (US); Michael R. Krout, Mifflinburg, PA (US)

(73) Assignees: New York University, New York, NY (US); Memorial Sloan-Kettering Cancer Center, New York, NY (US)

( * ) Notice: Subject to any disclaimer, the term of this patent is extended or adjusted under 35 U.S.C. 154(b) by 545 days.

(21) Appl. No.: 13/989,973

(22) PCT Filed: Nov. 28, 2011

(86) PCT No.: PCT/US2011/001936
§ 371 (c)(1),
(2), (4) Date: Sep. 12, 2014

(87) PCT Pub. No.: WO2012/074547
PCT Pub. Date: Jun. 7, 2012

(65) Prior Publication Data
US 2014/0066391 A1 Mar. 6, 2014

Related U.S. Application Data

(60) Provisional application No. 61/458,639, filed on Nov. 29, 2010.

(51) Int. Cl.
*C07J 17/00* (2006.01)
*A61K 31/704* (2006.01)
*C07J 19/00* (2006.01)

(52) U.S. Cl.
CPC ............ *C07J 17/005* (2013.01); *A61K 31/704* (2013.01); *C07J 19/005* (2013.01)

(58) Field of Classification Search
CPC .... A61K 31/704; C07J 17/005; C07J 19/005
USPC .......................................................... 514/26
See application file for complete search history.

(56) References Cited

U.S. PATENT DOCUMENTS

| 3,947,404 A | 3/1976 | Kaiser et al. | |
| 5,721,217 A * | 2/1998 | Liu | C07D 309/32 514/182 |
| 2006/0135443 A1* | 6/2006 | Khodadoust | A61K 31/56 514/26 |

FOREIGN PATENT DOCUMENTS

| WO | 2010068247 | 6/2010 | |
| WO | WO 2010/068247 A1 * | 6/2010 | ............. A01N 45/00 |

OTHER PUBLICATIONS

PubChem, 2007, pp. 1-10.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
The Merck Manual (16th Ed., 1999, pp. 339-342 and 1488-1490.*
Jin et al (Mol. Endocrinol., May 2010, 24(5), 923-929.*
Pubchem CID 16121811 (Jun. 19, 2007, pp. 1-10.*
Manunta et al., "Structure-activity relationships for the hypertensinogenic activity of Ouabain: Role of the sugar and lactone ring", Hypertension, 2001, 37, 472-477.
Jin et al., "Structural basis for hydroxycholesterols as natural ligands of orphan nuclear receptor ROR", Mol Endocrinol, 2010, 24, 923-929.
PubChem CID 16121811, 2007, http://pubchem.ncbi.nlm.nih.gov/summary/summary.cgi?cid=16121811&loc=ec_rcs.
Wang et al., "IL-17 can promote tumor growth through an IL-6-Stat3 signaling pathway", J. Exp. Med., 2009, 206:1457-1464.
Zhang et al., "The prevalence of Th17 cells in patients with gastric cancer", Biochemical and Biophysical Research Communications, 2008, 374:533-537.
Zhang et al., "Increased intratumoral IL-17-producing cells correlate with poor survival in hepatocellular carcinoma patients", Journal of Hepatology, 2009, 50:980-989.
Prabhala et al., "Elevated IL-17 produced by TH17 cells promotes myeloma cell growth and inhibits immune function in multiple myeloma", Blood, 2010, 115:5385-5392.
Kathania et al., "Itch inhibits IL-17-mediated colon inflammation and tumorigenesis by ROR-γt ubiquitination", Nature Immunology, Advance Online Publication, published online Jun. 20, 2016.
Wang et al., "ROR-γ drives androgen receptor expression and represents a therapeutic target in castration-resistant prostate cancer", Nature Medicine, Advance Online Publication, published online Mar. 28, 2016.
Kryczeck et al., "Cutting Edge: Th17 and Regulatory T Cell Dynamics and the Regulation by IL-2 in the Tumor Microenvironment", The Journal of Immunology, 2007, 178:6730-6733.

* cited by examiner

*Primary Examiner* — Ganapathy Krishnan
(74) *Attorney, Agent, or Firm* — Klauber & Jackson LLC

(57) ABSTRACT

Steroid compounds are disclosed that have a formula represented by the following:

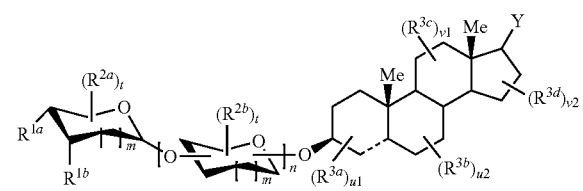

and wherein m, n, t, u1, u2, v1, v2, $R^{1a}$, $R^{1b}$, $R^{2a}$, $R^{2b}$, $R^{3a}$, $R^{3b}$, $R^{3c}$, $R^{3d}$, and Y are as described herein. The compounds may be prepared as pharmaceutical compositions, and may be used for the treatment or prevention of a variety of conditions in mammals including humans, including by way of non-limiting example, inflammatory conditions, autoimmune disorders, cancer, and graft-versus-host disease.

17 Claims, 12 Drawing Sheets

Digoxin

Wt(D) vs Wt(Dig)

20,22-Dihydrodigoxin-21,23-diol (Dig(dhd))

Digoxin-21-salicylidene (Dig(sal))

STEROID COMPOUNDS AS RORγT MODULATORS AND USES THEREOF

CROSS REFERENCE TO RELATED APPLICATIONS

The present application is a National Stage Application claiming the priority of PCT Application No. PCT/US2011/001936, filed Nov. 28, 2011, which in turn claims priority from U.S. Provisional Application No. 61/458,639, filed Nov. 29, 2010. Applicants claim the benefits of 35 U.S.C. §120 as to the PCT application and priority under 35 U.S.C. §119 as to the said U.S. Provisional application, and the entire disclosures of both applications are incorporated herein by reference.

The research leading to the present invention was funded in part by National Institutes of Health grants F32GM0860552, RO1GM058833, RO1GM067659, and RO1AI080885. The United States government has certain rights in the invention.

FIELD OF THE INVENTION

This invention relates to steroid compounds capable of modulating RORγt activity and uses of such compounds to treat diseases or conditions related to RORγt activity. More particularly, the compounds may be used to diminish inflammation associated with an inflammatory disease or condition or to reduce symptoms associated with an autoimmune disorder.

BACKGROUND OF THE INVENTION

The retinoic acid receptor-related orphan nuclear receptor (ROR) RORγ and its isoform RORγt (collectively "RORγ/γt") play a major role in regulation of a variety of biological systems. To illustrate, RORγt has a central role in immune system development, homeostasis, and responses to microbial pathogens. For example, RORγt is required for the differentiation of Th17 cells (Ivanov, I I et al. *Cell,* 2006, 126, 1121-33), a subset of T helper cells that protect the host from infection by secreting inflammatory cytokines such as IL-17 (also called IL-17A), IL-17F, IL-22, and TNFα. These cytokines are signaling proteins that have been shown to be essential in regulating numerous immune responses, including inflammatory responses to antigens. Th17 cells have also recently been shown to have important roles in activating and directing immune responses in a variety of autoimmune diseases, such as experimental autoimmune encephalomyelitis (EAE), collagen-induced arthritis (CIA), inflammatory bowel disease (IBD), cancer (Weaver, C. et al. *Ann. Rev. Immunol.,* 2007, 25, 821-52; Kryczek, I. et al. *J. Immunol.,* 2007, 178, 6730-3; Cua, D. J. et al. *Nature,* 2003, 421, 744-8; Langrish, C. L. et al. *J. Exp. Med.,* 2005, 201, 233-40; Yen, D. et al. *J. Clin. Invest.,* 2006, 116, 1310-6), and graft-versus-host disease (Carlson, M. J. et al. *Blood,* 28 Oct. 2008. [Epub ahead of print]; Kappel, L. W. et al. *Blood,* 17 Oct. 2008. [Epub ahead of print]). Th17 cells have also been implicated in asthma, psoriasis, rheumatoid arthritis, multiple sclerosis (Tzartos, J. S., et al. *Am. J. Pathology,* 2008, 172, 146-55; Yu, J. J., and Gaffen, S. L. *Front. Biosci.,* 2008, 13, 170-77; and Zheng, Y. et al. *Nature,* 2007, 445, 648-51), and Crohn's disease (Duerr, R. H., et al. *Science,* 2006, 314, 1461-63). Additionally, it has been shown that mice defective for expression of RORγt lack Th17 cells and are resistant to a variety of autoimmune diseases and that the absence of Th17-producing microbiota in the small intestine of mice alters the Th17: regulatory T (Treg) cell balance with implications for intestinal immunity, tolerance, and susceptibility to inflammatory bowel diseases (Ivanov, I. I. *Cell Host & Microbe,* 2008, 4, 337-49).

The formation of immune cell aggregates, such as cryptopatches (CP) and isolated lymphoid follicles (ILF), which contain RORγt expressing cells, is known to be a vital step in many immune responses. For example, CPs and ILFs are required for mucosal immunity and for production of the intestinal antibody IgA. Such immune responses can result in inflammation in various diseases, such as Crohn's disease. The ability to inhibit such immune responses by inhibiting the formation of immune cell aggregates may offer another way to treat diseases associated with such responses. In addition, recent studies have shown that IL-17 or IL-22 producing innate immune cells such as γδ T cells, NK cells, LTi cells, LTi-like cells play important roles during infectious and autoimmune diseases. Importantly, those cells also express RORγt (*Nature Reviews Immunology* 10, 479-489 (July 2010)).

T-cells have also been demonstrated to play a role in diseases characterized by bone loss and degradation, such as osteoarthritis. For example, in autoimmune arthritis, activation of T cells results in bone destruction mediated by osteoclasts. Th17, whose differentiation is regulated by RORγt, has been shown to be osteoclastogenic, thus linking T cell activation and bone resorption (Sato, K. et al. *J. Ex. Med.,* 2008, 203, 2673-82). Thus, the ability to regulate Th17 cell differentiation via RORγt modulation may offer a way to treat bone loss and degradation, such as that associated with autoimmune disease. Furthermore, interferon gamma (IFN-γ) suppresses osteoclast formation by rapidly degrading the RANK adaptor protein TRAF6 in the RANK-RANKL signaling pathway, and RORγt has been shown to down-regulate the production of IFN-γ (Ivanov, I. I. et al. *Cell,* 2006, 126, 1121-33). Thus, the ability to regulate osteoclast formation through modulation of RORγt-mediated osteoclast suppression may provide additional methods to treat bone loss and degradation, such as that associated with autoimmune disease (e.g., osteoarthritis).

Circadian rhythm relates to an approximately daily periodicity in the biochemical, physiological or behavioral processes of living beings, including plants, animals, fungi and some bacteria. Members of the ROR family of orphan nuclear receptors have been implicated in regulation of control of circadian clock function by regulation of clock genes (Ueda, H. R. et al. *Nature,* 2002, 418, 534-39; Sato, T. K. et al. *Neuron,* 2004, 43, 527-37), and RORγ/γt has been implicated in the regulation of genes that govern circadian metabolism (Kumaki, Y. et al. *PNAS,* 2008, 105, 14946-51; Liu, C. et al. *Nature,* 2007, 447, 477-81). Moreover, RORγ gene expression is known to oscillate in a circadian manner in metabolically active tissues such as liver and brown adipose tissue (Yang, X. et al., *Cell,* 2006, 126, 801-10), which further confirms that a role exists for RORγ in regulating circadian function. Hence, the ability to modulate RORγ/γt expression may also result in circadian rhythm regulation and treatment of disorders associated with disruption of circadian rhythm. Since circadian rhythm is integral in maintaining metabolic levels, whose imbalance is linked to obesity and diabetes, modulators of RORγ/γt may also be useful in treating obesity and diabetes through regulation of circadian rhythm.

In view of the above, a need exists for therapeutic agents, and corresponding pharmaceutical compositions and related methods of treatment that address conditions causally related to RORγt activity, and it is toward the fulfillment and satisfaction of that need, that the present invention is directed.

The citation of references herein shall not be construed as an admission that such is prior art to the present invention.

SUMMARY OF THE INVENTION

The present invention provides a method for preventing, treating or ameliorating in a mammal a disease or condition that is causally related to RORγ or RORγt activity in vivo, which comprises administering to the mammal an effective disease-treating or condition-treating amount of a compound according to formula I:

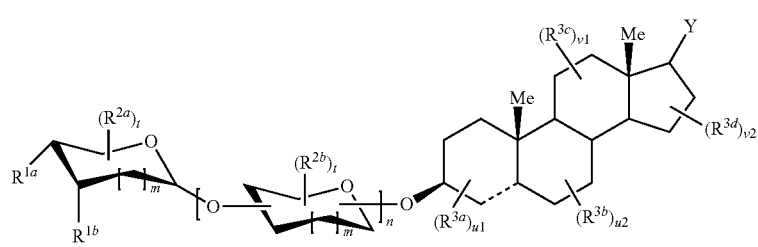

wherein
Y is $CO_2R^8$, $CH_2OH$,

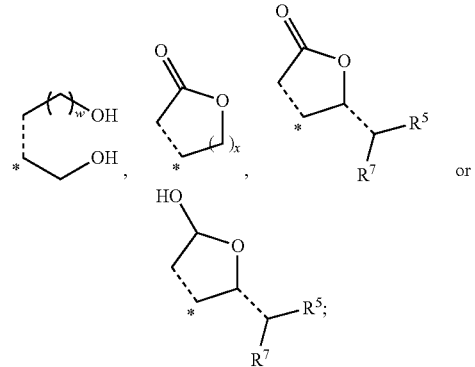

* denotes the attachment point; the subscript w is 0, 1, or 2;
the subscript x is 1, 2, or 3;
each $R^5$ and $R^7$ is independently H, substituted or unsubstituted alkyl, alkenyl, cycloalkyl, heterocycloalkyl, aryl, or heteroaryl;
$R^8$ is H or substituted or unsubstituted alkyl;
each $R^{1a}$ and $R^{1b}$ is independently OH, or O-acyl; or $R^{1a}$ and $R^{1b}$ together form

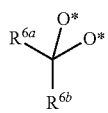

* denote the attachment points;
each $R^{6a}$ and $R^{6b}$ is independently H, substituted or unsubstituted alkyl, cycloalkyl, aryl or heteroaryl;

each $R^{2a}$ and $R^{2b}$ is independently OH, O-acyl, substituted or unsubstituted $C_1$-$C_6$ alkyl, substituted or unsubstituted $C_1$-$C_6$ alkoxy, or hydroxy $C_1$-$C_6$ alkyl;
each $R^{3a}$, $R^{3b}$, $R^{3c}$, and $R^{3d}$ is independently OH, $C_1$-$C_6$ alkyl, or O-acyl; or
any two $R^{3a}$, any two $R^{3b}$, any two $R^{3c}$, or any two $R^{3d}$ form =O;
each subscript m is independently 0 or 1; each subscript n is independently 0, 1, 2, 3, 4, or 5; each subscript t, u1, u2, v1 and v2 is independently 0, 1, 2, or 3; and
each dotted bond is independently a single or a double bond;
or a pharmaceutically acceptable salt, solvate or prodrug thereof;

and stereoisomers, isotopic variants and tautomers thereof.

In one embodiment, with respect to the compounds of formula I, the compound is according to formula III:

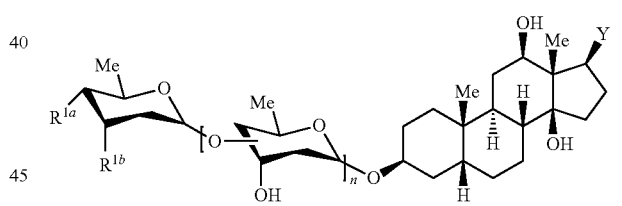

wherein
Y, n, $R^{1a}$ and $R^{1b}$ are as described for formula I;
or a pharmaceutically acceptable salt, solvate or prodrug thereof;
and stereoisomers, isotopic variants and tautomers thereof.

In one embodiment, with respect to the compounds of formula I, Y is

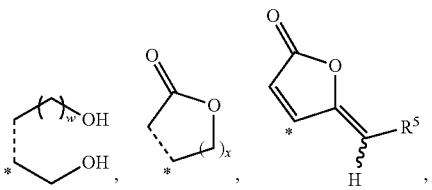

-continued

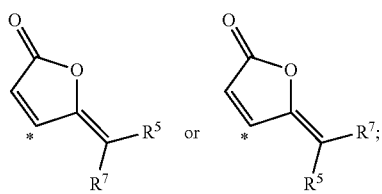

* denotes the attachment point; the subscript w is 0, 1, or 2;
the subscript x is 1, 2, or 3;
each $R^5$ and $R^7$ is independently H, substituted or unsubstituted alkyl, alkenyl, cycloalkyl, heterocycloalkyl, aryl, or heteroaryl.

In a further aspect, the present invention provides composition comprising a steroid compound of the invention. In a particular embodiment, the compound is according to formula VIa, VIb, VIc, or VId:

VIa
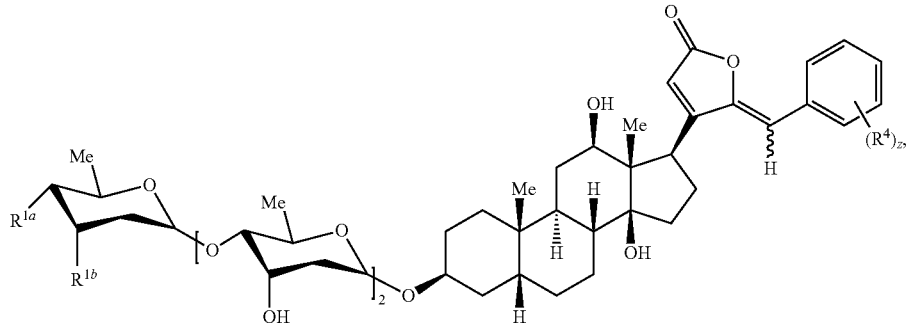

VIb
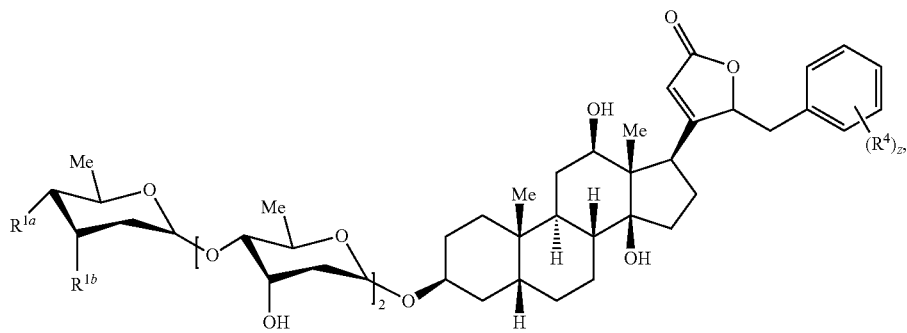

VIc
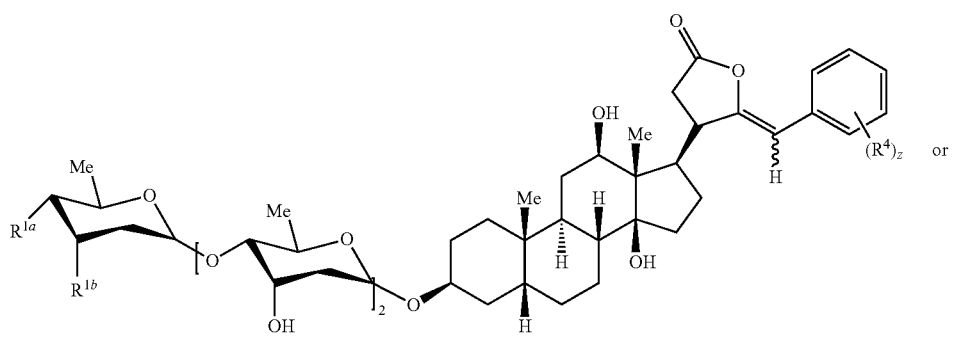

VId
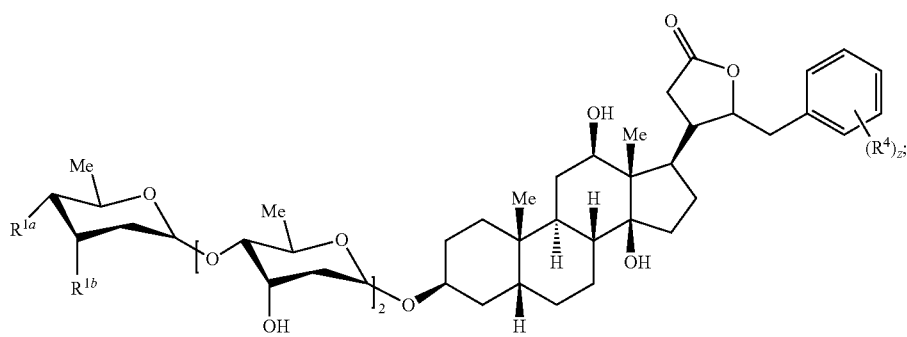

and $R^{1a}$ and $R^{1b}$ are as described for formula I; z is 1, 2, 3; and each $R^4$ is independently selected from substituted or unsubstituted alkyl, substituted or unsubstituted acyl, substituted or unsubstituted acylamino, substituted or unsubstituted alkylamino, substituted or unsubstituted $C_2$-$C_6$ alkoxy; substituted or unsubstituted alkylthio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted heterocycloalkyl, substituted or unsubstituted dialkylamino, iodo, hydroxyl, nitro, and thiol;

or a pharmaceutically acceptable salt, solvate or prodrug thereof;

and stereoisomers, isotopic variants and tautomers thereof.

In one particular embodiment, with respect to the compounds of formula VI, z is 1 or 2; and each $R^4$ is independently selected from iodo, alkyl, haloalkyl, $C_2$-$C_6$ alkoxy, haloalkoxy, hydroxyl, phenoxy, amino, nitro, benzyloxy, methylenedioxy, and substituted amino.

In one particular embodiment, with respect to the compounds of formula I, the compound is other than:

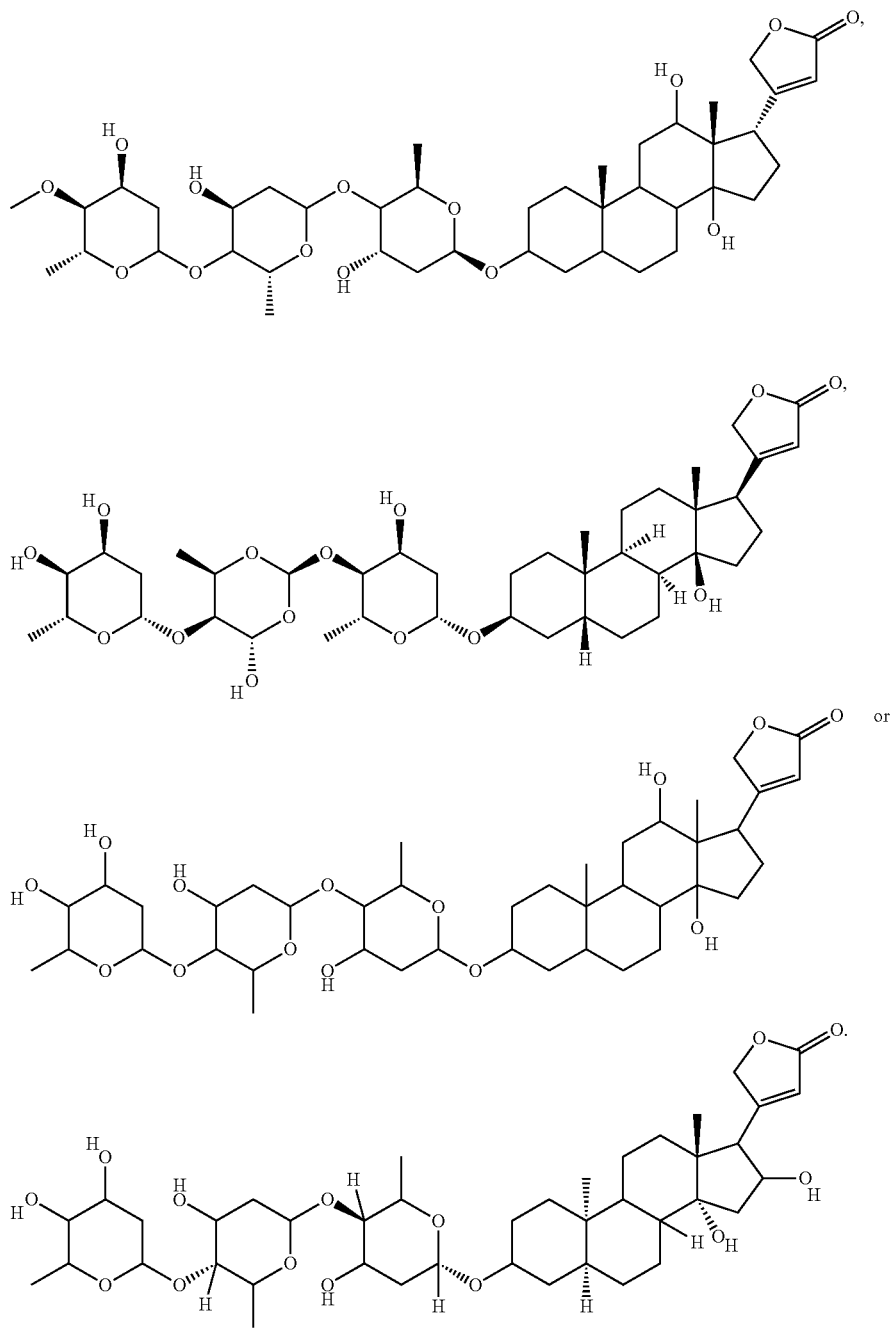

In a further aspect, the present invention provides pharmaceutical compositions comprising a steroid compound of the invention, and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

In a further aspect, this invention provides a method of treating a mammal susceptible to or afflicted with a condition from among those listed herein, and particularly, such condition as may be associated with RORγt. Such conditions include, without limitation, multiple sclerosis (and the animal model thereof, EAE), rheumatoid arthritis (and the animal model thereof, CIA), inflammatory bowel disease (IBD), cancer, graft-versus-host disease, asthma, psoriasis, diabetes, uveitis, bronchitis, allergic rhinitis, chronic obstructive pulmonary disease, atherosclerosis, and H. pylori infections and ulcers resulting from such infection.

Also encompassed is at least one compound described herein or a composition thereof for use in the treatment of an inflammatory and/or autoimmune disease or condition from among those listed herein, and particularly, such disease or condition as may be causally related to or associated with RORγt activity. Such conditions include, without limitation, multiple sclerosis (and the animal model thereof, EAE), rheumatoid arthritis (and the animal model thereof, CIA), inflammatory bowel disease (IBD), cancer, graft-versus-host disease, asthma, psoriasis, diabetes, uveitis, bronchitis, allergic rhinitis, chronic obstructive pulmonary disease, atherosclerosis, and H. pylori infections and ulcers resulting from such infection.

Other objects and advantages will become apparent to those skilled in the art from a consideration of the ensuing detailed description.

BRIEF DESCRIPTION OF THE DRAWINGS

FIG. 8 shows that digoxin treatment led to reduction of gut (large intestine) Th17 cells. Th17 cells were induced by Dextran Sulfate Sodium (DSS) treatment, a chemical agent that causes intestinal epithelial injury, and thus, is often used to generate an animal model that mimics many aspects of intestinal bowel diseases. B6 wild-type mice were IP injected with either DMSO or digoxin every day starting from day 1.2% DSS was added to drinking water on day 1. Gut associated mononuclear cells were collected and their cytokine expression was analyzed on day 7. Representative FACS plots (gated on $CD4^+CD3^+TCRβ^+CD19^-$ cells) from each group are shown (left). T cells isolated from large intestine of DMSO (n=3) or digoxin treated mice (n=3) were stained intracellularly for IFN-γ or IL-17a.

DETAILED DESCRIPTION OF THE INVENTION

Figure 1A:
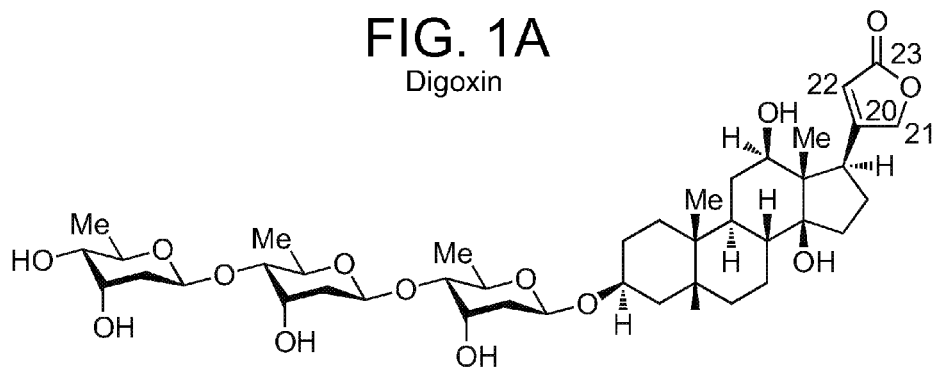
FIG. 1 shows that Digoxin binds to RORγ and inhibits its transcriptional activity. a, Chemical structure of digoxin. b, Digoxin demonstrates potent and dose-dependent inhibition of RORγ transcriptional activity in the Drosophila S2 cell luciferase reporter system. Ratio of firefly to Renilla luciferase activity is shown as relative luciferase unit (RLU) on the y-axis. c, Digoxin (10 μM) selectively inhibits RORγ dependent transcriptional activity without affecting that of closely related nuclear hormone receptors RORα (mouse homologue of RORγ) and DHR3 (Drosophila homologue of RORγ) and of the general transcriptional activator VP16. Percentages of relative luciferase units compared to DMSO-treated reporter cells are shown on the y-axis. d, In vitro competition assay. Recombinant human RORγ LBD was loaded with fluorescently-labeled 25-hydroxycholesterol in the presence of the indicated concentrations of digoxin, and fluorescence polarization was measured.

CD4+ T helper lymphocytes that express interleukin-17 (Th17 cells) have critical roles in mouse models of autoimmunity, and there is mounting evidence that they also influence inflammatory processes in humans. Genome-wide association studies in humans have linked genes involved in Th17 cell differentiation and function with susceptibility to Crohn's disease, rheumatoid arthritis, and psoriasis [Duerr et al. *Science* 314, 1461-1463 (2006); Nair et al. *Nat Genet* 41, 199-204 (2009); Stahl et al. *Nat Genet* 42, 508-514 (2010)]. Thus, the pathway towards differentiation of Th17 cells and, perhaps, of related innate lymphoid cells with similar effector functions [Buonocore et al. *Nature* 464, 1371-1375 (2010); Colonna *Immunity* 31, 15-23 (2009)], is an attractive target for therapeutic applications. Mouse and human Th17 cells are distinguished by expression of the retinoic acid receptor related orphan nuclear receptor RORγt, which is required for induction of IL-17 transcription and for the manifestation of Th17-dependent autoimmune disease in mice [Ivanov et al. *Cell* 126, 1121-1133 (2006)].

By performing a chemical screen with an insect cell-based reporter system, the present inventors identified the cardiac glycoside digoxin as a specific inhibitor of RORγt transcriptional activity. As described herein, digoxin inhibits murine Th17 cell differentiation without affecting differentiation of other T cell lineages and is effective in delaying the onset and reducing the severity of autoimmune disease in mice. At high concentrations, digoxin is toxic for human cells, but as shown herein, non-toxic synthetic derivatives, 20,22-dihydrodigoxin-21,23-diol (Dig(dhd)) and digoxin-2'-salicylidene (Dig(sal)), specifically inhibit induction of IL-17 in human CD4+ T cells. Using these small molecule compounds, the present inventors also demonstrate that RORγt is required for the maintenance of IL-17 expression in mouse and human effector T cells. These data demonstrate that derivatives of digoxin can be used as RORγt-targeted therapeutic agents that attenuate inflammatory lymphocyte function and autoimmune disease and as chemical probes for the development of additional RORγt-targeted therapeutic agents having similar functional properties.

DEFINITIONS

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. It should be further understood that the terms "groups" and "radicals" can be considered interchangeable when used herein.

"Acyl" refers to a radical —$C(O)R^{20}$, where $R^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a radical —$NR^{21}C(O)R^{22}$, where $R^{21}$ is hydrogen, alkyl, cycloalkyl, cycloheteroalkyl, aryl, arylalkyl, heteroalkyl, heteroaryl, heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)R$^{23}$ where R$^{23}$ is hydrogen, alkyl, aryl, cycloalkyl, cycloheteroalkyl, arylalkyl, heteroalkyl, heteroaryl, or heteroarylalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR$^{24}$ where R$^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NR$^{25}$C(O)OR$^{26}$, where R$^{25}$ is hydrogen, alkyl, aryl or cycloalkyl, and R$^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group R$^{27}$—C(O)—, where R$^{27}$ is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR$^{28}$R$^{29}$, wherein each of R$^{28}$ and R$^{29}$ are independently selected from hydrogen and alkyl.

"Arylamino" refers to the group aryl-NR$^{30}$R$^{31}$, wherein each of R$^{30}$ and R$^{31}$ are independently selected from hydrogen, aryl and heteroaryl.

"Alkoxyamino" refers to a radical —N(H)OR$^{32}$ where R$^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —NR$^{33}$R$^{34}$ where R$^{33}$ represents an alkyl or cycloalkyl group and R$^{34}$ is an aryl as defined herein.

"Alkylsulfonyl" refers to a radical —S(O)$_2$R$^{35}$ where R$^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R$^{35}$ where R$^{35}$ is an alkyl or cycloalkyl group as defined herein Representative examples include, but are not limited to, methylsulfinyl, ethylsulfinyl, propylsulfinyl, butylsulfinyl and the like.

"Alkylthio" refers to a radical —SR$^{35}$ where R$^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R$^{36}$)$_2$ where each R$^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R$^{36}$)$_2$ is an amino group.

"Aminocarbonyl" refers to the group —C(O)NR$^{37}$R$^{37}$ where each R$^{37}$ is independently hydrogen, alkyl, aryl and cycloalkyl, or where the R$^{37}$ groups are joined to form an alkylene group.

"Aminocarbonylamino" refers to the group —NR$^{38}$C(O)NR$^{38}$R$^{38}$ where each R$^{38}$ is independently hydrogen, alkyl, aryl or cycloalkyl, or where two R groups are joined to form an alkylene group.

"Aminocarbonyloxy" refers to the group —OC(O)NR$^{39}$R$^{39}$ where each R$^{39}$ is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —NHR$^{40}$ where R$^{40}$ represents an aryl group as defined herein.

"Aryloxycarbonyl" refers to a radical —C(O)—O-aryl where aryl is as defined herein.

"Arylsulfonyl" refers to a radical —S(O)$_2$R$^{41}$ where R$^{41}$ is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N(R$^{42}$)$_2$ where each R$^{42}$ group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarboriyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR$^{43}$ where R$^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{46}$, —O$^-$, =O, —OR$^{46}$, —SR$^{46}$, —S$^-$, =S, —NR$^{46}$R$^{47}$, =NR$^{46}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{46}$, —OS(O$_2$)O$^-$, —OS(O)$_2$R$^{46}$, —P(O)(O$^-$)$_2$, —P(O)(OR$^{46}$)(O$^{31}$), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O$^-$, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

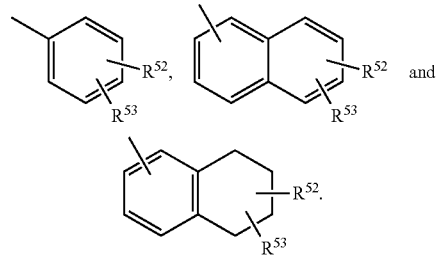

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^{55}$, NR$^{54}$SOR$^{55}$, NR$^{54}$SO$_2$R$^{57}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$alkyl, Saryl, SOaryl, SO$_2$aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

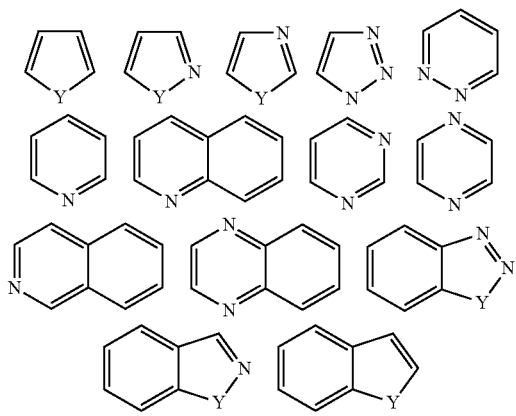

wherein each Y is selected from carbonyl, N, $NR^{58}$, O, and S; and $R^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

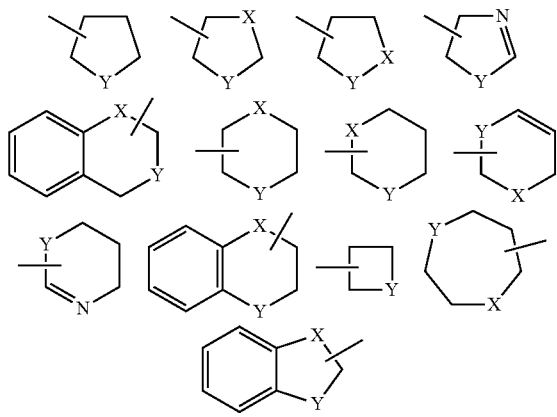

wherein each X is selected from $CR^{58}{}_2$, $NR^{58}$, O and S; and each Y is selected from $NR^{58}$, O and S; and $R^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—. Substituting groups include carbonyl or thiocarbonyl which provide, for example, lactam and urea derivatives.

Examples of representative cycloheteroalkenyls include the following:

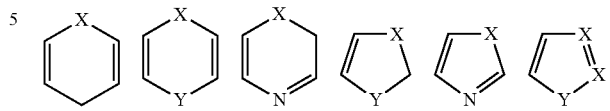

wherein each X is selected from $CR^{58}{}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

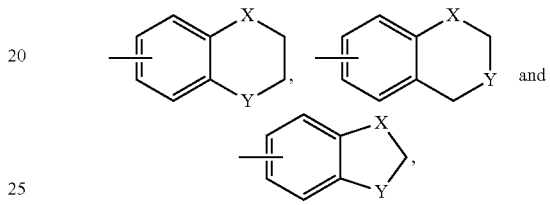

wherein each X is selected from C—$R^{58}{}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an $R^4$ in a $R^{4c}$ group present as substituents directly on A, B, W, Y or Z of the compounds of this invention or may be present as a substituent in the "substituted" aryl and aliphatic groups present in the compounds.

Examples of hetero substituents include:
- halo,
- $-NO_2$, $-NH_2$, $-NHR^{59}$, $-N(R^{59})_2$,
- $-NRCOR$, $-NR^{59}SOR^{59}$, $-NR^{59}SO_2R^{59}$, OH, CN,
- $-CO_2H$,
- $-R^{59}-OH$, $-O-R^{59}$, $-COOR^{59}$,
- $-CON(R^{59})_2$, $-CONROR^{59}$,
- $-SO_3H$, $-R^{59}-S$, $-SO_2N(R^{59})_2$,
- $-S(O)R^{59}$, $-S(O)_2R^{59}$ wherein each $R^{59}$ is independently an aryl or aliphatic, optionally with substitution. Among hetero substituents containing $R^{59}$ groups, preference is given to those materials having aryl and alkyl $R^{59}$ groups as defined herein. Preferred hetero substituents are those listed above.

"Hydrogen bond donor" group refers to a group containing O—H, or N—H functionality. Examples of "hydrogen bond donor" groups include —OH, $-NH_2$, and —NH—$R^{59a}$ and wherein $R^{59a}$ is alkyl, cycloalkyl, aryl, or heteroaryl.

"Dihydroxyphosphoryl" refers to the radical —$PO(OH)_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)$NH_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —$SR^{60}$ where $R^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as $R^{61}$—(O$_2$)S— wherein $R^{61}$ is any substituent described herein. "Aminosulfonyl" or "Sulfonamide" refers to the radical H$_2$N(O$_2$)S—, and "substituted aminosulfonyl" "substituted sulfonamide" refers to a radical such as $R^{62}{}_2$N(O$_2$)S— wherein each $R^{62}$ is independently any substituent described herein.

"Sulfone" refers to the group —SO$_2$$R^{63}$. In particular embodiments, $R^{63}$ is selected from H, lower alkyl, alkyl, aryl and heteroaryl.

"Thioaryloxy" refers to the group —$SR^{64}$ where $R^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both.

"Preventing" or "prevention" refers to a reduction in risk of acquiring a disease or disorder.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

The present invention provides a method for preventing, treating or ameliorating in a mammal a disease or condition that is causally related to the activity of the RORγ or RORγt in vivo, which comprises administering to the mammal an effective disease-treating or condition-treating amount of a compound according to formula I:

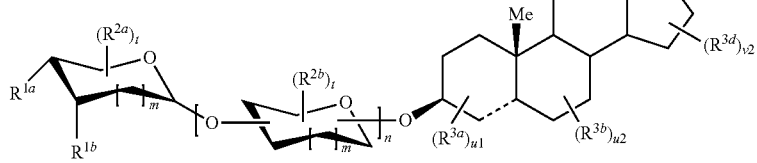

wherein
Y is $CO_2R^8$, $CH_2OH$,

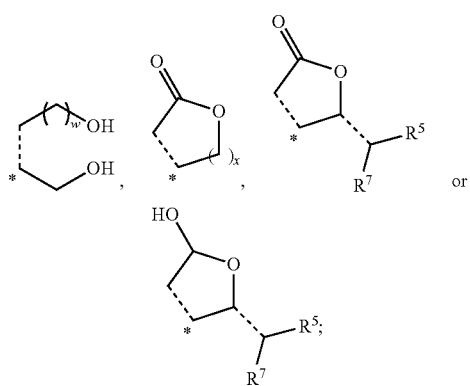

* denotes the attachment point; the subscript w is 0, 1, or 2;

the subscript x is 1, 2, or 3;

each $R^5$ and $R^7$ is independently H, substituted or unsubstituted alkyl, alkenyl, cycloalkyl, heterocycloalkyl, aryl, or heteroaryl;

$R^8$ is H or substituted or unsubstituted alkyl;

each $R^{1a}$ and $R^{1b}$ is independently OH, or O-acyl; or $R^{1a}$ and $R^{1b}$ together form

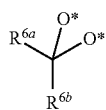

* denote the attachment points;

each $R^{6a}$ and $R^{6b}$ is independently H, substituted or unsubstituted alkyl, cycloalkyl, aryl or heteroaryl;

each $R^{2a}$ and $R^{2b}$ is independently OH, O-acyl, substituted or unsubstituted $C_1$-$C_6$ alkyl, substituted or unsubstituted $C_1$-$C_6$ alkoxy, or hydroxy $C_1$-$C_6$ alkyl;

each $R^{3a}$, $R^{3b}$, $R^{3c}$, and $R^{3d}$ is independently OH, $C_1$-$C_6$ alkyl, or O-acyl; or any two $R^{3a}$, any two $R^{3b}$, any two $R^{3c}$, or any two $R^{3d}$ form =O;

each subscript m is independently 0 or 1; each subscript n is independently 0, 1, 2, 3, 4, or 5; each subscript t, u1, u2, v1 and v2 is independently 0, 1, 2, or 3; and each dotted bond is independently a single or a double bond;

or a pharmaceutically acceptable salt, solvate or prodrug thereof;

and stereoisomers, isotopic variants and tautomers thereof.

In one embodiment, with respect to the compounds of formula I, n is 1 or 2.

In one embodiment, with respect to the compounds of formula I, each m is 0.

In one embodiment, with respect to the compounds of formula I, each m is 1.

In one embodiment, with respect to the compounds of formula I, each t is 2.

In one embodiment, with respect to the compounds of formula I, the Me at $R^{18}$ or Me at $R^{19}$ is replaced independently with H, $CH_2OH$ or CHO.

In one embodiment, with respect to the compounds of formula I, each $R^{2a}$ is independently Me, OH, hydroxy $C_1$-$C_6$ alkyl, or O-(hydroxy $C_2$-$C_6$ alkyl).

In another embodiment, with respect to the compounds of formula I, each $R^{2a}$ is independently Me, OH, or hydroxymethyl.

In one embodiment, with respect to the compounds of formula I, the subscript t is 1; and each $R^{2a}$ is Me, OH, O-(hydroxyethyl), O-(hydroxypropyl), or hydroxymethyl.

In one embodiment, with respect to the compounds of formula I, each $R^{2b}$ is independently Me, OH, hydroxy $C_1$-$C_6$ alkyl, or O-(hydroxy $C_2$-$C_6$ alkyl).

In one embodiment, with respect to the compounds of formula I, the subscript t is 2; and each $R^{2b}$ is independently Me, OH, or hydroxymethyl.

In one embodiment, with respect to the compounds of formula I, the subscript t is 1; and each $R^{2a}$ is Me, OH, or hydroxymethyl.

In one embodiment, with respect to the compounds of formula I, each $R^{2b}$ is Me, OH, or hydroxymethyl.

In one embodiment, with respect to the compounds of formula I, the subscript t is 2; and each $R^{2b}$ is Me, OH, or hydroxymethyl.

In one embodiment, with respect to the compounds of formula I, the subscript u1 is 0.

In one embodiment, with respect to the compounds of formula I, the subscript u1 is 1; and $R^{3a}$ is OH or Me.

In one embodiment, with respect to the compounds of formula I, the subscript u2 is 0.

In one embodiment, with respect to the compounds of formula I, the subscript u2 is 1; and $R^{3b}$ is OH or Me.

In one embodiment, with respect to the compounds of formula I, the subscript v1 is 0.

In one embodiment, with respect to the compounds of formula I, the subscript v1 is 1; and $R^{3c}$ is OH or Me.

In one embodiment, with respect to the compounds of formula I, the subscript v2 is 0.

In one embodiment, with respect to the compounds of formula I, the subscript v2 is 1; and $R^{3d}$ is OH or Me.

In one embodiment, with respect to the compounds of formula I, the compound is according to formula II:

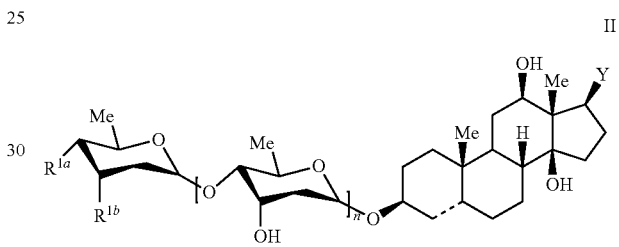

wherein

Y, n, $R^{1a}$ and $R^{1b}$ are as described for formula I; and the dotted bond is a single or a double bond;

or a pharmaceutically acceptable salt, solvate or prodrug thereof;

and stereoisomers, isotopic variants and tautomers thereof.

In one embodiment, with respect to the compounds of formula I-II, the dotted bond in the steroid nucleus is a single bond.

In one embodiment, with respect to the compounds of formula I, the compound is according to formula III:

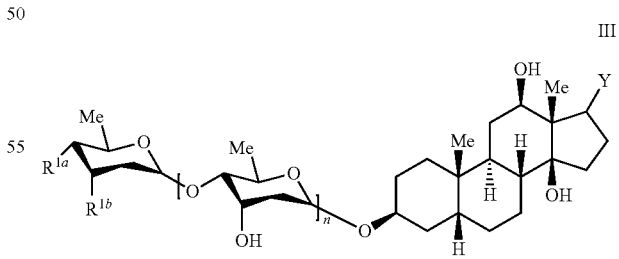

wherein

Y, n, $R^{1a}$ and $R^{1b}$ are as described for formula I;

or a pharmaceutically acceptable salt, solvate or prodrug thereof;

and stereoisomers, isotopic variants and tautomers thereof.

In one embodiment, with respect to the compounds of formula I-III, each $R^5$ and $R^7$ is H.

In one embodiment, with respect to the compounds of formula I-III, each $R^5$ and $R^7$ is independently substituted or unsubstituted alkyl, alkenyl, cycloalkyl, heterocycloalkyl, aryl, or heteroaryl. In one embodiment, each $R^5$ and $R^7$ is substituted or unsubstituted alkyl. In another embodiment, each $R^5$ and $R^7$ is substituted or unsubstituted aryl.

In one embodiment, with respect to the compounds of formula I-III, one of $R^5$ and $R^7$ is H and the other is substituted or unsubstituted alkyl, alkenyl, cycloalkyl, heterocycloalkyl, aryl, or heteroaryl.

In one embodiment, with respect to the compounds of formula I-III, Y is $CO_2H$. In another embodiment, Y is $CO_2R^8$, and $R^8$ is alkyl. In one embodiment, $R^8$ is Me, Et, n-Pr, i-Pr, n-Bu, i-Bu, or t-Bu.

In one particular embodiment Y is $CO_2Me$, or $CO_2Et$.

In one embodiment, with respect to the compounds of formula I-III, Y is $CH_2OH$.

In one embodiment, with respect to the compounds of formula I-III, Y is

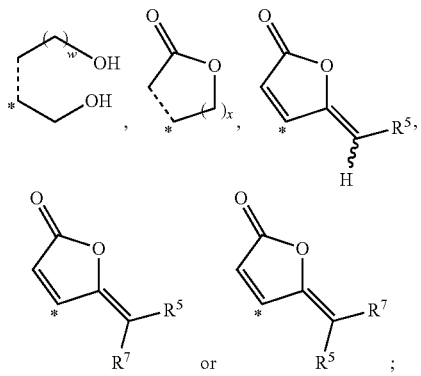

* denotes the attachment point; the subscript w is 0, 1, or 2;
the subscript x is 1, 2, or 3;
each $R^5$ and $R^7$ is independently H, substituted or unsubstituted alkyl, alkenyl, cycloalkyl, heterocycloalkyl, aryl, or heteroaryl.

In one embodiment, with respect to the compounds of formula I-III, Y is

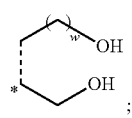

* denotes the attachment point; and the subscript w is 0, 1, or 2.

In one embodiment, with respect to the compounds of formula I-III, Y is

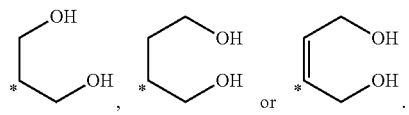

In one embodiment, with respect to the compounds of formula I-III, Y is

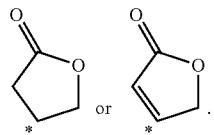

In one embodiment, with respect to the compounds of formula I-III, Y is

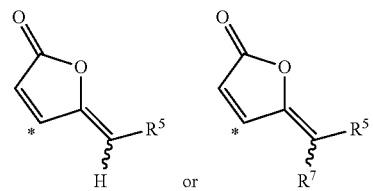

and $R^5$ and $R^7$ are as described for formula I.

In one embodiment, with respect to the compounds of formula I-III, Y is

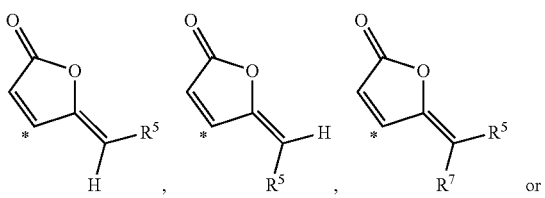

and $R^5$ and $R^7$ are as described for formula I.

In one embodiment, with respect to the compounds of formula I-III, Y is

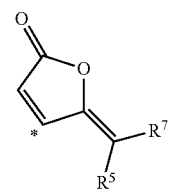

and $R^5$ and $R^7$ are as described for formula I.

In one embodiment, with respect to the compounds of formula I-III, Y is

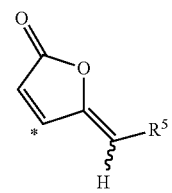

and $R^5$ is substituted or unsubstituted alkyl, substituted or unsubstituted alkenyl, substituted or unsubstituted aryl, substituted or unsubstituted heteroaryl, or substituted or unsubstituted cycloalkyl.

In one embodiment, with respect to the compounds of formula I-III, Y is

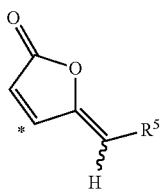

and R⁵ is alkyl, unsubstituted, or substituted with halo, phenyl, hydroxyl or methoxy;
alkenyl, unsubstituted, or substituted with alkyl, or phenyl;
cycloalkyl, unsubstituted, or substituted with hydroxyl or methoxy; or
aryl, unsubstituted, or substituted with substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted heterocycloalkyl, substituted or unsubstituted dialkylamino, halo, nitro, and thiol.

In one embodiment, with respect to the compounds of formula I-III, Y is

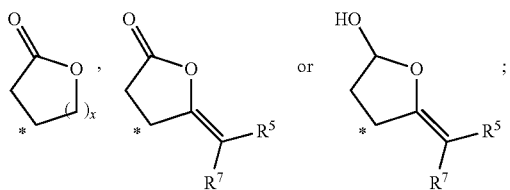

wherein * denotes the attachment point;
and the subscript x is 1, 2, or 3; and R⁵ and R⁷ are as described for formula I.

In one embodiment, with respect to the compounds of formula I-III, Y is as described above and R⁵ is alkyl, unsubstituted, or substituted with halo, phenyl, hydroxyl or methoxy, alkenyl, unsubstituted, or substituted with alkyl, or phenyl; cycloalkyl, unsubstituted, or substituted with hydroxyl or methoxy; or aryl, unsubstituted, or substituted with substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted heterocycloalkyl, substituted or unsubstituted dialkylamino, halo, nitro, and thiol.

In one embodiment, with respect to the compounds of formula I-III, Y is as described above and R⁷ is H.

In one embodiment, with respect to the compounds of formula I, the compound is according to formula IVa or IVb:

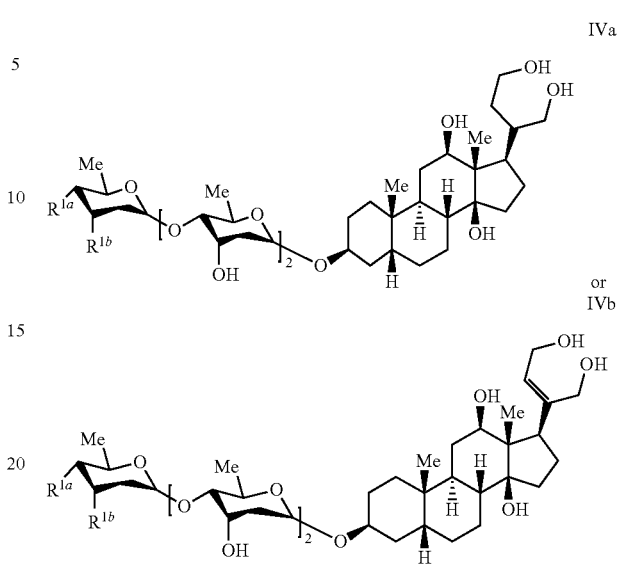

wherein
R$^{1a}$ and R$^{1b}$ are as described for formula I;
or a pharmaceutically acceptable salt, solvate or prodrug thereof;
and stereoisomers, isotopic variants and tautomers thereof.

In one embodiment, with respect to the compounds of formula I, the compound is according to formula Va or Vb:

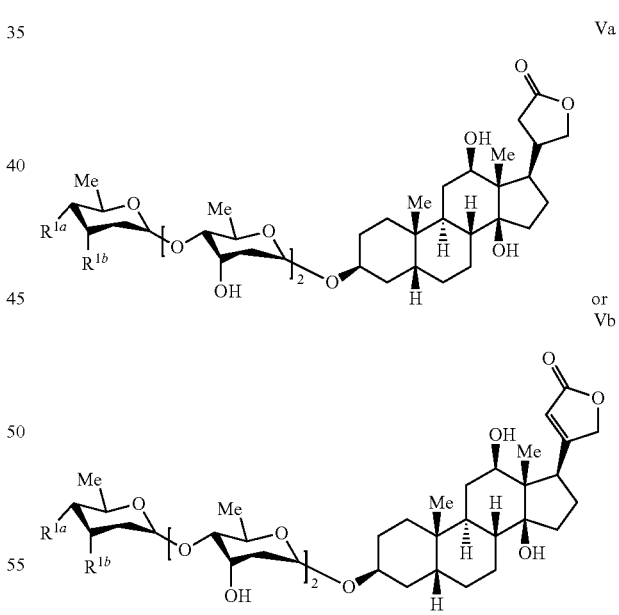

wherein
R$^{1a}$ and R$^{1b}$ are as described for formula I;
or a pharmaceutically acceptable salt, solvate or prodrug thereof;
and stereoisomers, isotopic variants and tautomers thereof.

In one embodiment, with respect to the compounds of formula I, the compound is according to formula VIa, VIb, VIc, or VId:

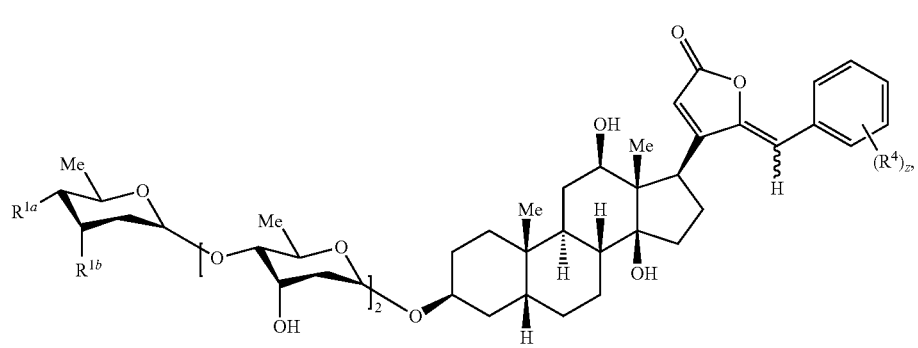

VIa

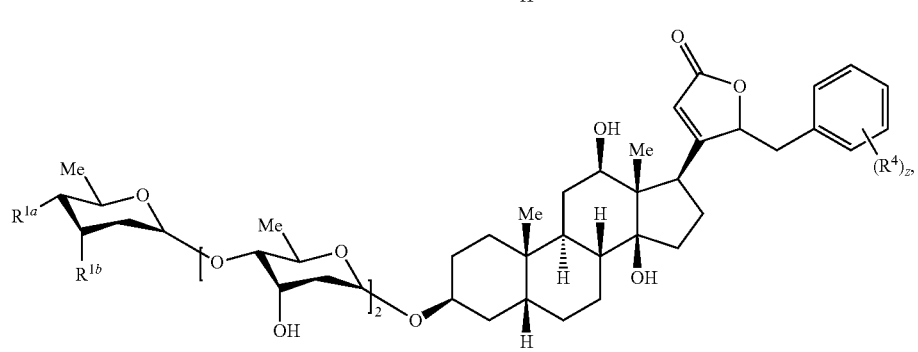

VIb

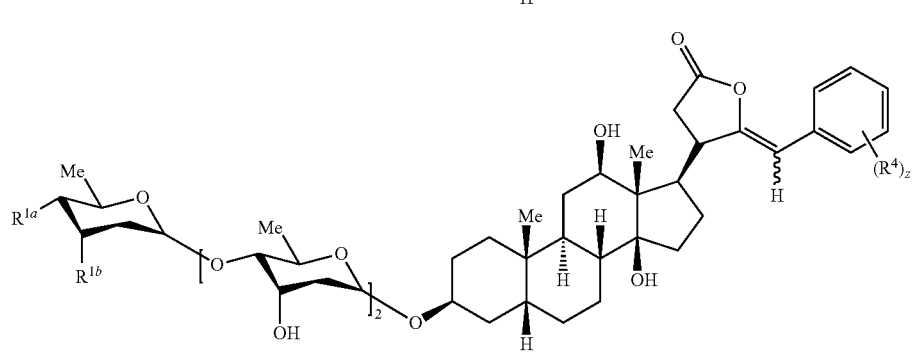

VIc or

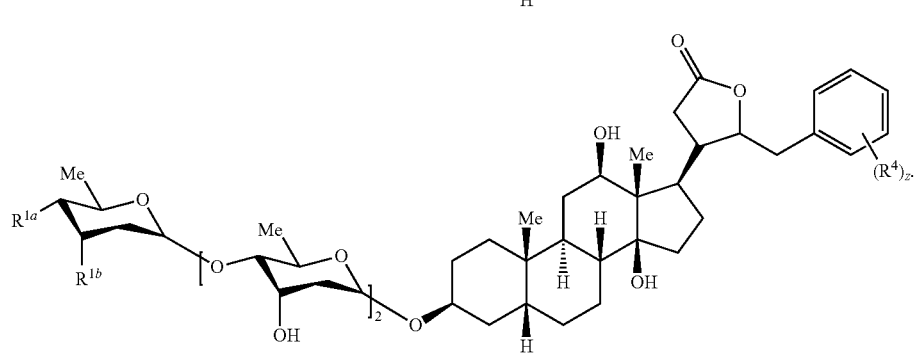

VId wherein
$R^{1a}$ and $R^{1b}$ are as described for formula I; z is 0, 1, 2, 3, 4, or 5; and each $R^4$ is independently selected from substituted or unsubstituted alkyl, substituted or unsubstituted acyl, substituted or unsubstituted acylamino, substituted or unsubstituted alkylamino, substituted or unsubstituted alkylthio, substituted or unsubstituted alkoxy; substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted heterocycloalkyl, substituted or unsubstituted dialkylamino, halo, nitro, hydroxyl, and thiol;

or a pharmaceutically acceptable salt, solvate or prodrug thereof;

and stereoisomers, isotopic variants and tautomers thereof.

In one embodiment, with respect to the compounds of formula VIa-VId, z is 0.

In one embodiment, with respect to the compounds of formula VIa-VId, z is 1, 2, or 3.

In one embodiment, with respect to the compounds of formula VIa-VId, each $R^4$ is independently selected from halo, alkyl, haloalkyl, alkoxy, haloalkoxy, hydroxyl, phenoxy, amino, nitro, benzyloxy, methylenedioxy, and substituted amino.

In one embodiment, with respect to the compounds of formula VIa-VId, each $R^4$ is independently selected from OH, OMe, $CF_3$, $OCF_3$, $CF_3$, $NMe_2$, OEt, $NO_2$, Cl, F, OPh, and SMe.

In one embodiment, with respect to the compounds of formula VIa-VId, each $R^4$ is independently selected from iodo, alkyl, haloalkyl, $C_2$-$C_6$alkoxy, haloalkoxy, hydroxyl, phenoxy, amino, nitro, benzyloxy, and substituted amino.

In one particular embodiment, with respect to the compounds of formula VIa-VId, z is 1 or 2; and each $R^4$ is independently selected from iodo, alkyl, haloalkyl, $C_2$-$C_6$ alkoxy, haloalkoxy, hydroxyl, phenoxy, amino, nitro, benzyloxy, methylenedioxy, and substituted amino.

In one particular embodiment, with respect to the compounds of formula VIa-VId, z is 1 or 2; and each $R^4$ is independently selected from I, Me, OH, OEt, $CF_3$, $OCF_3$, $CF_3$, $NMe_2$, $NO_2$, OPh, and SMe.

In one embodiment, with respect to the compounds of formula I-VId, each $R^{1a}$ and $R^{1b}$ is OH.

In one embodiment, with respect to the compounds of formula I-VId, each $R^{1a}$ and $R^{1b}$ is independently OH or OAc.

In one embodiment, with respect to the compounds of formula I-VId, $R^{1a}$ and $R^{1b}$ together form

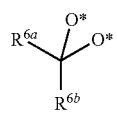

* denote the attachment points;

each $R^{6a}$ and $R^{6b}$ is independently H, substituted or unsubstituted alkyl, cycloalkyl, aryl or heteroaryl.

In one embodiment, with respect to the compounds of formula I-VI, $R^{1a}$ and $R^{1b}$ together form

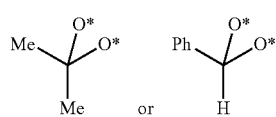

* denote the attachment points;

In one embodiment, with respect to the compounds of formula I, the compound is according to formula VIIa, VIIb, or VIIc:

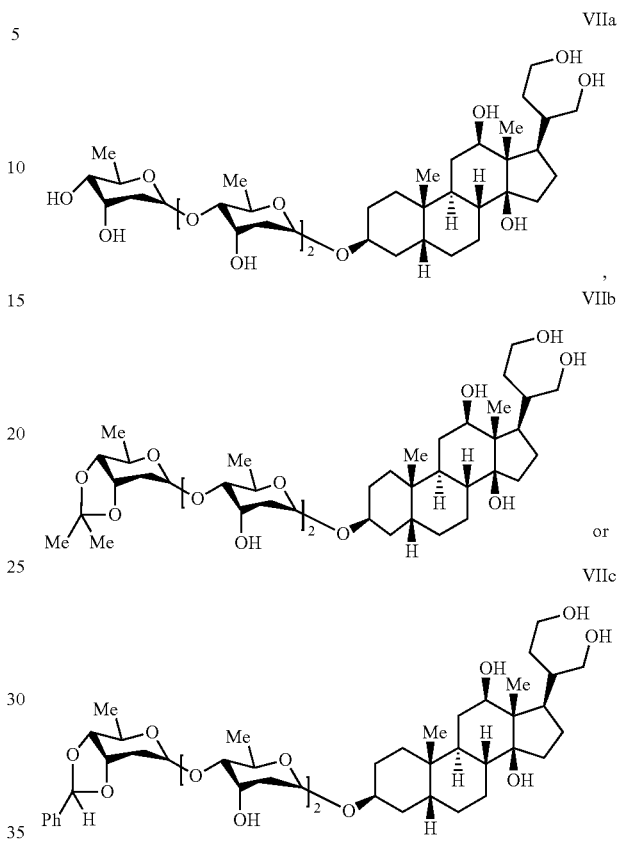

or a pharmaceutically acceptable salt, solvate or prodrug thereof;
and stereoisomers, isotopic variants and tautomers thereof.

In one embodiment, with respect to the compounds of formula I, the compound is according to formula VIIIa, VIIIb, or VIIIc:

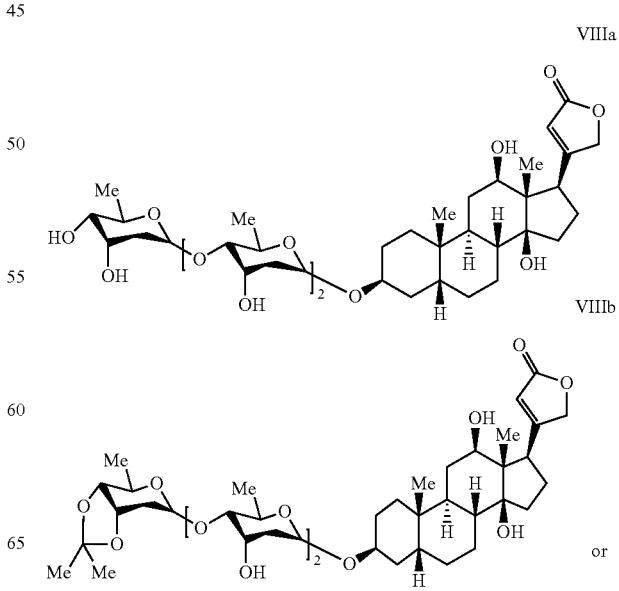

or

-continued
VIIIc
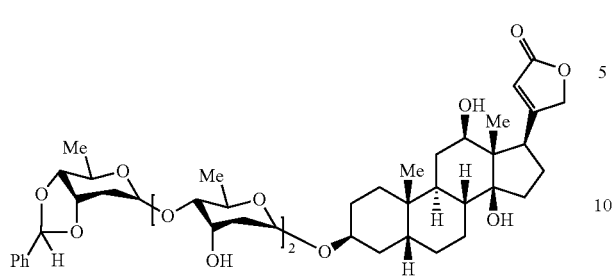
or a pharmaceutically acceptable salt, solvate or prodrug thereof;
and stereoisomers, isotopic variants and tautomers thereof.
In one embodiment, with respect to the compounds of formula I, the compound is according to formula IXa, IXb, or IXc:
IXa
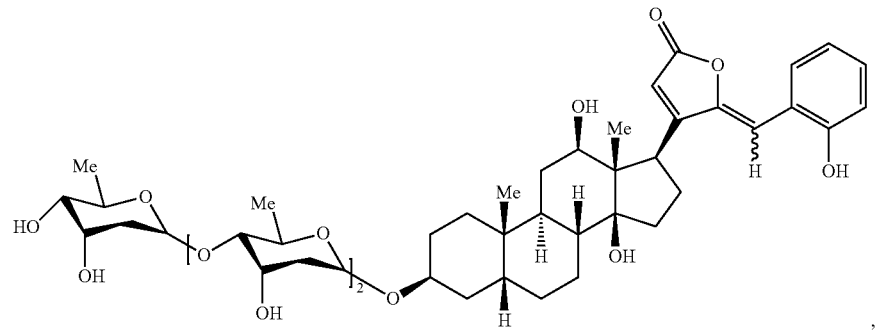
,
IXb
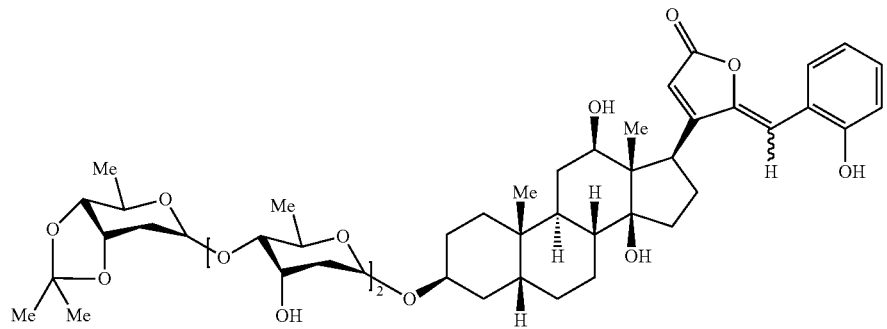
or
IXc
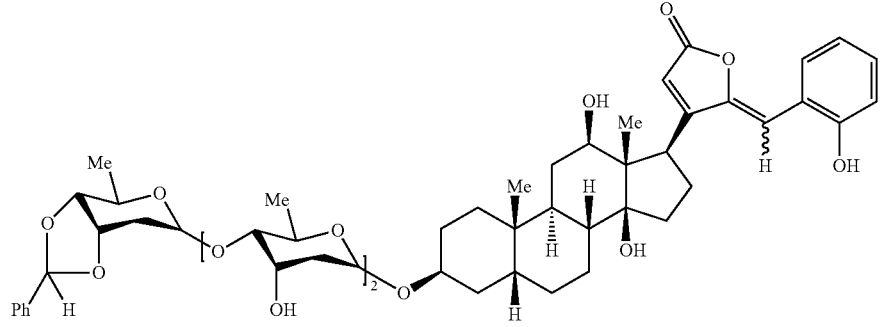

or a pharmaceutically acceptable salt, solvate or prodrug thereof;
and stereoisomers, isotopic variants and tautomers thereof.
In one embodiment, with respect to the compounds of formula I, the compound is according to formula Xa, Xb, or Xc:
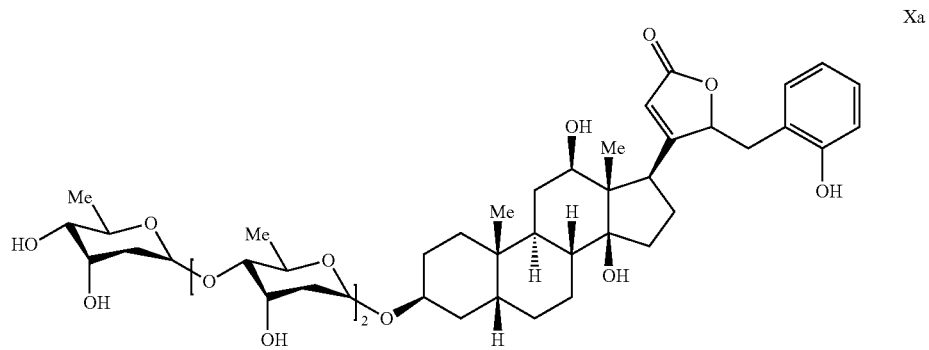
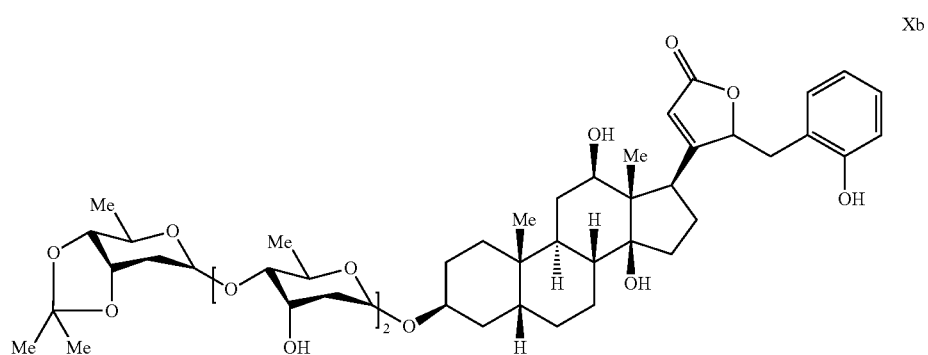
or
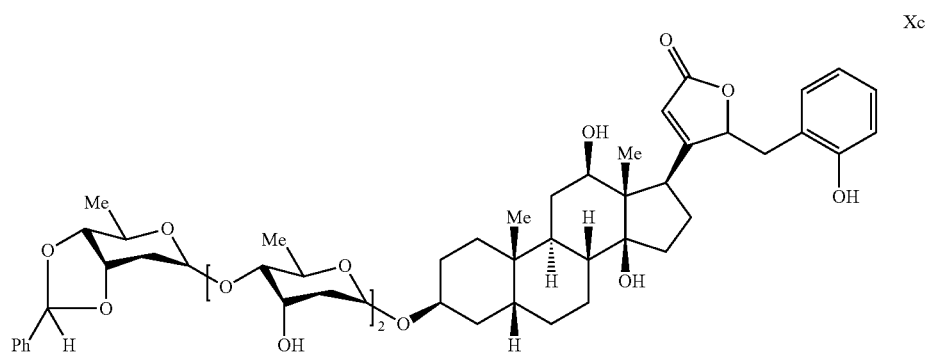

or a pharmaceutically acceptable salt, solvate or prodrug thereof;
and stereoisomers, isotopic variants and tautomers thereof.
In one embodiment, with respect to the compounds of formula I, the compound is according to formula XIa, XIb, or XIc:
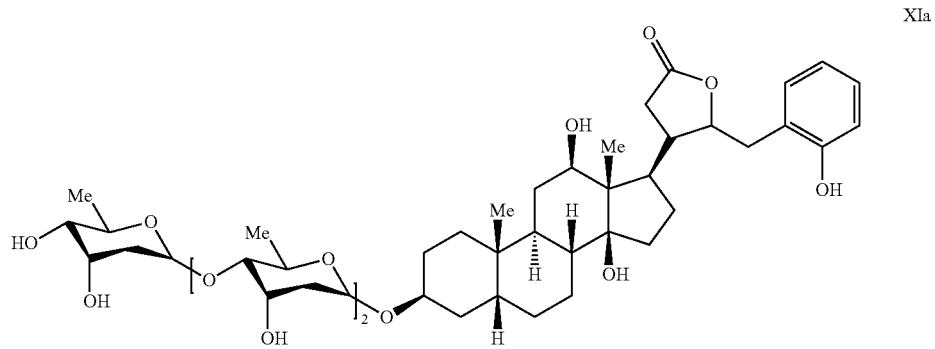
XIa
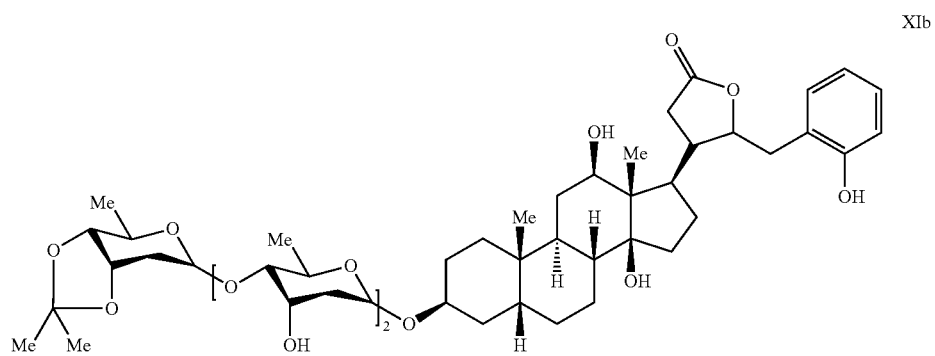
XIb
or
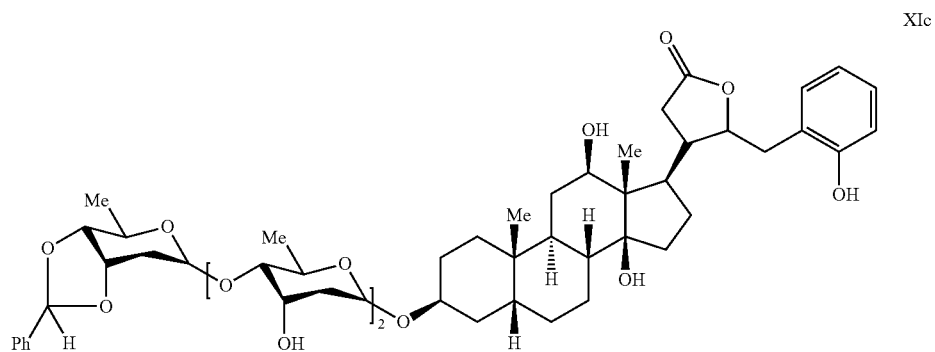
XIc or a pharmaceutically acceptable salt, solvate or prodrug thereof;
and stereoisomers, isotopic variants and tautomers thereof.
In one embodiment, with respect to the compounds of formula I, the compound is according to formula XIIa, XIIb, or XIIc:
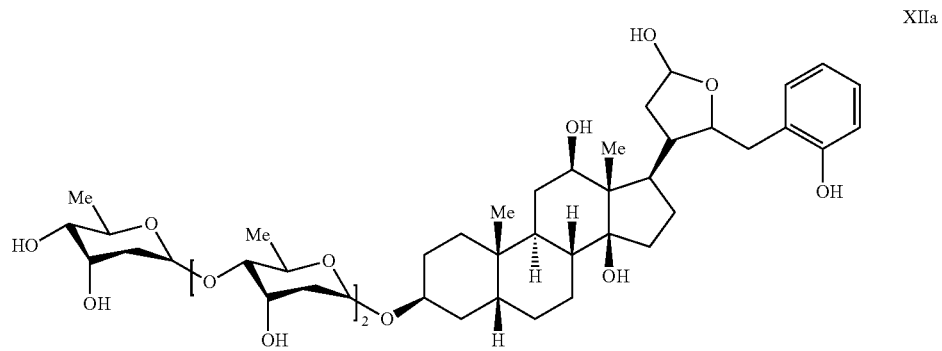
XIIa
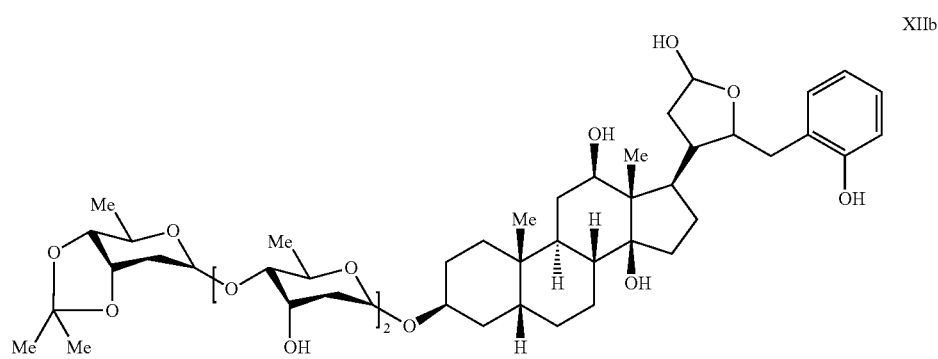
XIIb
or
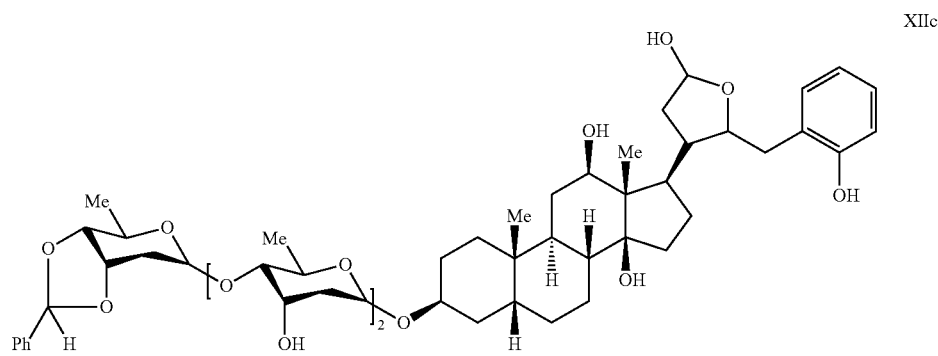
XIIc or a pharmaceutically acceptable salt, solvate or prodrug thereof;

and stereoisomers, isotopic variants and tautomers thereof.

In one particular embodiment, with respect to the compounds of formula VIa-VId, IXa, IXb, or IXc, the compound is an E isomer. In another embodiment, the compound is an Z isomer.

In one embodiment, with respect to the compounds of formula I, the compound is according to formula XIIIa, XIIIb, or XIIIc:

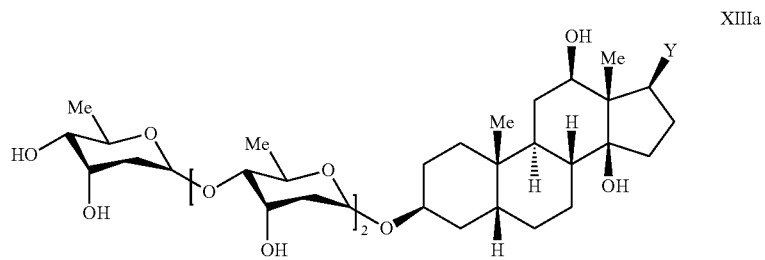

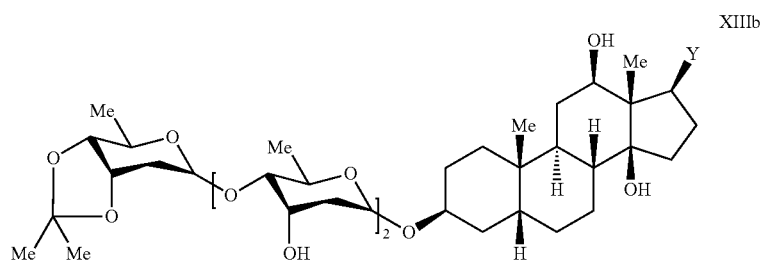

or

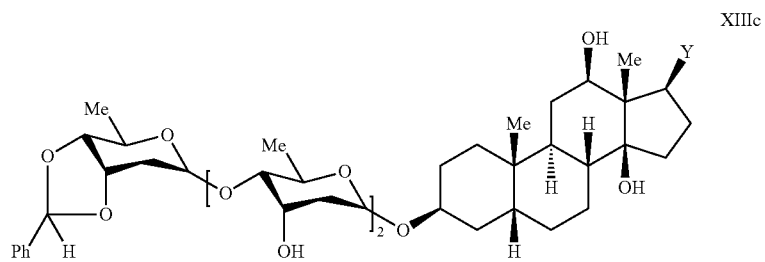

wherein Y is CO₂H, CO₂Me, CO₂Et, CO₂-i-Pr, or CH₂OH;

or a pharmaceutically acceptable salt, solvate or prodrug thereof;

and stereoisomers, isotopic variants and tautomers thereof.

In one particular embodiment, with respect to the compounds of formula XIIIa-c, Y is CO₂H. In another embodiment, Y is CO₂Me. In another embodiment, Y is CO₂Et. In another embodiment, Y is CO₂i-Pr. In another embodiment, Y is CH₂OH.

In one particular embodiment, with respect to the compounds of formula I, the compound is other than:

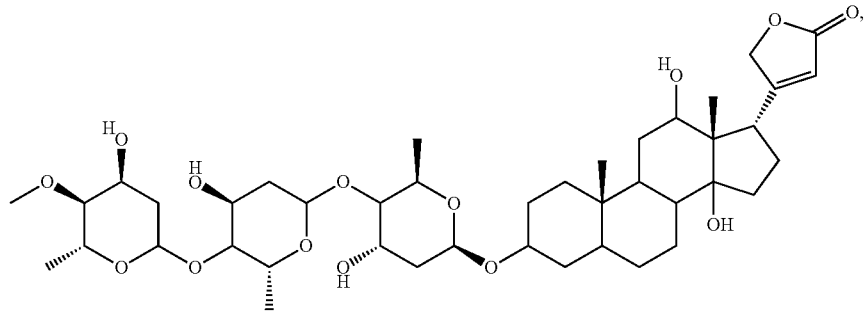

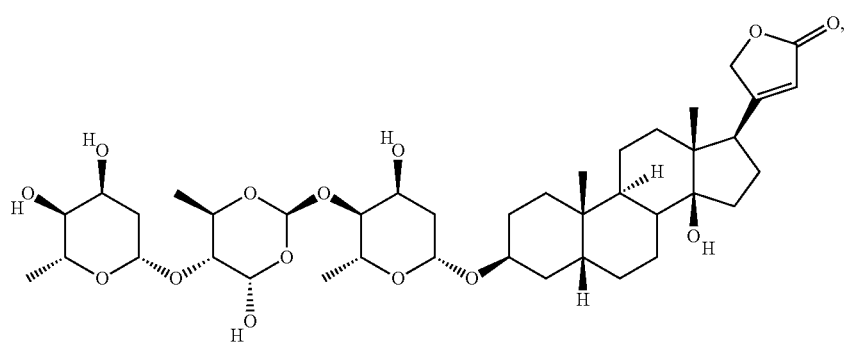

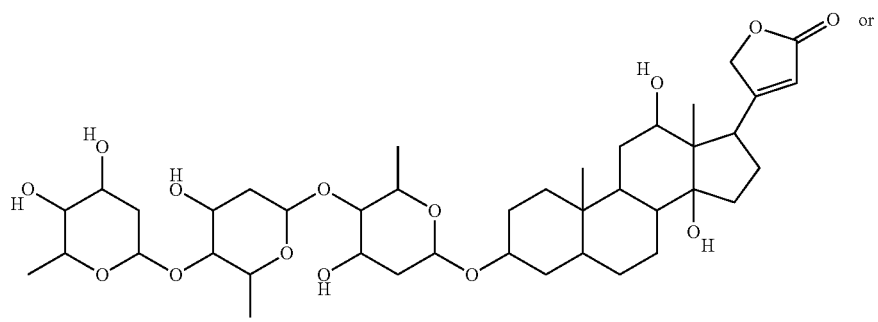

or

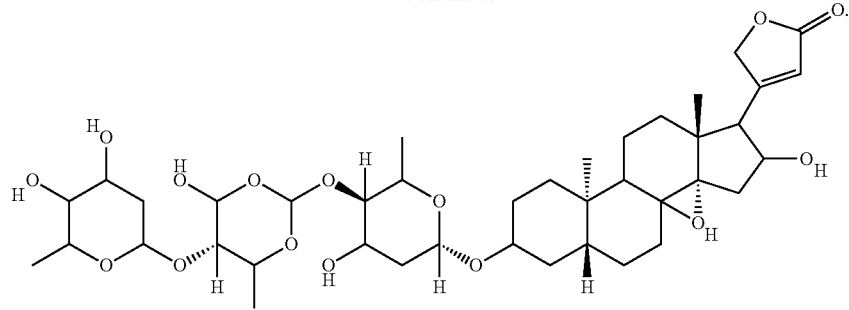
15
In one particular embodiment, with respect to the compounds of formula I, the compound is:
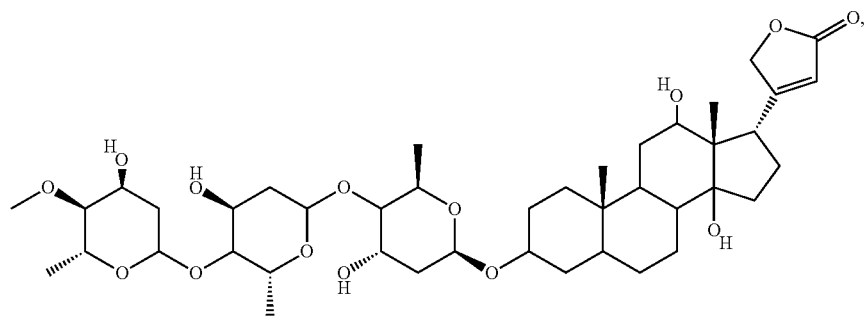
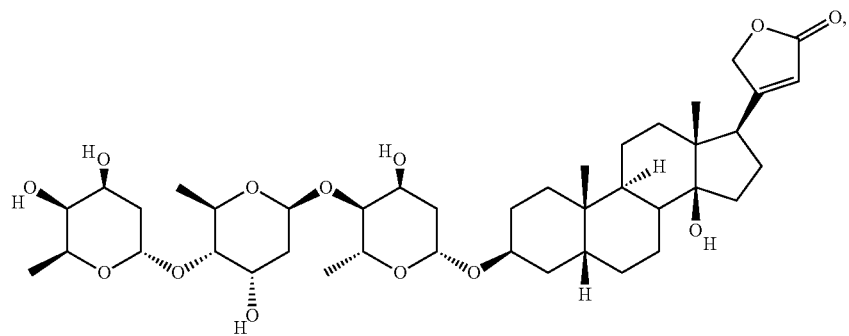
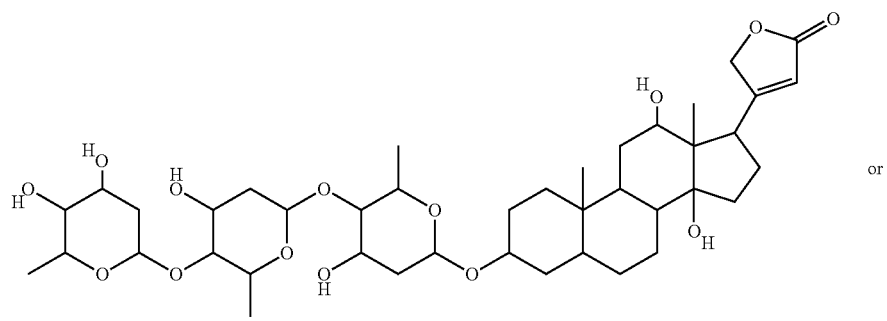
or

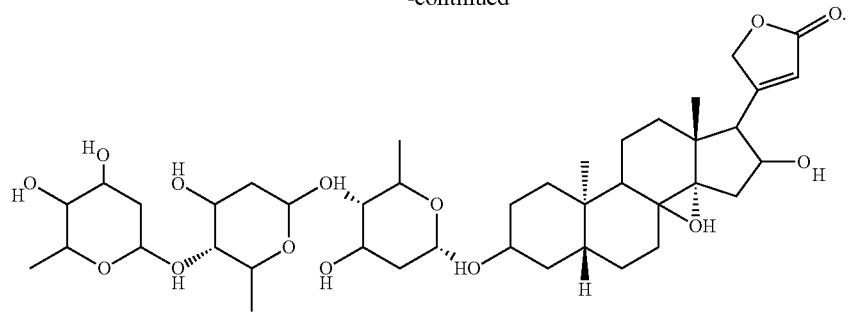

In one particular embodiment, with respect to the compounds of formula I, the compound is selected from Table 1.

In another aspect, the present invention provides pharmaceutical composition of a compound according to formulae I-XIIIc.

In a further aspect, the present invention provides composition comprising a steroid compound of the invention. In a particular embodiment, the compound is according to formula VIa-VId, IXa-IXc, Xa-Xc, XIa-XIc, or XIIa-XIIc.

In a further aspect, the present invention provides a compound according to formula VIa-VId, IXa-IXc, Xa-Xc, XIa-XIc, or XIIa-XIIc.

In a particular embodiment, the compound is according to formula VIa, VIb, VIc, or VId:

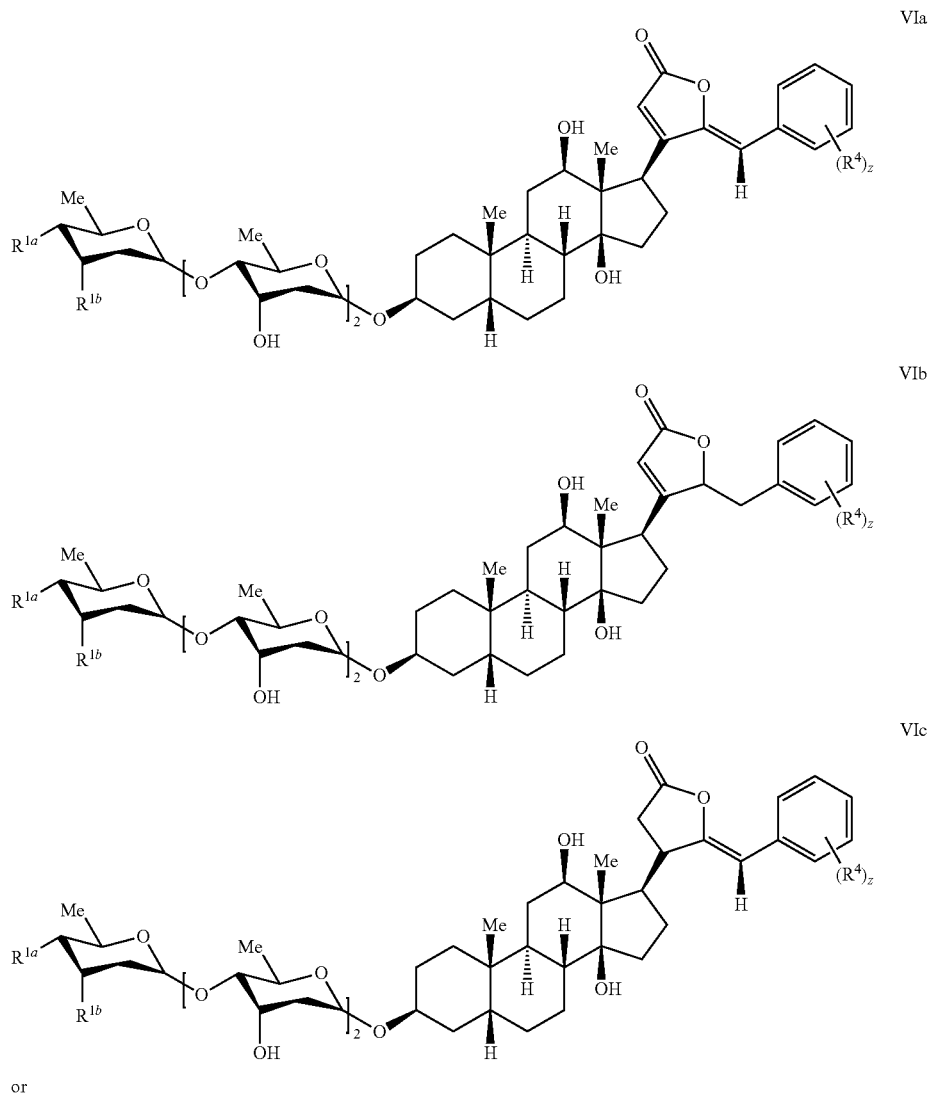

or

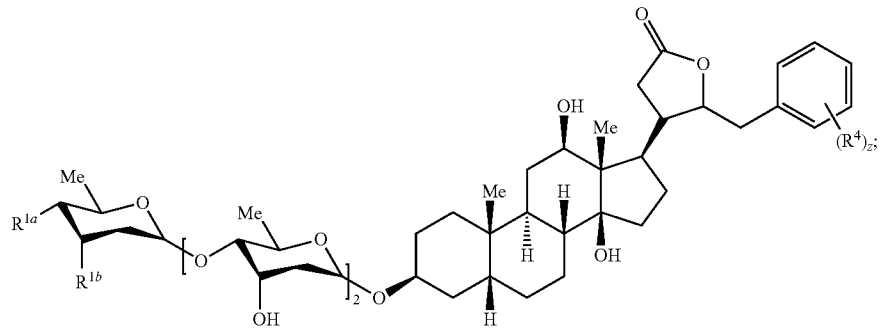

and $R^{1a}$ and $R^{1b}$ are as described for formula I; z is 1, 2, 3; and each $R^4$ is independently selected from substituted or unsubstituted alkyl, substituted or unsubstituted acyl, substituted or unsubstituted acylamino, substituted or unsubstituted alkylamino, substituted or unsubstituted $C_2$-$C_6$ alkoxy; substituted or unsubstituted alkylthio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted heterocycloalkyl, substituted or unsubstituted dialkylamino, iodo, hydroxyl, nitro, and thiol;
or a pharmaceutically acceptable salt, solvate or prodrug thereof;
and stereoisomers, isotopic variants and tautomers thereof.

In one particular embodiment, with respect to the compounds of formula VIa-VId, z is 1 or 2; and each $R^4$ is independently selected from iodo, alkyl, haloalkyl, $C_2$-$C_6$ alkoxy, haloalkoxy, hydroxyl, phenoxy, amino, nitro, benzyloxy, methylenedioxy, and substituted amino.

In one particular embodiment, with respect to the compounds of formula VIa-VId, z is 1 or 2; and each $R^4$ is independently selected from I, Me, OH, OEt, $CF_3$, $OCF_3$, $CF_3$, $NMe_2$, $NO_2$, OPh, and SMe.

In one embodiment, with respect to the method of treatment, the disease or condition is autoimmune disease.

In one embodiment, with respect to the method of treatment, the disease or condition is inflammatory disease.

In one embodiment, with respect to the method of treatment, the disease or condition is selected from arthritis, diabetes, multiple sclerosis (and the animal model thereof, EAE), uveitis, rheumatoid arthritis (and the animal model thereof, CIA), psoriasis, asthma, bronchitis, allergic rhinitis, chronic obstructive pulmonary disease, atherosclerosis, cancer, graft-versus-host disease, H. pylori infections and ulcers resulting from such infection, and inflammatory bowel diseases.

In one embodiment, with respect to the method of treatment, the disease or condition is selected from Crohn's disease, ulcerative colitis, sprue and food allergies.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions of this invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals that are causally related or attributable to RORγt activity. Accordingly, the compounds and pharmaceutical compositions of this invention find use as therapeutics for preventing and/or treating a variety of inflammatory conditions and autoimmune disorders in mammals, including humans.

In a method of treatment aspect, this invention provides a method of treating a mammal susceptible to or afflicted with a condition associated with an inflammatory condition and/or an autoimmune disorder, which method comprises administering an effective amount of one or more of the pharmaceutical compositions just described. Cells that express RORγ/γt include, but are not limited to T cells, NK cells, myeloid cells, brain, liver, lung, heart, and muscle cells. For example, cells that express RORγt include, but are not limited to, T cells, NK cells, and myeloid cells, and cells that express RORγ include, but are not limited to, brain, liver, lung, heart, and muscle cells. Although not wishing to be bound by theory, therefore, methods of treating as described herein are expected to affect cellular activity of cells that express RORγt and/or cells that are responsive to the effects of RORγt expressing cells.

In additional method of treatment aspects, this invention provides methods of treating a mammal susceptible to or afflicted with an inflammatory condition or autoimmune disorder causally related or attributable to RORγt activity. Such conditions and disorders include, without limitation, arthritis, diabetes, multiple sclerosis (and the animal model thereof, EAE), uveitis, rheumatoid arthritis (and the animal model thereof, CIA), psoriasis, asthma, bronchitis, allergic rhinitis, chronic obstructive pulmonary disease, atherosclerosis, cancer, graft-versus-host disease, *H. pylori* infections and ulcers resulting from such infection, and inflammatory bowel diseases. Such methods comprise administering an effective condition-treating or condition-preventing amount of one or more of the pharmaceutical compositions just described.

Further to the above, Th17 cells have been shown to have important roles in activating and directing immune responses in a variety of autoimmune diseases, such as experimental autoimmune encephalomyelitis (EAE), collagen-induced arthritis (CIA), inflammatory bowel disease (IBD), cancer (Weaver, C. et al. *Ann. Rev. Immunol.*, 2007, 25, 821-52; Kryczek, I. et al. *J. Immunol.*, 2007, 178, 6730-3; Cua, D. J. et al. *Nature*, 2003, 421, 744-8; Langrish, C. L. et al. *J. Exp. Med.*, 2005, 201, 233-40; Yen, D. et al. *J. Clin. Invest.*, 2006, 116, 1310-6), and graft-versus-host disease (Carlson, M. J. et al. *Blood*, 28 Oct. 2008. [Epub ahead of print]; Kappel, L. W. et al. *Blood*, 17 Oct. 2008. [Epub ahead of print]). Th17 cells have also been implicated in asthma, psoriasis, rheumatoid arthritis, multiple sclerosis (Tzartos, J. S., et al. *Am. J. Pathology*, 2008, 172, 146-55; Yu, J. J., and Gaffen, S. L. *Front. Biosci.*, 2008, 13, 170-77; and Zheng, Y. et al. *Nature*, 2007, 445, 648-51), and Crohn's disease (Duerr, R. H., et al. *Science*, 2006, 314, 1461-63). Additionally, it has been shown that mice defective for expression of RORγt lack Th17 cells and are resistant to a variety of autoimmune diseases. The absence of Th17-producing microbiota in the small intestine of mice has also been demonstrated to alter the Th17: regulatory T (Treg) cell balance with implications for intestinal immunity, tolerance, and susceptibility to inflammatory bowel diseases (Ivanov, I. I. *Cell Host & Microbe*, 2008, 4, 337-49). The contents of each of which references listed above is incorporated herein by reference in its entirety.

Indeed, it is well accepted that functional RORγt is indispensable for development and maintenance of mouse and human Th17 cells (Huh, J. R., et al. Nature, 2011, 472, 486-490; the contents of which is incorporated herein by reference in its entirety). Th17 cells generally exacerbate inflammation by secreting pro-inflammatory cytokines such as IL-17a. Hyper-inflammation is an underlying mechanism of the aforementioned human diseases. Importantly, a large body of literature establishes that Th17 cells are closely linked to autoimmune and inflammatory diseases such as those listed above and others recognized in the art. Therefore, inhibition of RORγt activity using compounds described herein, which suppress inflammation by Th17 cells and are demonstrated herein to reduce the severity of symptoms associated with exemplary such diseases as shown in FIGS. 2-8, are also expected to reduce the severity of symptoms associated with other autoimmune and inflammatory diseases. Proof of principle of this assertion is presented herein in that the present inventors have demonstrated that treatment with RORγt activity inhibitors reduces the percentage of gut associated Th17 cells in a mouse model of colitis and ameliorates disease severity in a mouse model of multiple sclerosis.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases. Accordingly, also encompassed herein is at least one compound described herein or a composition thereof for use in the treatment of an inflammatory and/or autoimmune disease or condition from among those listed herein, and particularly, such disease or condition as may be causally related to or associated with RORγt activity. Such conditions include, without limitation, multiple sclerosis (and the animal model thereof, EAE), rheumatoid arthritis (and the animal model thereof, CIA), inflammatory bowel disease (IBD), cancer, graft-versus-host disease, asthma, psoriasis, diabetes, uveitis, bronchitis, allergic rhinitis, chronic obstructive pulmonary disease, atherosclerosis, and *H. pylori* infections and ulcers resulting from such infection.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Transdermal doses are generally selected to provide similar or lower blood levels than are achieved using injection doses. Modes of administration suitable for mucosal sites are also envisioned herein and include without limitation: intra-anal swabs, enemas, intranasal sprays, and aerosolized or vaporized compounds and/or compositions for delivery to the lung mucosa. One of skill in the art would choose an appropriate delivery mode/s based on a variety of parameters, including the organ or tissue site in a patient with a disease or condition that is most severely affected by the disease or condition. A skilled practitioner could, for example, treat a patient afflicted with an inflammatory bowel disease (IBD) with a therapeutic regimen that included delivery of the compounds or compositions of the invention using an enema for direct delivery to the bowel.

For the prevention and/or treatment of long-term conditions, such as, e.g., arthritis, diabetes, multiple sclerosis (and the animal model thereof, EAE), rheumatoid arthritis (and the animal model thereof, CIA), psoriasis, or asthma, the regimen for treatment usually stretches over many months or years, so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

When used to prevent the onset of an inflammatory condition or autoimmune disorder, the compounds of this invention will be administered to a patient at risk for developing the condition or disorder, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity and are determined to safe and efficacious for such combined administration.

General Synthetic Procedures

The compounds of this invention may be purchased from various commercial sources or can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds of the invention may be prepared from known or commercially available starting materials and reagents by one skilled in the art of organic synthesis.

Chemicals.

The purity of all synthesized compounds are determined by $^1$H NMR analysis and found to be ~95% of the indicated composition. The following chemicals were purchased from the indicated commercial sources.

| | |
|---|---|
| Digoxigenin | Sigma |
| Ouabain octahydrate | Sigma |
| Digitoxin | Sigma |
| Proscillaridin A | Sigma |
| Digitoxigenin | Sigma |
| Digoxin | Sigma |
| Oleandrin | TRC |
| 19-Hydroxycholesterol | Sigma |
| 20α-Hydroxycholesterol | Sigma |
| 20(S)-Hydroxycholesterol | Sigma |
| β-acetyldigoxin | Serva |
| Digitonin | Sigma |
| Lanatoside C | Sigma |
| Deslanoside | Avachem Scientific |
| Erysimoside | Latoxan |
| Ouabagenin | Sigma |
| 20-Hydroxyecdysone | Sigma |
| 20(R)-Hydroxycholesterol | Sigma |
| 24(S)-Hydroxycholesterol | Steraloids |
| 25-Hydroxycholesterol | Sigma |

Representative Synthetic Method

The representative compounds of the invention can be prepared following the literature methods[#] or using the general synthetic schemes given below.

Scheme 1

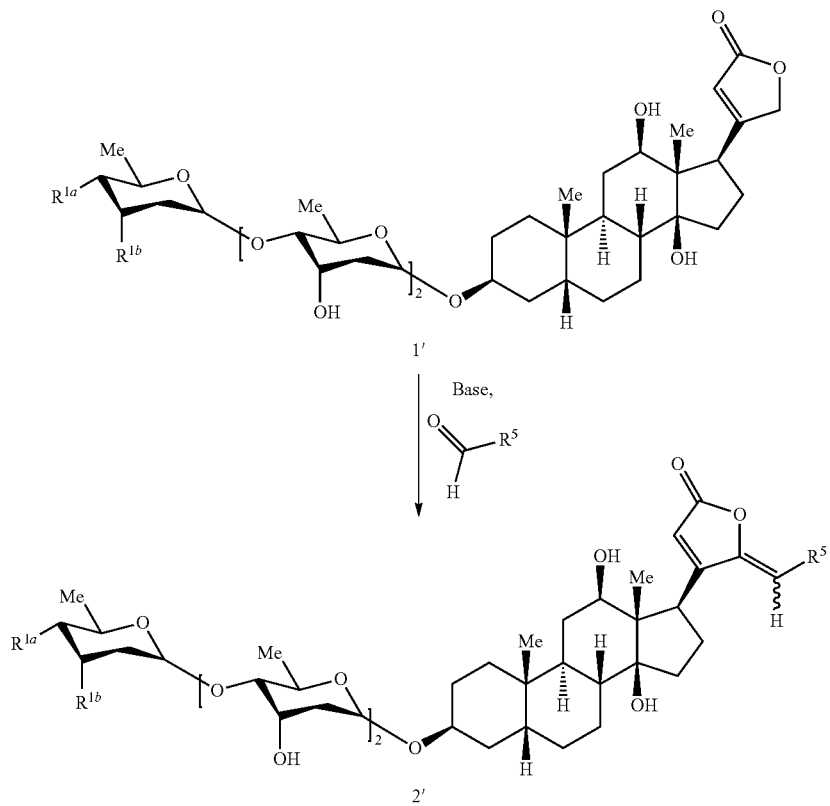

and wherein $R^{1a}$, $R^{1b}$, $R^{6a}$, $R^{6b}$, and Z are as described herein.

Scheme 2

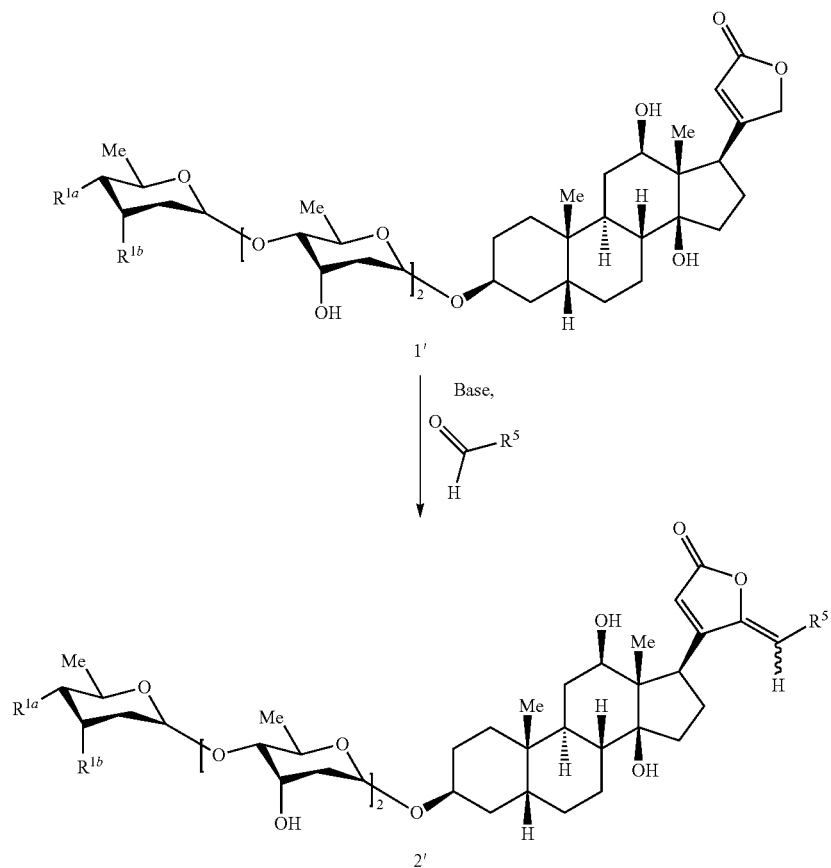

and wherein z, $R^{1a}$, $R^{1b}$, and $R^5$ are as described herein.

The various aldehydes used or can be used in the Scheme 2 reaction are listed below:

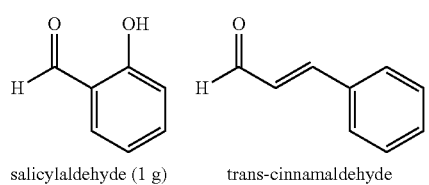

salicylaldehyde (1 g)    trans-cinnamaldehyde

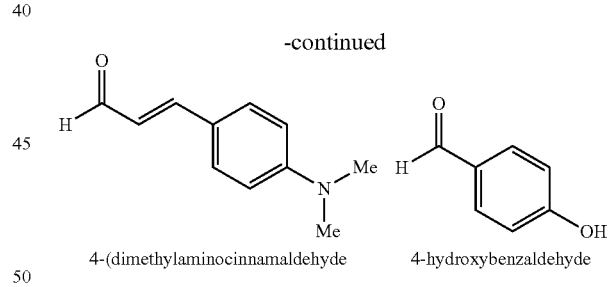

4-(dimethylaminocinnamaldehyde    4-hydroxybenzaldehyde

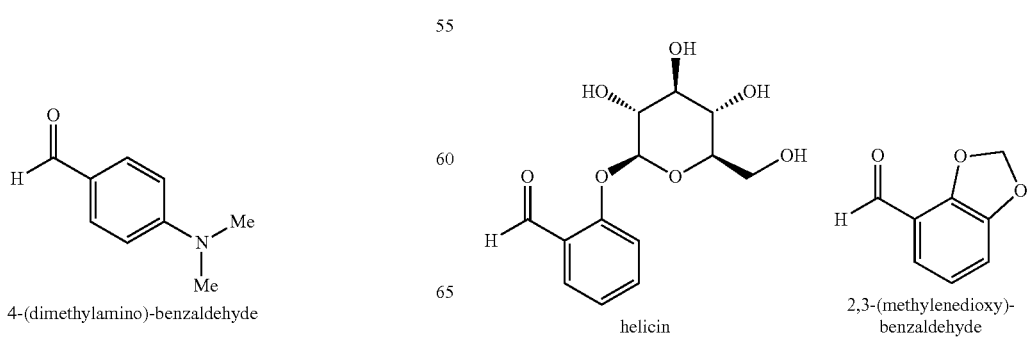

4-(dimethylamino)-benzaldehyde    helicin    2,3-(methylenedioxy)-benzaldehyde

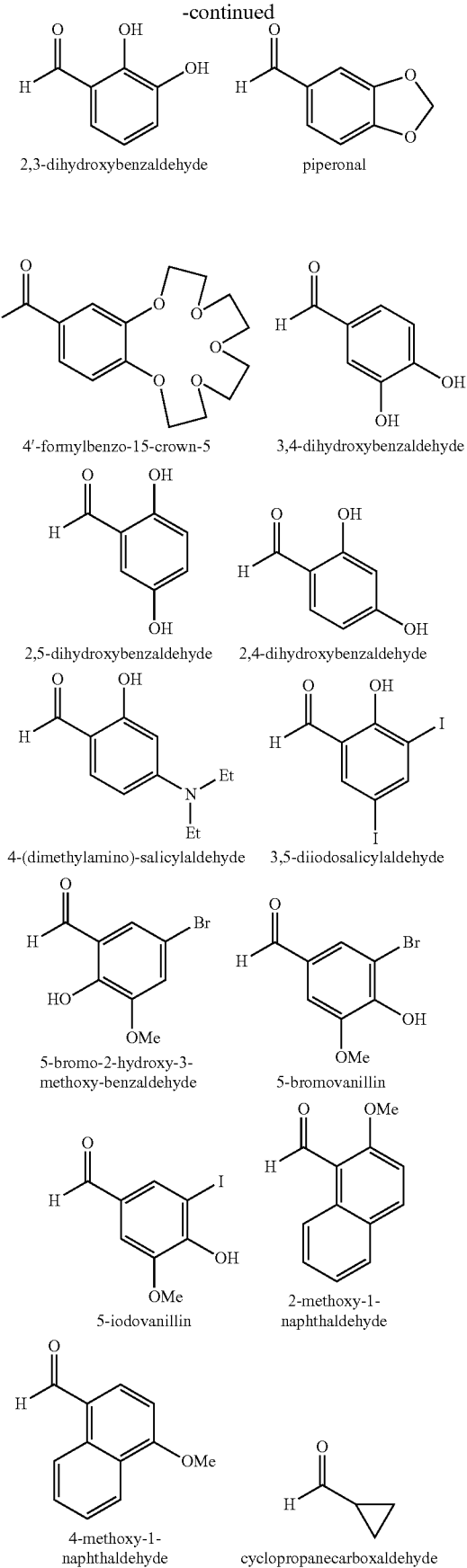
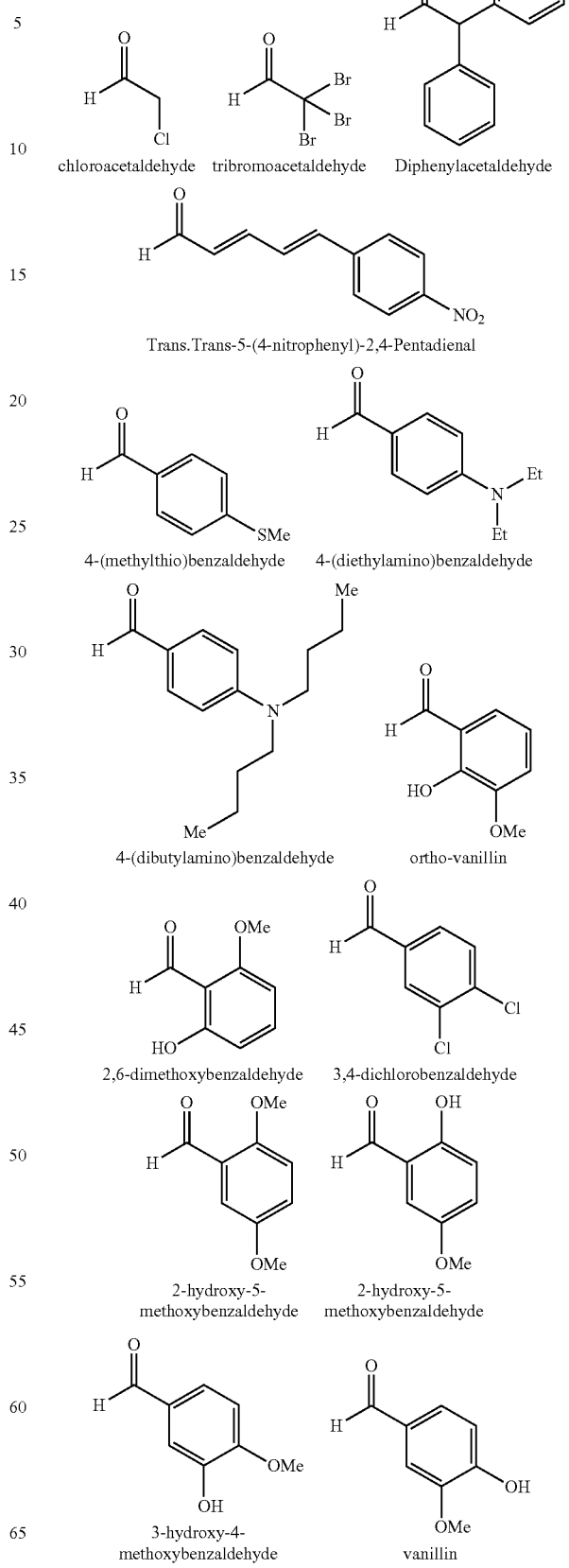

-continued

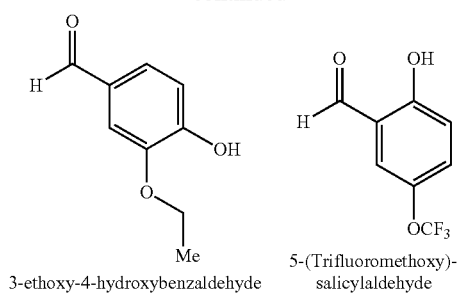

3-ethoxy-4-hydroxybenzaldehyde 5-(Trifluoromethoxy)-salicylaldehyde

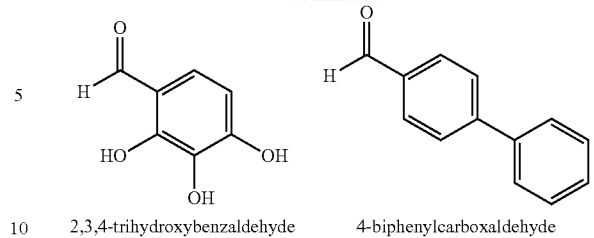

2,3,4-trihydroxybenzaldehyde 4-biphenylcarboxaldehyde 3-(4-methylphenoxy)-benzaldehyde

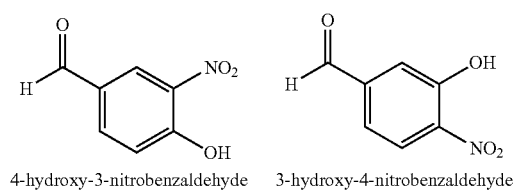

4-hydroxy-3-nitrobenzaldehyde 3-hydroxy-4-nitrobenzaldehyde

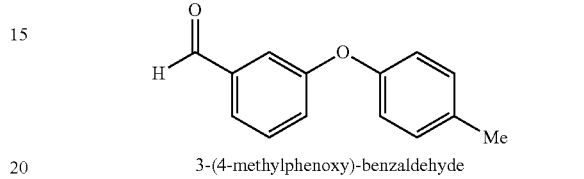

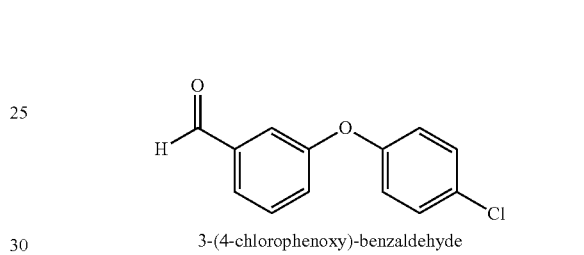

3-(4-chlorophenoxy)-benzaldehyde

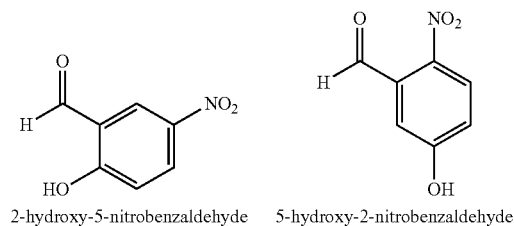

2-hydroxy-5-nitrobenzaldehyde 5-hydroxy-2-nitrobenzaldehyde

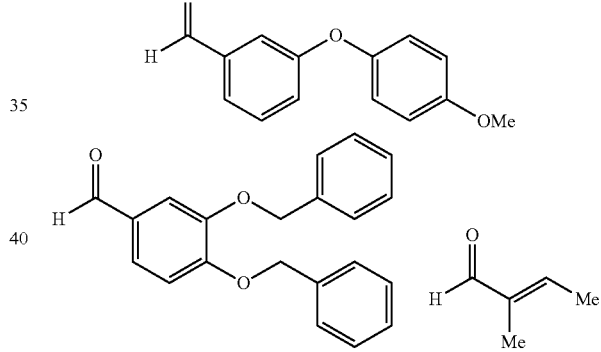

3-4-dibenzyloxybenzaldehyde trans-2-methyl-2-butenal

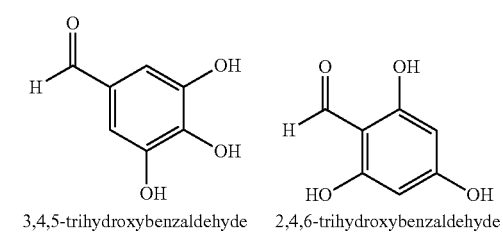

3,4,5-trihydroxybenzaldehyde 2,4,6-trihydroxybenzaldehyde

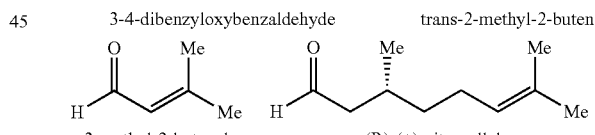

3-methyl-2-butenal (R)-(+)-citronellal (S)-(-)-perillaldehyde (1R)-(-)-myrtenal

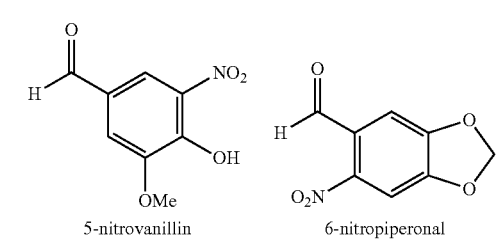

5-nitrovanillin 6-nitropiperonal

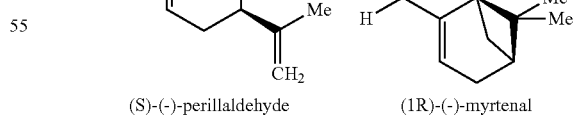

[#]Digoxin derivatives substituted by alkylidene at the butenolide part, Xu et al, *Steroids* (2010), 75(6), 419-423; 21-Sub-unit Digoxin derivatives and their preparation method, Liu et al; Faming Zhuanli Shenqing Gongkai Shuomingshu (2007), CN 101041683; Facile synthesis of γ-alkyliden-ebutenolides; Xu et al, Organic & Biomolecular Chemistry (2007), 5(8), 1247-1250.

Scheme 3
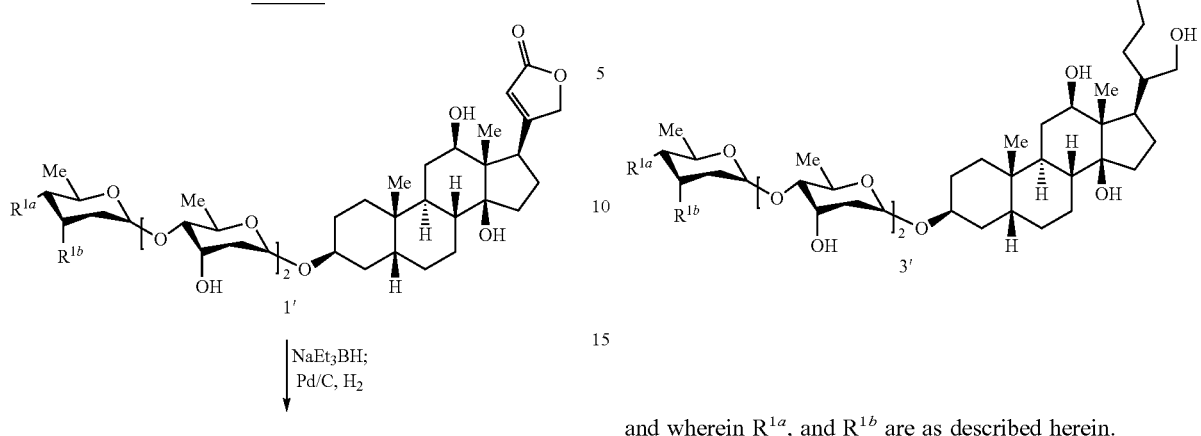
and wherein $R^{1a}$, and $R^{1b}$ are as described herein.
Scheme 4
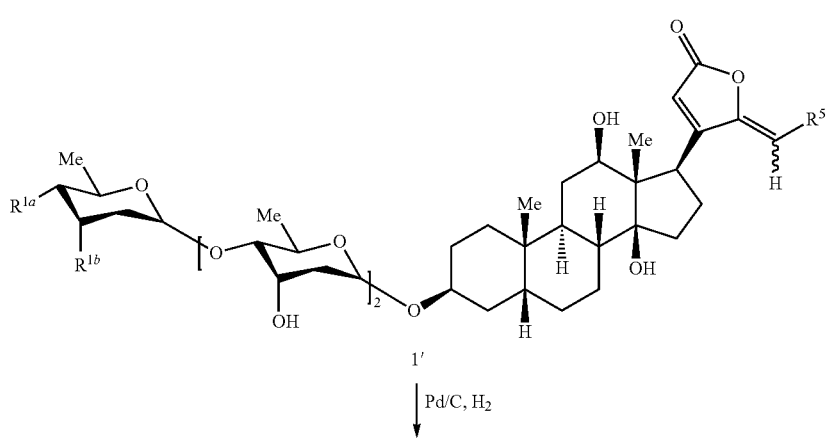
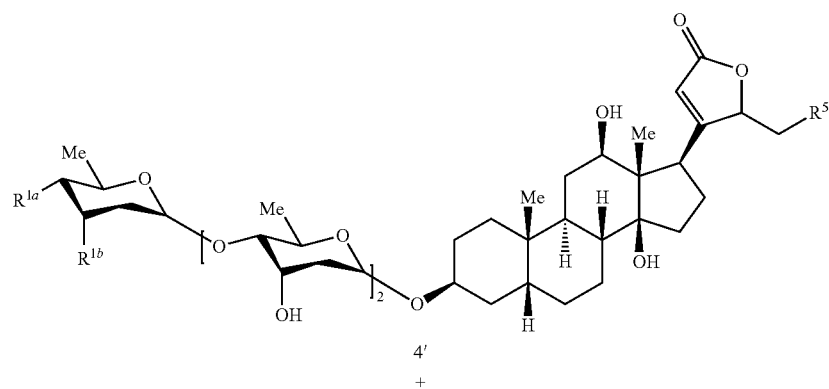
+

-continued
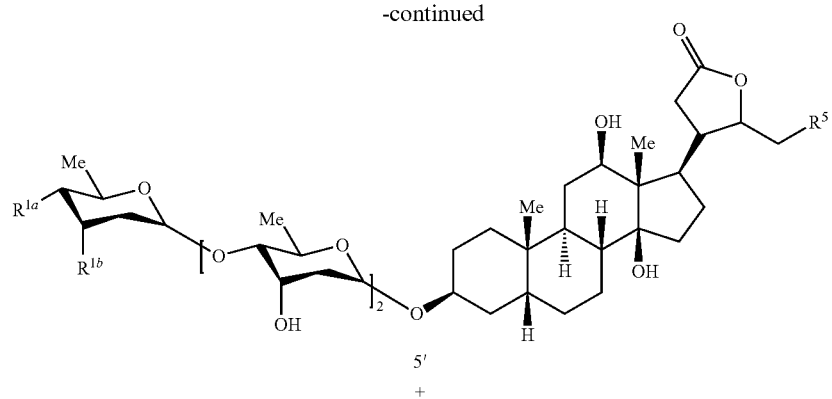
5'
+
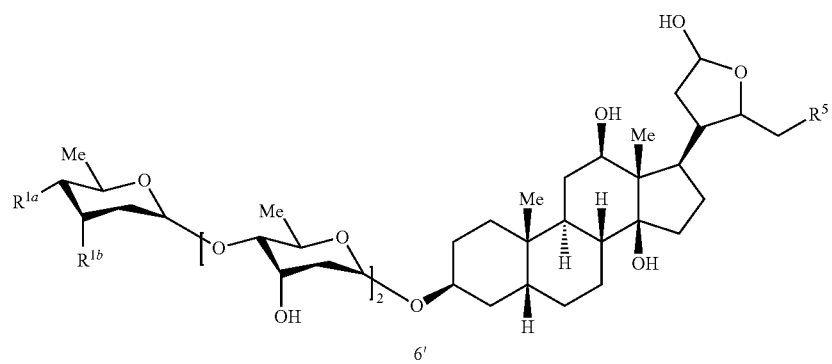
40
and wherein $R^{1a}$, $R^{1b}$, and $R^5$ are as described herein.
Scheme 5
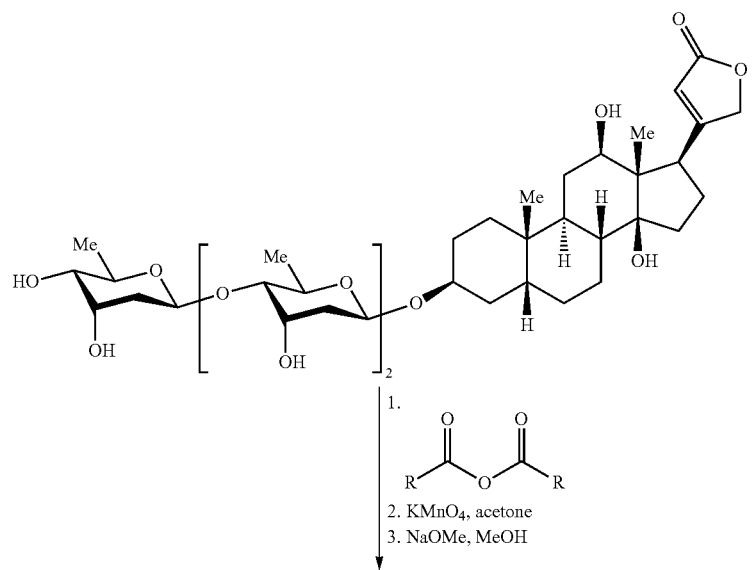
1. 
2. KMnO$_4$, acetone
3. NaOMe, MeOH -continued

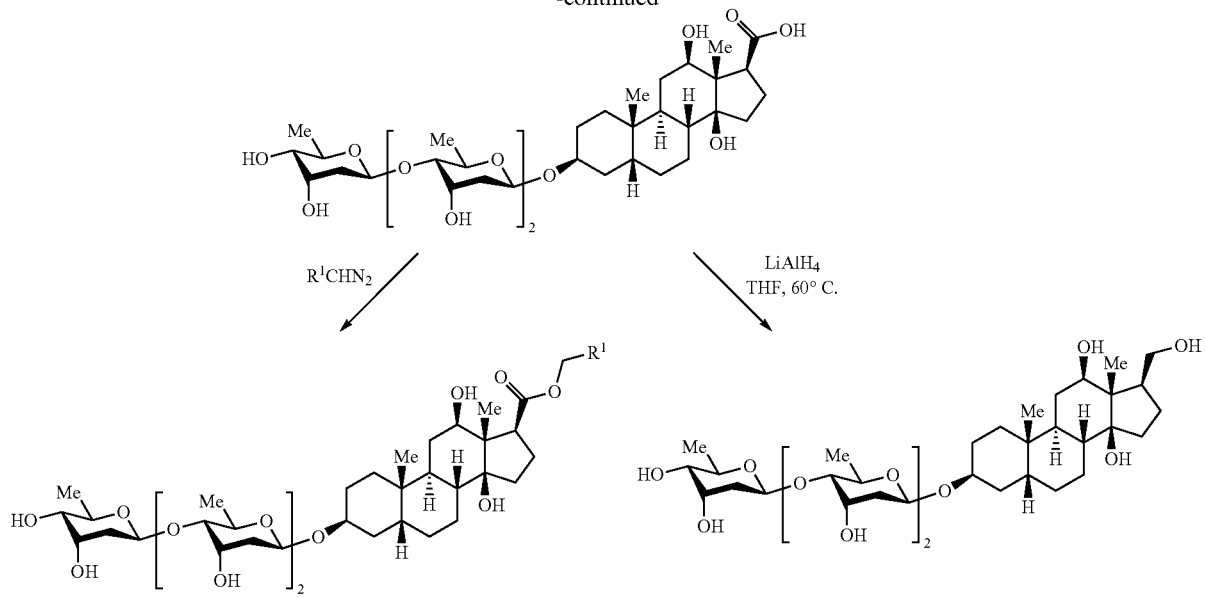

Synthesis of Representative Compounds

Example 1

Compound 13

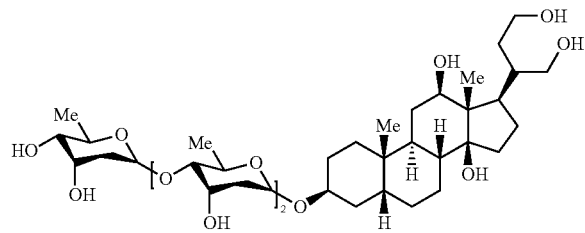

20,22-Dihydrodigoxin-21,23-diol (Dig(dhd))

Sodium triethylborohydride (840 μL of a 1M solution in THF, 0.843 mmol, 10 equiv) was added dropwise to a room temperature solution of digoxin (65.8 mg, 0.0843 mmol, 1.0 equiv) in THF (16.9 mL, 5 mM). After 10 min, the reaction was quenched with the slow addition of methanol (5 mL), stirred for 15 min, and concentrated in vacuo to afford an inseparable mixture of saturated diol (Dig(dhd)) and alkene diol (20,22-alkene) (~3:1 of saturated:alkene) as a white solid. Rf=0.15 (9:1 ethyl acetate/methanol). The crude material was used as such without further purification.

To the above mixture of compounds in methanol (4.2 mL, 20 mM) was added 10 wt % palladium on carbon (9.0 mg, 0.0084 mmol, 0.1 equiv). The reaction atmosphere was sparged with hydrogen and the contents were stirred under a balloon of hydrogen for 16 h, at which point the reaction was filtered through Celite and concentrated in vacuo. The crude material was dry-loaded onto Celite and purified by flash chromatography on silica gel (19:1→9:1→85:15 dichloromethane/methanol) to afford Dig(dhd) (63.7 mg, 0.0809 mmol, 96% yield over two steps) as a white solid. Dig(dhd) was obtained as a ~1.5:1 mixture of diastereomers that were not separated.

Rf=0.20 (85:15 dichloromethane/methanol);

$^1$H NMR (600 MHz, CD$_3$OD): δ 4.94-4.90 (comp m, 3H), 4.25-4.23 (m, 2H), 4.02-4.00 (m, 2H), 3.88-3.75 (comp m, 2.5H), 3.68-3.61 (m, 1H), 3.62 (app t, J=7.0 Hz, 1H), 3.54 (dd, J=16.8, 6.1 Hz, 0.6H), 3.48 (dd, J=10.9, 5.8 Hz, 0.6H), 3.44 (dd, J=11.1, 6.9 Hz, 0.4H), 3.31-3.21 (comp m, 4.8H), 3.15 (dd, J=9.6, 3.1 Hz, 1H), 2.30-2.23 (m, 1H), 2.18 (ddd, J=14.2, 7.2, 7.2 Hz, 0.6H), 1.95-1.44 (comp m, 22.6H), 1.33-1.20 (comp m, 4H), 1.24 (d, J=6.2 Hz, 3H), 1.22 (d, J=6.2 Hz, 3H), 1.20 (d, J=6.2 Hz, 3H), 0.96 (s, 1.2H), 0.95 (s, 3H), 0.91 (s, 1.8H);

$^{13}$C NMR (151 MHz, CD$_3$OD): δ 100.7, 100.5, 96.9, 87.3, 87.0, 83.8, 83.6, 79.3, 78.7, 74.4, 74.2, 70.8, 69.5, 69.4, 69.1, 68.5, 68.3, 66.9, 65.1, 62.6, 62.1, 54.6 (two lines), 48.2, 42.5, 42.1, 41.0, 39.8, 39.4, 38.9, 38.5, 37.9, 37.0, 36.1, 33.7, 32.8 (two lines), 31.4, 31.0, 30.9, 30.7, 27.9, 27.8, 27.5, 24.5, 24.3 (two lines), 22.9, 22.8, 18.7, 18.5, 18.4, 9.6, 9.4;

IR (Neat Film, NaCl): 3406 (br), 2933, 1641, 1406, 1370, 1166, 1130, 1068, 1014, 869 cm−1;

HRMS (ESI+) m/z calc'd for $C_{41}H_{70}O_{14}Na$ [M+Na]$^+$: 809.4663. found 809.4662.

[α]$D^{18.4}$+16.4° (c=0.33, CH$_3$OH).

Example 2

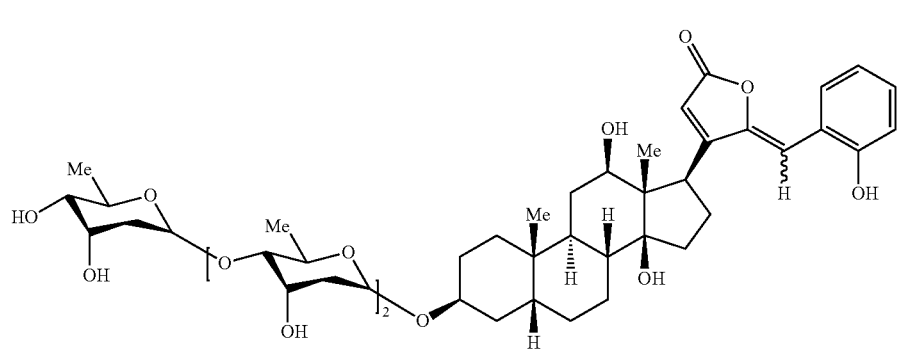

Compound 15

Digoxin-21-salicylidene (Dig(sal)) Synthesis

Sodium carbonate (15.0 mg, 0.142 mmol, 1.1 equiv) was added to a suspension of digoxin (99.8 mg, 0.128 mmol, 1.0 equiv) and salicylaldehyde (77.81 μL, 0.639 mmol, 5.0 equiv) in methanol (5.1 mL, 25 mM), at which point the contents turned yellow in color. A reflux condenser was affixed to the flask and the contents were warmed to reflux in a 125° C. oil bath. The reaction was cooled to room temperature after 23 h and concentrated in vacuo. The crude material was dry-loaded onto Celite and purified by flash chromatography on silica gel (1:0→19:1 ethyl acetate/methanol) to afford Dig(sal) (30.3 mg, 0.0342 mmol, 27% yield) as a pale yellow solid in ~8:1 dr. Mixed fractions containing the desired compounds were repurified by flash chromatography on silica gel (1:0→19:1→9:1 dichloromethane/methanol) to yield an additional 30.1 mg (0.0340 mmol, 27% yield) of Dig(sal) in ~3:1 dr.

Rf=0.38 (19:1 ethyl acetate/methanol), 0.34 (9:1 dichloromethane/methanol);

$^1$H NMR (600 MHz, CD$_3$OD): δ 8.05 (dd, J=7.9, 1.3 Hz, 1H), 7.22 (app dd, J=9.7, 7.6 Hz, 0.6H), 7.20 (s, 1H), 7.14 (ddd, J=8.3, 8.3, 1.4 Hz, 1H), 6.87-6.82 (comp m, 3H), 6.50 (d, J=1. Hz, 0.3H), 6.18 (s, 1H), 4.94-4.86 (comp m, 4H), 4.25-4.22 (comp m, 3H), 4.02 (app dd, J=6.5, 3.2 Hz, 2.6H), 3.97 (br s, 0.4H), 3.86-3.75 (comp m, 4.5H), 3.59 (dd, J=9.7, 5.4 Hz, 1H), 3.52 (dd, J=10.0, 6.0 Hz, 0.4H), 3.49 (dd, J=11.9, 4.1 Hz, 1H), 3.32 (ddd, J=9.7, 9.7, 2.9 Hz, 2.8H), 3.20-3.19 (comp m, 0.3H), 3.15 (dd, J=9.6, 3.0 Hz, 1.6H), 2.92 (dd, J=11.7, 4.1 Hz, 0.4H), 2.35-2.31 (m, 1.2H), 2.25-2.17 (compm, 0.6H), 2.08-2.01 (comp m, 5.3H), 1.95-1.68 (comp m, 21H), 1.53-1.41 (comp m, 5.8H), 1.35-1.18 (comp m, 18H), 0.95 (s, 3H), 0.89 (s, 1H), 0.80 (s, 3H), 0.68 (s, 1H);

$^{13}$C NMR (151 MHz, CD$_3$OD): δ 172.7, 172.0, 168.4, 166.2, 157.9, 157.1, 152.3, 151.1, 132.8, 132.3, 131.5, 131.4, 121.9, 121.7, 121.5, 120.7, 120.1, 116.6, 116.2, 115.6, 114.5, 107.4, 100.7, 100.5, 96.9, 87.6, 87.0, 83.8, 83.6, 76.2, 75.9, 74.4, 74.3, 70.8, 69.5 (two lines), 69.1, 68.5, 68.3, 57.5, 57.4, 49.6, 45.0, 43.6, 42.3, 42.2, 39.5, 38.9, 38.5, 38.0, 36.2, 36.1, 33.8, 33.5, 33.3, 33.0, 31.4, 31.3, 31.1 (two lines), 30.9, 30.7, 27.8, 27.7, 27.5, 24.2 (two lines), 22.8, 22.7, 18.7, 18.5, 18.4, 10.0, 9.9;

IR (Neat Film, NaCl): 3417 (br), 2933, 1734, 1602, 1584, 1454, 1406, 1164, 1068, 1015, 956, 868 cm-1;

HRMS (ESI+) m/z calc'd for C$_{48}$H$_{68}$O$_{15}$Na [M+Na]$^+$: 907.4456. found 907.4471.

[α]D$^{18.5}$+43.2° (c=0.51, CH$_3$OH).

Example 3'

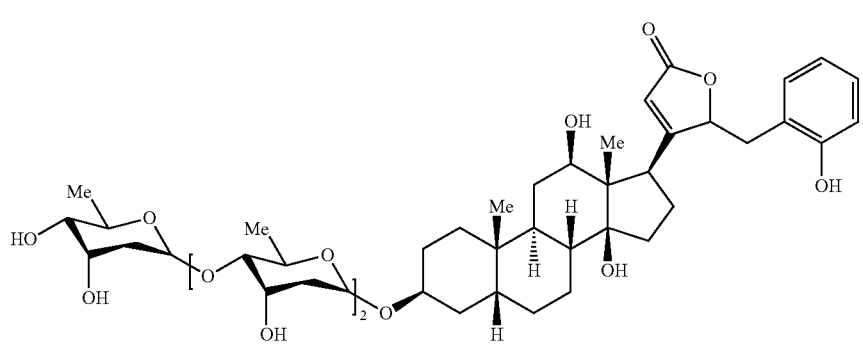

Compound 18

Digoxin-21-salicylyl Synthesis

Palladium on carbon (6.0 mg, 5.6 µmol, 0.25 equiv, 10 wt %) was added to a solution of Compound 15 (19.7 mg, 22.3 µmol, 1.0 equiv) in methanol (1.1 mL, 20 mM) in a 1 dram vial. The vial was place in a high-pressure bomb apparatus and pressurized to 150 psi using $H_2$. The bomb was carefully vented, and this process was repeated two more times. Finally, the bomb was pressurized to 100 psi of $H_2$, and the bomb was placed on a stir plate with stirring at room temperature.

The bomb was depressurized after 89 h and the contents were filtered through a Celite plug, flushing with ethyl acetate, and concentrated in vacuo. The crude material was purified by flash chromatography on silica gel (19:1→9:1 dichloromethane/methanol) to afford a mixture of compounds that contain Compound 18. This material was repurified by preparative thin-layer chromatography (9:1 dichloromethane/methanol, developed thrice) to yield the Compound 18 (2.0 mg, 2.3 µmol, 10% yield) as an off-white solid as a mixture of two diastereomers by $^1$H NMR that were not further separated.

$R_f$=0.46 (9:1 dichloromethane/methanol, developed thrice); $^1$H NMR (500 MHz, CD$_3$OD): δ 7.13-7.02 (comp m, 4.2H), 6.79-6.72 (comp m, 4.2H), 6.16 (d, J=1.6 Hz, 1H), 5.29 (d, J=11.0 Hz, 1H), 4.94-4.89 (comp m, 7.6H), 4.24 (d, J=3.1 Hz, 5.1H), 4.02-4.01 (comp m, 5.1H), 3.85-3.76 (comp m, 8.9H), 3.44 (dd, J=12.1, 4.5 Hz, 1.8H), 3.25-3.21 (comp m, 8.9H), 3.15 (dd, J=9.6, 3.2 Hz, 0.9H), 3.03-2.91 (comp m, 0.9H), 2.62 (dd, J=17.8, 9.2 Hz, 0.8H), 2.53-2.13 (comp m, 6H), 2.03-1.49 (comp m, 56H), 1.32-1.19 (comp m, 31H), 0.97 (s, 3H), 0.94 (s, 2H), 0.90 (s, 3H), 0.85 (s, 2H); IR (Neat Film, NaCl): 3408 (br), 2934, 1732, 1456, 1370, 1165, 1067, 1014, 868 cm$^{-1}$; LRMS (ESI+) m/z calc'd for $C_{48}H_{70}O_{15}Na$ [M+Na]$^+$: 909.5. found 909.7.

Example 4'

The synthesis of Compound 19 was performed exactly as that described for Compound 18 using Compound 15 (19.7 mg, 22.3 µmol, 1.0 equiv), palladium on carbon, hydrogen gas, and methanol. The crude reaction mixture was filtered through a Celite plug, flushing with ethyl acetate, and concentrated in vacuo. The crude material was purified by flash chromatography on silica gel (19:1→9:1 dichloromethane/methanol) to afford a mixture of compounds that contain Compound 19. This material was repurified by preparative thin-layer chromatography (9:1 dichloromethane/methanol, developed thrice) to yield the Compound 19 (1.7 mg, 1.9 µmol, 9% yield) as an off-white solid that appears to be one diastereomer by $^1$H NMR.

$R_f$=0.39 (9:1 dichloromethane/methanol, developed thrice); $^1$H NMR (500 MHz, CD$_3$OD): δ 7.04-7.02 (m, 2H), 6.76-6.72 (m, 2H), 4.94-4.89 (comp m, 5H), 4.24 (d, J=2.6 Hz, 2H), 4.01 (d, J=2.8 Hz, 2H), 3.86-3.75 (comp m, 3H), 3.25-3.21 (m, 2H), 3.19-3.14 (m, 2H), 2.99-2.91 (m, 1H), 2.69-2.51 (comp m, 1.6H), 2.44-2.39 (m, 1H), 2.27-2.21 (m, 1H), 2.04-2.00 (m, 2H), 1.96-1.45 (comp m, 19H), 1.25-1.20 (comp m, 12H), 0.98 (s, 3H), 0.95 (s, 3H); IR (Neat Film, NaCl): 3411 (br), 2934, 1760, 1455, 1368, 1165, 1067, 1013, 868 cm$^{-1}$; LRMS (ESI+) m/z calc'd for $C_{48}H_{72}O_{15}Na$ [M+Na]$^+$: 911.5. found 911.5.

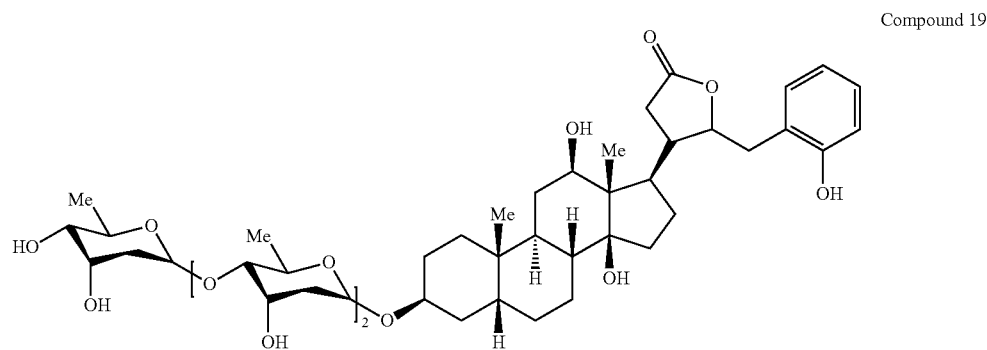

Compound 19

Example 5'

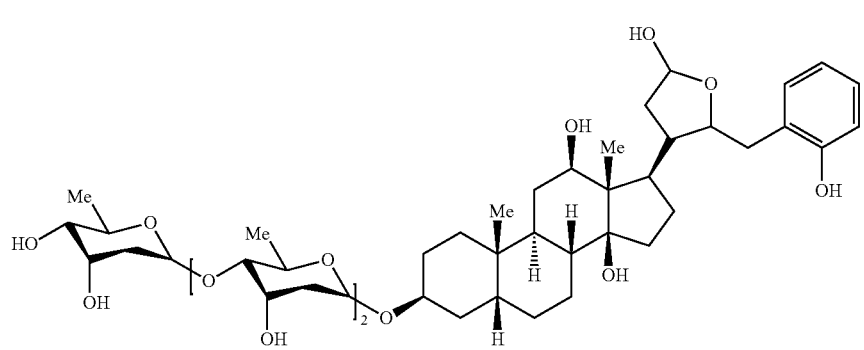

Compound 20

Digoxin-21-salicylyl Synthesis

The synthesis of Compound 20w as performed exactly as that described for Compound 18 using Compound 15 (19.7 mg, 22.3 μmol, 1.0 equiv), palladium on carbon, hydrogen gas, and methanol. The crude reaction mixture was filtered through a Celite plug, flushing with ethyl acetate, and concentrated in vacuo. The crude material was purified by flash chromatography on silica gel (19:1→9:1 dichloromethane/methanol) to afford Compound 20 (5.1 mg, 5.7 μmol, 26% yield) as a white solid that appears to be one diastereomer by $^1$H NMR.

$R_f$=0.21 (9:1 dichloromethane/methanol, developed twice); $^1$H NMR (500 MHz, CD$_3$OD): δ 7.05 (d, J=7.2 Hz, 1H), 6.95 (app t, J=7.6 Hz, 1H), 6.79-6.68 (m, 2H), 4.94-4.89 (comp m, 5H), 4.25-4.23 (m, 2H), 4.02-3.99 (m, 2H), 3.86-3.75 (comp m, 3H), 3.22 (app dt, J=9.8, 2.8 Hz, 2H), 3.15 (dd, J=9.6, 3.1 Hz, 1H), 2.72-2.66 (m, 1H), 2.54-2.40 (m, 2H), 2.14-1.31 (comp m, 21H), 1.24-1.19 (comp m, 12H), 0.94 (s, 3H), 0.91 (s, 3H); $^{13}$C (151 MHz, CD$_3$OD): δ 156.2, 131.0, 130.6, 127.6, 120.4, 115.8, 100.7, 100.5, 96.9, 87.2, 83.8, 83.6, 79.7, 74.5, 74.2, 70.8, 69.5, 69.4, 69.1, 68.5, 68.3, 54.5, 51.7, 42.5, 39.5, 38.9, 38.5, 38.0, 36.2, 33.8, 32.9, 32.6, 31.4, 31.0, 30.3, 29.0, 27.9, 27.5, 25.4, 24.4, 22.9, 18.7, 18.5, 18.4, 9.2; IR (Neat Film, NaCl): 3397 (br), 2936, 1709 (w), 1455, 1408, 1168, 1070, 1018, 871, 756 cm$^{-1}$; LRMS (ESI+) m/z calc'd for C$_{48}$H$_{74}$O$_{15}$Na [M+Na]$^+$: 913.5. found 913.6.

Example 6'

Compound 21.

Digoxin (56.7 mg, 72.6 μmol, 1.0 equiv) was partially dissolved in acetic anhydride (2.9 mL, 25 mM), a reflux condenser was affixed to the flask and the contents were warmed to reflux in a 160° C. oil bath. Upon consumption of digoxin by TLC analysis (90 min), the reaction was cooled to room temperature and concentrated in vacuo. The resulting white paste was dissolved in dichloromethane (50 mL) and washed with NaHCO$_3$ (15 mL). The aqueous layer was extracted with dichloromethane (15 mL). The combined organics were washed with 0.1 M HCl (15 mL), and the acidic aqueous layer was extracted with dichloromethane (15 mL). The combined organics were washed with brine, dried over MgSO$_4$, filtered, and concentrated. The crude material was purified by flash chromatography on silica gel (0→50% ethyl acetate in dichloromethane) and azeotroped with heptane to afford Compound 21 (69.5 mg, 70.1 μmol, 97% yield) as a white solid.

$R_f$=0.32 (1:1 dichloromethane/ethyl acetate); $^1$H NMR (500 MHz, CDCl$_3$): δ 5.85 (br s, 1H), 5.42 (app q, J=3.2 Hz, 1H), 5.38 (app q, J=3.3 Hz, 1H), 5.35 (app q, J=3.3 Hz, 1H), 4.87 (dd, J=18.1, 1.8 Hz, 1H), 4.79 (dd, J=9.8, 2.2 Hz, 1H), 4.77 (dd, J=17.8, 1.7 Hz, 1H), 4.72 (dd, J=9.7, 2.3 Hz, 1H), 4.69 (dd, J=9.7, 2.2 Hz, 1H), 4.62 (dd, J=11.9, 4.1 Hz, 1H), 4.52 (dd, J=9.9, 3.1 Hz, 1H), 3.99 (br s, 1H), 3.89-3.78 (comp m, 3H), 3.32 (dd, J=9.4, 3.1 Hz, 1H), 3.28 (dd, J=9.5, 3.2 Hz, 1H), 2.89 (dd, J=8.6, 6.9 Hz, 1H), 2.19-2.13 (m, 1H), 2.10 (s, 3H), 2.10 (s, 3H), 2.10 (s, 3H), 2.09 (s, 3H), 2.06-1.65 (comp m, 19H), 1.50-1.38 (comp m, 4H), 1.27-1.20 (comp m, 12H), 1.14 (d, J=6.2 Hz, 3H), 0.93 (s, 3H), 0.89 (s, 3H); LRMS (ESI+) m/z calc'd for C$_{51}$H$_{74}$O$_{19}$Na [M+Na]$^+$: 1013.5. found 1013.5.

Example 7'

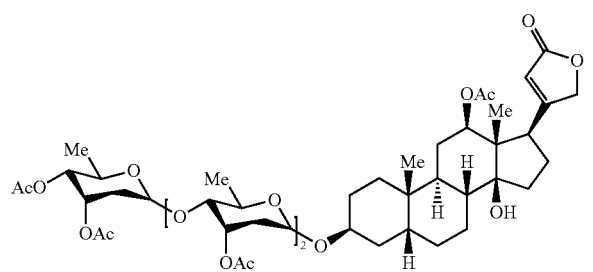

Compound 21

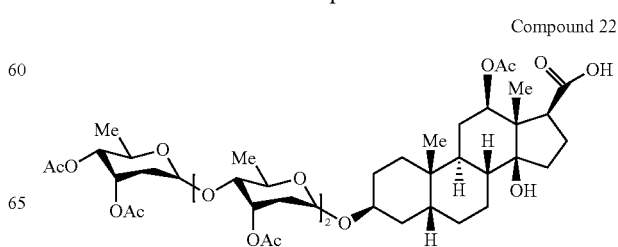

Compound 22

Compound 22.

Potassium permanganate (37.8 mg, 239 μmol, 3 equiv) was added to a solution of Compound 21 (77.3 mg, 78.0 μmol, 1.0 equiv). The solution was stirred at room temperature for 3 d and concentrated in vacuo. The crude material was dry-loaded onto silica gel and purified by flash chromatography on silica gel (2→5→10% methanol in dichloromethane) and azeotroped from heptane to afford Compound 22 (34.5 mg, 36.2 μmol, 46% yield) as a white solid.

$R_f$=0.21 (9:1 dichloromethane/methanol); $^1$H NMR (500 MHz, CDCl$_3$): δ 5.42 (app q, J=3.2 Hz, 1H), 5.38 (app q, J=3.7 Hz, 1H), 5.35 (app q, J=3.5 Hz, 1H), 4.79 (d, J=8.4 Hz, 1H), 4.72 (d, J=10.0 Hz, 1H), 4.69 (d, J=10.2 Hz, 1H), 4.55 (br s, 1H), 4.52 (dd, J=9.8, 3.3 Hz, 1H), 3.99 (br s, 1H), 3.89-3.80 (comp m, 3H), 3.31 (dd, J=9.7, 3.4 Hz, 1H), 3.28 (dd, J=9.8, 3.3 Hz, 1H), 2.81 (br s, 1H), 2.10 (br s, 12H), 1.99 (s, 3H), 2.02-1.98 (comp m, 4H), 1.86-1.38 (comp m, 15H), 1.25-1.20 (m, 9H), 1.14 (d, J=6.1 Hz, 3H), 1.09 (br s, 3H), 0.94 (s, 3H); LRMS (ESI+) m/z calc'd for $C_{48}H_{72}O_{19}Na$ [M+Na]$^+$: 975.5. found 975.5.

Example 8'

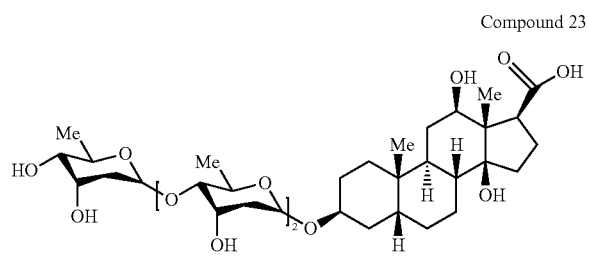

Compound 23

Compound 23.

A solution of sodium methoxide (120 μL of a 0.5 M solution in methanol, 60 μmol, 6 equiv) was added to a solution of Compound 22 (9.6 mg, 10 μmol, 1.0 equiv) in methanol (500 μL, 20 mM). The reaction tube was sealed and warmed to 60° C. in an oil bath. The reaction was cooled to room temperature after 18 h and concentrated in vacuo. The crude material was purified by flash chromatography on silica gel (19:1→9:1 dichloromethane/methanol+5% acetic acid) and azeotroped with heptane to afford Compound 23 (5.8 mg, 7.8 μmol, 78% yield) as an off-white solid.

$R_f$=0.32 (9:1 dichloromethane/methanol+5% acetic acid); (500 MHz, CD$_3$OD): δ 4.94-4.88 (comp m, 31-1), 4.25-4.23 (m, 2H), 4.01-4.00 (m, 2H), 3.86-3.75 (comp m, 3H), 3.25-3.14 (comp m, 5H), 2.06-1.94 (comp m, 25H), 1.33-1.29 (comp m, 7H), 1.25-1.20 (comp m, 9H), 1.00 (br s, 3H), 0.96 (s, 3H); LRMS (ESI+) m/z calc'd for $C_{38}H_{62}O_{14}Na$ [M+Na]$^+$: 765.4. found 765.4.

Example 9'

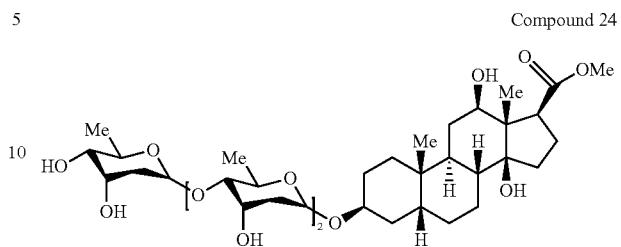

Compound 24

Compound 24.

(Trimethylsilyl)diazomethane (35 μL of a 2 M solution in Et$_2$O, 70 μmol, 21 equiv) was added to a solution of Compound 23 (2.5 mg, 3.4 μmol, 1.0 equiv) in methanol (140 μL) and benzene (540 μL, 1:4 ratio, 5 mM). Additional (trimethylsilyl)diazomethane (50 μL, 100 μmol) was added after 4.5 h. After an additional 2 h, the yellow reaction was quenched with 2 drops of acetic acid and stirred until the suspension turned colorless, and was then concentrated in vacuo. The crude material was purified by flash chromatography on silica gel (5→7% methanol in dichloromethane) to afford Compound 24 (1.6 mg, 2.1 μmol, 62% yield) as a pale yellow oil/film.

$R_f$=0.15 (19:1 dichloromethane/methanol); $^1$H (500 MHz, CD$_3$OD): δ 4.93-4.86 (comp m, 3H), 4.25-4.24 (m, 2H), 4.01-4.00 (m, 2H), 3.86-3.76 (comp m, 3H), 3.68 (s, 3H), 3.26-3.14 (comp m, 5H), 2.14-1.45 (comp m, 22H), 1.24 (d, J=6.3 Hz, 3H), 1.22 (d, J=6.3 Hz, 3H), 1.20 (d, J=6.3 Hz, 3H), 0.95 (s, 3H), 0.88 (s, 3H).

Example 10'

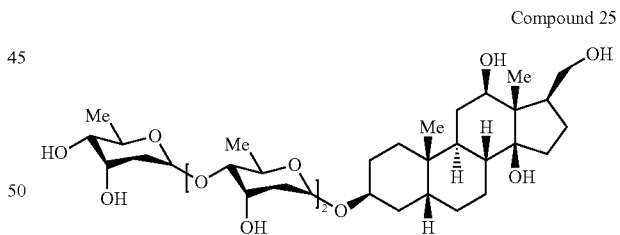

Compound 25

Compound 25.

Lithium aluminum hydride (1.2 mg, 31 μmol, 12 equiv) was added to a suspension of Compound 24 (1.9 mg, 2.6 μmol, 1.0 equiv) and gas evolution was observed. The reaction tube was sealed and the contents were warmed to 90° C. in an oil bath. Additional lithium aluminum hydride (1.2 mg, 31 μmol, 12 equiv) was added after 18 h and the reaction was warmed back to 90° C. The reaction was cooled to room temperature after another 24 h, diluted with ethyl acetate and quenched with excess Na$_2$SO$_4$.10H$_2$O (gas evolution observed). After stirring over night at room temperature, the gray precipitate was filtered through a plug of Celite, washing with ethyl acetate, and concentrated in vacuo. The crude material was purified by flash chromatography on silica gel (9:1 dichloromethane/methanol) to afford Compound 25 (1.3 mg, 1.8 μmol, 69% yield) as a white film.

$R_f$=0.18 (9:1 dichloromethane/methanol); $^1$H (500 MHz, CD$_3$OD): δ 4.93 (comp m, 3H), 4.25-4.24 (m, 2H), 4.01-4.00 (m, 2H), 3.86-3.75 (comp m, 3H), 3.67-3.45 (comp m, 6H), 3.23 (dt, J=9.8, 2.9 Hz, 2H), 3.15 (dd, J=6.3, 3.4 Hz, 1H), 2.37-2.33 (m, 1H), 2.03-1.43 (comp m, 26H), 1.24 (d, J=6.3 Hz, 3H), 1.22 (d, J=5.9 Hz, 3H), 1.20 (d, J=6.2 Hz, 3H), 0.96 (s, 31-1), 0.90 (s, 3H); LRMS (ESI+) m/z calc'd for C$_{38}$H$_{64}$O$_{13}$Na [M+Na]$^+$: 751.4. found 751.6.

Exemplary Compounds of the Invention

The following compounds, as exemplified in Table 1, have been purchased or can be prepared according to the general synthetic methods known to one skilled in the art of organic synthesis. These compounds are or can be tested for their inhibitory activity.

TABLE 1

Exemplary Compounds of the Invention

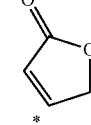

| ID | R$^{1a}$ and R$^{1b}$ | n | Y |
|---|---|---|---|
| 1 | R$^{1a}$=R$^{1b}$=OH | 2 | 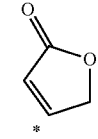 |
| 2 | R$^{1a}$=R$^{1b}$=OH | 1 | 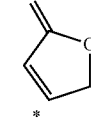 |
| 3 | R$^{1a}$=R$^{1b}$=OH | 0 | 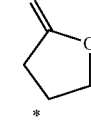 |
| 4 | R$^{1a}$=R$^{1b}$=OH | 2 | 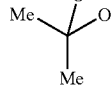 |
| 5 | 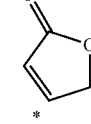 | 2 | 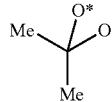 |
| 6 | 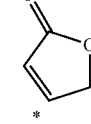 | 2 | 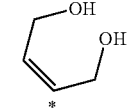 |

TABLE 1-continued

Exemplary Compounds of the Invention

[Structure III: Steroidal glycoside core with R$^{1a}$, R$^{1b}$ substituents on sugar, repeat unit n, and Y group at 17β position; 12β-OH, 14-OH, Me groups, and stereochemistry as shown]

| ID | R$^{1a}$ and R$^{1b}$ | n | Y |
|---|---|---|---|
| 7 | Me, Me (acetonide, O*, O*) | 2 | butenolide (γ-butyrolactone, 2-oxo) |
| 8 | Me, Me (acetonide, O*, O*) | 2 | -CH(OH)CH$_2$CH$_2$CH$_2$OH (diol chain) |
| 9 | Ph, H (benzylidene, O*, O*) | 2 | butenolide (2-furanone) |
| 10 | Ph, H (benzylidene, O*, O*) | 2 | -CH(OH)CH=CHCH$_2$OH (cis-enediol) |
| 11 | Ph, H (benzylidene, O*, O*) | 2 | γ-butyrolactone (2-oxo tetrahydrofuran) |
| 12 | Ph, H (benzylidene, O*, O*) | 2 | -CH(OH)CH$_2$CH$_2$CH$_2$OH (diol chain) |
| 13@ | R$^{1a}$=R$^{1b}$=OH | 2 | -CH(OH)CH$_2$CH$_2$CH$_2$OH (diol chain) |
| 14 | R$^{1a}$=R$^{1b}$=OAc | 2 | butenolide (2-furanone) |

TABLE 1-continued

Exemplary Compounds of the Invention

| ID | R$^{1a}$ and R$^{1b}$ | n | Y |
|---|---|---|---|
| 15@@ | R$^{1a}$=R$^{1b}$=OH | 2 | (2-hydroxyphenyl)methylene-furan-2(5H)-one |
| 16 | Me-CH(O*)(O*) | 2 | (2-hydroxyphenyl)methylene-furan-2(5H)-one |
| 17 | Ph-CH(O*)(O*) | 2 | (2-hydroxyphenyl)methylene-furan-2(5H)-one |
| 18 | R$^{1a}$=R$^{1b}$=OH | 2 | 5-(2-hydroxybenzyl)furan-2(5H)-one |
| 19 | R$^{1a}$=R$^{1b}$=OH | 2 | 5-(2-hydroxybenzyl)dihydrofuran-2(3H)-one |
| 20 | R$^{1a}$=R$^{1b}$=OH | 2 | 5-(2-hydroxybenzyl)-2-hydroxytetrahydrofuran |

TABLE 1-continued

Exemplary Compounds of the Invention

| ID | R$^{1a}$ and R$^{1b}$ | n | Y |
|----|------------------------|---|---|
| 21 | R$^{1a}$=R$^{1b}$=OAc (10-OAc) | 2 | 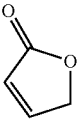 |
| 22 | R$^{1a}$=R$^{1b}$=OAc (10-OAc) | 2 | CO$_2$H |
| 23 | R$^{1a}$=R$^{1b}$=OAc | 2 | CO$_2$H |
| 24 | R$^{1a}$=R$^{1b}$=OH | 2 | CO$_2$Me |
| 25 | R$^{1a}$=R$^{1b}$=OH | 2 | CH$_2$OH |

@Dig(dhd)~80% Th17 inhibition at 40 uM,
@@Dig(sal)~70% Th17 inhibition at 10 uM,
*denotes the attachment point

Assay Methods

In Vitro Human T Cell Culture

Blood samples were obtained from the New York Blood Center. Mononuclear cells were prepared from buffy coats from healthy adult donors or from cord blood, using Ficol-IPAQUE gradients. CD4$^+$ T cells were magnetically selected (autoMACS, Miltenyi). Adult memory CD4$^+$ T cell subsets were further purified as CD3$^+$CD4$^+$CD25$^-$ CD45RO$^+$ CCR6$^+$CD161$^+$ by cell sorting on a FACSAria (BD). Naive CD4$^+$ T cells were isolated from cord blood as CD3$^+$CD4$^+$ CD45RA$^+$HLA-DR$^-$CD25$^-$DAPI$^-$. Memory cells were activated with anti-CD3/CD28 coated beads (1 bead/cell) in T cell media (see above) supplemented with 100 U/mL IL-2 (Peprotech), 10 ng/mL IL-1b and 10 ng/mL IL-23 (eBioscience). Naive cells were activated with anti-CD3/CD28 beads and cultured with the same cytokines, and TGF-b (0, 0.1, 1, or, 10 ng/mL) (Peprotech), in XVIVO-20 (Lonza) media. Viral supernatants were produced by transient transfection of HEK293T cells with HDVIRESGFP or HDVI-RESHSA vectors, a VSV-G expression plasmid and the packaging plasmid pCMVR8.9. Naive CD4$^+$ T cells, cultured in XVIVO-20 media supplemented 100 U/mL IL-2 (Peprotech), were transduced with RORad-IRES-GFP or RORγt-IRES-GFP on day 1 and analyzed on day 6. GFP expressing cells were gated for analysis. DMSO or compounds were added 6-8 hours after the viral transduction. For flow cytometry, the following human specific antibodies were used: CCR6-biotin (11A9 BD), CD3-Alexa750Cy7 (UCHT1 eBioscience), CD4-PacBlue (OKT4 eBioscience), CD25-APC (555434 BD), CD45RA-PE (HI100 eBioscience), CD45RO-APC (UCHL1 eBioscience), IL-17a-APC (eBio64CAP17 eBioscience), IFN-γ-PECy7 (45.B3 eBioscience), HLA-DR-FITC (555558 BD), CD3 purified (UCHT1 eBioscience), and CD28 purified (CD28.2 eBioscience).

Development of a High-Throughput Screening Assay

Methods:

The *Drosophila* S2 cell line was originally purchased from Invitrogen and was maintained in Schneider's medium supplemented with 10% heat-inactivated bovine fetal calf serum and antibiotics (Invitrogen). Gal4 DNA binding domain (G4 DBD) corresponding to amino acids 1 through 147 of Gal4 protein was PCR amplified to make a fusion construct with mouse RORγt (amino acids 79 to the carboxyl terminal end) lacking its DNA binding domain. The resulting chimeric gene was subcloned into the copper inducible pMT/V5-His A vector (Invitrogen). In a similar manner, Gal4 fusion constructs were prepared with mouse RORα (amino acids 142 to end) or *Drosophila* DHR3 (amino acids 120 to end). Coding sequences for firefly luciferase (Promega) were PCR amplified and subcloned into pUAST vector containing Gal4 binding enhancer sequences. Renilla luciferase construct under the polIII promoter was obtained from Dr. Dasgupta's laboratory (NYU medical center). In order to generate stable cell lines, cells were co-transfected with pMT-G4 DBD-RORγt, pMT-G4 DBD-RORα, pMT-G4 DBD-DHR3, or pMT-G4 DBDVP16 and pHygro plasmids (Invitrogen) and screened for resistant colonies in the presence of hygromycin (0.3 mg/mL). More than 150 independent RORγ stable clones with luciferase reporters (pMt-RORγ_luc) were tested for their suitability for the high-throughput screening (HTS) based on the following criteria:

high signal-to background ratio in 384- and 1,536-well plates, their high induction rate upon the addition of copper, and RORγ/γt specificity probed by the dsRORγ- or RORγ/γt antagonist-mediated suppression. Positive clones were further transfected with pUAST-firefly luciferase, polIII-Renilla luciferase, and pCoPuro (Iwaki, Figuera et al. 2003) ("Rapid selection of *Drosophila* S2 cells with the puromycin resistance gene." *Biotechniques* 35(3): 482-4, 486.) and selected with puromycin (2.5 ug/ml). Seven clones were finally selected, and one of them (stable clone #25) was subsequently used for large-scale HTS. Using similar methods, stable clones with genomic integration of the luciferase reporters and other reporters were generated such as pMT-RORα_luc, pMT-DHR3_Luc, or pMT-VP16_luc.

Results and Discussion:

An activity-based assay system that permits high-throughput screening (HTS) for chemical modulators of RORγt transcriptional activity was developed. Since RORγt is located exclusively in cell nuclei, even when mutations are introduced in the putative ligand binding pocket, RORγt-dependent transcriptional activation, rather than the often used ligand-induced cytoplasm to nucleus translocation of hormone receptor, served as a better read-out. A cell-based assay was used to eliminate cell-impermeable or toxic molecules and to perform screening in a biologically relevant setting. The system employed provided a high signal-to-noise ratio and was able to handle a large-scale screen, as well as be cost-effective. S2 cells were derived from late stage *Drosophila melanogaster* embryos with hemocyte-like morphology and gene expression profiles (Schneider, I. *J Embryol Exp Morphol*, 1972, 27, 353-65). They grew at room temperature as a semi-adherent monolayer with no requirement for $CO_2$, making it easy to apply large sets of small chemical molecules and to transfer cells without trypsin treatment.

Like other hormone receptors, RORγt contains both a DNA binding domain (DBD) and a ligand binding domain (LBD). The DBD was replaced with the heterologous yeast GAL4 DBD, because the endogenous DNA binding sites for RORγt are less well characterized.

The GAL4-RORγt fusion construct was placed under the control of a copper inducible promoter, and stable S2 cell lines with genomic integration of this construct were generated. The copper inducible promoter ensures a tight regulation of GAL4-RORγt expression and allows small molecules to get into the cells prior to its induction, thus increasing their effects on GAL4-RORγt. The reporter cells also carried the firefly luciferase reporter, whose expression is regulated by five copies of the GAL4 binding site enhancer (UAS) and a constitutive heat shock promoter, along with a control plasmid, pol III-driven Renilla luciferase. Pol III-Renilla luciferase was previously shown to serve as an excellent transfection and cell viability control in the S2 cell system. Use of Pol III-Renilla luciferase permitted normalization of RORγt-driven firefly luciferase activity and reduced cytotoxic effects and corrected for potential imprecise dispensation of cells in culture medium (Armknecht, S. et al. *Methods Enzymol*, 2005, 392, 55-73). When $Cu^{++}$ was added, the ratio of firefly to Renilla luciferase activity (FR ratio) in these cells increased more than 100-fold compared to control cells lacking GAL4-RORγt (~34 fold increase compared to GAL4-RORγt cells treated with dsROR). RORγt induces robust transcriptional activation in *Drosophila* S2 cells in 384-well plates. For test with transient transfection, firefly reporter under GAL4 binding sites and Pol III-Renilla control plasmids were transiently transfected along with dsRNA (75 ng), targeting EYFP or RORγ, into both control or pMT-GAL4-RORγt stable S2 cell lines (10,000 cells/well). After three days, copper was added to induce GAL4-RORγt, and dual luciferase activity was measured following overnight incubation. The increase was also observed when the experiment was carried out in 384-well plates, demonstrating that it can be adopted as a high-throughput screen. Co-transfecting dsRNA that targets RORγt suppressed ROR-mediated firefly luciferase induction, demonstrating that this activity is ROR dependent.

In order to confirm that the RORγt function in S2 cells was physiologically relevant, it was first confirmed that *Drosophila* has a RORγt homologue. Mouse encodes three different ROR proteins, RORα, RORβ and RORγ. RORγ and RORγt are two isoforms that differ in non-translated N-terminal mRNA sequences. Indeed, *Drosophila* has one ROR homologue, *Drosophila* hormone receptor 3(DHR3) (King-Jones, K. & Thummel, C. S, *Nat Rev Genet*, 2005, 6, 311-23). Structure-based alignment using BLAST revealed 48% amino acid identity between DHR3 and RORγt.

Next it was confirmed that RORγt ligands are likely present in *Drosophila* S2 cells. Since many ligands for nuclear hormone receptors are found to be sterols or their derivatives, growth of cells in medium lacking FBS (fetal bovine serum) or medium supplemented with fatty-acid stripped serum (charcoal treated) was attempted. Only a small decrease of the FR ratio was detected in cells grown in this condition, and the results were not conclusive. Previous studies have shown that the introduction of a single amino acid change inside the ligand binding pocket of RORβ abrogates its function as a transcriptional activator, suggesting that RORβ is a ligand-dependent hormone receptor. The crystal structure of the protein strongly suggested that replacement of alanine 269 with amino acids carrying bulkier side chains, such as valine and phenylalanine, would prevent binding of endogenous ligands without affecting the correct folding of the ligand binding domain (Stehlin, C. et al. *Embo J*, 2001, 20, 5822-31). When the corresponding alanine residue in the putative ligand binding pocket of RORγt was replaced with phenylalanine, the mutant protein was no longer sufficient to induce Th17 cell differentiation when transduced into naive mouse CD4+ T cells, consistent with the presence of cognate RORγt ligand(s) in these cells. The Ala to Phe mutation in RORγt also completely abrogated transcriptional activation of firefly luciferase expression without affecting the transcription of control Renilla luciferase, suggesting that RORγt ligand is present in the *Drosophila* assay system. Indeed, introduction of alanine to phenylalanine (F) mutation in a putative ligand binding pocket abolishes activity of RORγt in this system. As confirmed by immunoblot, the alanine to phenylalanine mutation did not, however, affect protein stability.

DHR3 is transcriptionally regulated by 20-hydroxyecdysone (20E) and is essential for fly larval development (King-Jones, supra). It has been shown that E75, another 20E-dependent fly nuclear hormone receptor, negatively regulates the function of DHR3 (White, K. P., Hurban, P., Watanabe, T. & Hogness, D. S. *Science*, 1997, 276, 114-17; Reinking, J. et al. *Cell*, 2005, 122, 195-207. Indeed, co-expression of E75a or E75b (two *Drosophila* E75 isoforms) decreased the level of DHR3-mediated transcriptional activation in a dosage-dependent manner. E75 is a hormone receptor having antagonizing activities of DHR3 and RORγt. Transfection of increased amount of E75a or E75b resulted in concomitant reduction of FR ratio. Each well received the same amount of DNA in transfection mix. These fly genes also function as dosage-dependent negative regulators for mouse RORγt activity in S2 cells, without affecting the functions of an irrelevant transcriptional activator VP16, strongly suggesting that the ROR/DHR3 core regulatory mechanism is conserved between mouse and fly systems. Collectively, these data confirm the accuracy and relevance of the above approach utilizing the heterologous S2 cell system in order to identify chemical agonists or antagonists of the mouse hormone receptor RORγt.

Activity and Toxicity of the Representative Compounds of the Invention

The following representative compounds are tested for their RORγt inhibitory activity and toxicity. The compounds and their data are given in Table 2, below.

$IC_{50}$ obtained from the S2 cell RORγt reporter
++++ compound exhibited $IC_{50}$<1 μM
+++ compound exhibited $IC_{50}$ 1-10 μM
++ compound exhibited $IC_{50}$ 11-20 μM
+ compound exhibited $IC_{50}$>20 μM
Toxicity assayed with human embryonic kidney 293t cell lines
xxxx cytotoxicity under <1 μM
xxx cytotoxicity between 1-10 μM
xx cytotoxicity between 11-20 μM
x cytotoxicity between 20-40 μM
- no cytotoxicity observed up to 40 μM

TABLE 2

Activity and Toxicity of the Representative Compounds of the Invention

| Compounds ID | $IC_{50}$ | Human cell toxicity | Note |
|---|---|---|---|
| Digoxin | +++ | xxxx | |
| 13 | ++ | — | |
| 15 | ++++ | x | precipitate at high concentration |
| 18 | ++++ | xxx | |
| 19 | +++ | xxx | |
| 20 | + | — | |
| 21 | + | ND | |
| 22 | + | ND | |

TABLE 2-continued

Activity and Toxicity of the Representative Compounds of the Invention

| Compounds ID | $IC_{50}$ | Human cell toxicity | Note |
|---|---|---|---|
| 23 | + | — | |
| 24 | +++ | — | |
| 25 | ++ | x | |

Measurement of Luciferase Activity.

Methods:

Promega Dual-Glo system is widely used for HTS as the luciferase substrates. Cell culture medium was reduced to the final volume of 10 μl or less and 10 μl of Dual-glo and 10 μl of Stop-glo luciferase substrates were added in a sequencial manner (Promega). Firefly and Renilla luciferase activity was determined by measuring luminescence signals using an automated 384-well plate reader equipped with multiple stack units (such as the Analyst GT or Envision plate readers).

Results and Discussion:

The Dual-Glo luciferase assay system from Promega facilitated measuring luciferase activity in HTS. First, it did not require a washing step, and the luciferase activities of both the firefly and the Renilla could be measured in the same well one after the other. Second, the signals that it produced remained stable for more than two hours, making it possible to measure activity from many different plates for a given experiment. Since the reagents are expensive, the volume of medium was reduced to one third prior to adding luciferase substrates, so that fewer substrates were used. However, when minimizing cost is less of a priority, the luciferase substrates used in the primary assay may be directly added to cells without going through this additional step.

HTS for Identification of RORγ/γt Antagonists Using RORγ/γt-luc Stable Cell Lines Methods:

600 G4 DBD-RORγ/γt-luc reporter (#25) or G4 DBD-VP16-luc reporter cells were distributed into each well of 1,536-well white bottom plates in 4 μl S2 cell culture volume containing hygromicin (300 μg/ml) and puromycin (2 μg/ml). Small compounds in seven different concentrations range from 46 μM to 1.7 nM were pin-transferred (23 nl) by a robot (Inglese et al., 2006, Proc. Natl. Acad. Sci. 103:11473-8). After one-hour incubation, 1 μl of culture medium solution containing copper sulfate (to final 0.7 mM) and 10 μM RORγ/γt antagonists were added to each well. After 20-hour incubation at ambient temperature, 1.5 firefly luciferase detection mix was added and the luciferase activities were measured in 10 min. ViewLux luminometers were used for measuring luciferase signal.

Results and Discussion:

Even though G4BD-RORγt stable cells with transient transfection of two luciferase constructs were successfully used for small-scale screening and led the present inventors to identify specific RORγ/γt antagonists in Harvard LCCB, it became problematic to apply the same method to larger scale screens with chemical libraries covering more than 250,000 compounds. First, transient transfection method often produced well-to-well variation due to incomplete mixing and unequal distribution of transfection mix. There is also day-to-day variation when preparing the master transfection mix. Second, in order to save reagent and to handle large quantities of chemicals, it was necessary to do the screen with reduced numbers of cells in a smaller culture volume. Moreover, performing the screen with 1,536-well plates is more efficient than performing the screen with 384-well plates. Thus, new RORγ/γt-luc reporter stable cells were developed to eliminate the necessity of repeated transfection and to achieve increased well-to-well consistency. When tested in a 384-well plate, even small numbers of cells (400 cells/well) gave high firefly luciferase signal (thus high RORγ/γt activity), which is suppressed (22-fold reduction when 400 cells are used) by addition of a RORγ/γt antagonist. The new stable cell line systems also turned out to be suitable for HTS in 1,536-well plates, because z' value is 0.75 when 600 cells are used per well with 10 μl total cell culture volume.

Using RORγ/γt-luc reporter lines, the pilot screen with the LOPAC (Sigma) library was performed through a NIH roadmap program to identify RORγ/γt antagonist compounds. LOPAC contains 1,280 pharmacologically active compounds. Among these, approximately 40 compounds were found as initial hits (~0.3%). These hits were tested against validation screens to identify RORγ/γt specific compounds. To facilitate a large-scale validation, VP16-luc reporter cell lines with genomic integrations of G4BD-VP16, UASt-ffluc, and polIII-Rluc were developed as discussed earlier. These cells also exhibited robust and consistent VP16 activity in 1,536-well plates (data not shown), and thus can be used as a good control reporter to weed-out compounds inhibiting general transcription, the function of GAL4 DNA binding domain, and a nuclear import of GAL4 chimeric proteins. Indeed, many compounds were identified as initial hits to reduce RORγ/γt activity from the pilot LOPAC screen, but later were found to be non-specific inhibitors, because they reduced both RORγ/γt and VP16 activities. Intriguingly, previously identified RORγ/γt specific antagonists identified by small scale HTS, also selectively inhibited RORγ/γt activity without affecting VP16, confirming their specificity on RORγ/γt. A large-scale screen covering more than 250,000 compounds was carried out against RORγ/γt-luc and VP16-luc reporter systems in parallel to identify RORγ/γt specific antagonists in a systematic manner.

Methods Summary for Example 3

Chemical Screen 10,000 *Drosophila* stable S2 cells with genomic integration of the Cu2+-inducible G4 DBD-mouse RORγ construct were transfected with 5 ng of pUASTfirefly luciferase and 7 ng of Pol III-Renilla luciferase and dispensed into white bottom-tissue culture 384-well plates (Corning). Two days later, small compounds (total 4,812 compounds from the ICCB chemical libraries, including Bioactives and Prestwick collections) were added and, after 6 hours, Cu2+ was added to the wells (700 μM). The following morning, Stop-glo luciferase substrates (Promega) were used to measure luciferase activity. Initial hits including digoxin were tested against three different control S2 reporter cell lines.

Cell Culture.

Mouse and human CD4+ T cell culture and viral transduction were performed as described previously [Ivanov et al. *Cell* 126, 1121-1133 (2006); Manel et al. *Nat Immunol* 9, 641-649 (2008)], unless indicated otherwise herein.

Synthesis of Non-Toxic Digoxin Derivatives.

Various digoxin derivatives were synthesized and first tested for toxicity on human embryonic kidney 293T cells at various concentrations. Compounds exhibiting reduced toxicity compared to digoxin were further tested for their RORγ inhibitory activities with the insect cell reporter lines.

General.

All DNA constructs were generated by PCR-based methodology and confirmed by sequencing. Retroviral production and transduction, EAE experiments, and gene chip analysis were performed as described previously [Ivanov et al. *Cell* 126, 1121-1133 (2006)]. For the in vitro competition assay, 109 nM RORγ LBD protein and 2 nM Fluorescein-labeled 25-hydroxycholesterol were added to a dilution series of individual chemical compounds. IL-17a, IFN-γ, IL-4, and CCR6 protein expression was examined by intracellular or surface staining according to the manufacturer's protocol.

Secondary assays directed toward evaluating the ability of such compounds to suppress mouse or human Th17 cell differentiation are also encompassed herein. Exemplary secondary assays that serve to confirm bona fide RORγ inhibitors include without limitation:

Secondary Screening Lists

S2 cell reporter system: Identified hits from HTS are further screened and their specificity confirmed by testing against RORγ-luc, VP16-luc, RORα-luc, and DHR3-luc reporter S2 cell lines. Compounds either having no activity on VP16, RORα, and DHR3 or having ten times higher $IC_{50}$ values on such reporters are selected for further tests.

Cytokine induced mouse Th17 cells differentiation: Effects on mouse endogenous RORγt in a relevant physiological setting were determined by testing compounds in the Th17 cell differentiation assay. Compounds having RORγt inhibitory activity are predicted to suppress Th17 cell differentiation. Th1 or regulatory T cell differentiation was used as a counter-screen method to select specific compounds that only affect Th17 cell differentiation without having pleiotrophic effects on general T cell proliferation or cytokine production.

ROR dependent Th17 cell differentiation: Compounds were further tested, by examining their effects on T cells expressing RORα or RORγ. Compounds that directly inhibit RORγ are expected to inhibit RORγ— but not RORα-dependent Th17 cell differentiation. Compounds affecting IL17a production or ROR regulatory pathways, however, are expected to inhibit both.

Human Th17 cell differentiation: Compound effects on human RORγt were tested by treating human cord blood CD4 T cells with select compounds to determine if such compounds alter differentiation into Th17 lineages.

Assessment of induction, expression and/or release of a pro-inflammatory cytokine or a pro-inflammatory cytokine receptor and/or a pro-inflammatory chemokine or a pro-inflammatory chemokine receptor in a cell comprising contacting the cell with a compound as described herein or a pharmaceutically acceptable salt thereof or a composition thereof and determining results of said contacting. In some embodiments, the contacting inhibits the induction, expression and/or release of a pro-inflammatory cytokine or a pro-inflammatory cytokine receptor and/or a pro-inflammatory chemokine or a pro-inflammatory chemokine receptor. In certain embodiments, the inhibiting occurs in vitro. In alternate embodiments, the inhibiting occurs in vivo, for example, in a mammal, such as a human. Accordingly, in some embodiments, the present invention provides for a method for modulating the induction, expression and/or release of a pro-inflammatory cytokine or a pro-inflammatory cytokine receptor and/or a pro-inflammatory chemokine or a pro-inflammatory chemokine receptor in a mammal comprising administering to said mammal a compound, a pharmaceutically acceptable salt thereof, or a composition thereof as described herein. In certain embodiments, the pro-inflammatory cytokine includes, but is not limited to CLCF1, CSF1, CX3CL1, IL3, IL-6, IL-17, IL-17F, IL-21, IL-22, IL-26, LTA, TNF, TNFsf8, TNFsf10, TNFα, or any combination thereof. In certain embodiments, the pro-inflammatory chemokine includes, but is not limited to, CCL6, CCL9, CCL11, CCL19, CCL20, CCL22, CCL24, GM1960, XCL1, or any combination thereof. In certain embodiments, the pro-inflammatory cytokine receptor includes, but is not limited to, IL-23R, IL-1RI, IL-1RII, Cysltr1, Ltb4r1, IL-7Re, or any combination thereof. In certain embodiments, the pro-inflammatory chemokine receptor includes, but is not limited to, CCR1, CCR2, CCR6, CCR9, CXCR7, GPR43, or any combination thereof.

Additional Methodological Details

As detailed herein, in order to identify small molecules to antagonize RORγ/γt transcriptional activity, the present inventors developed insect cell line based reporter systems, expressing murine RORγ/γt or closely related transcriptional activators. Since their cognate DNA binding sites were not well characterized, the DNA binding domains (DBD) of RORγ/γt, RORα (mouse homolog for POPγ), and DHR3 (Drosophila orthologue for ROR family proteins) were replaced with the heterologous yeast GAL4 DBD. The transcriptionally active domain of general transcriptional activator VP16 was also fused with GAL4 DBD. The GAL4 fusion constructs were placed under the control of a copper inducible promoter, and stable S2 cell lines with genomic integration of these four reporter constructs were generated. The copper inducible promoter ensures tight regulation of GAL4-fusion protein expression and it allows small molecules to get into the cells prior to protein induction, thus increasing their effects on GAL4 reporters. The stable reporter cell lines also encode the firefly luciferase reporter, whose expression is regulated by five copies of the GAL4 binding site enhancer (UAS), along with the pol III-driven Renilla luciferase reporter. Pol III-Renilla luciferase was included to serve as cell viability control in the S2 cell system (Armknecht, S. et al. *Methods Enzymol* 392, 55-73 (2005).

In vitro mouse Th17 cell polarization assay may also be utilized as follows.

Methods:

Cell Purification.

Cells from lymph nodes and spleens derived from six to eight week old B6 mice (Taconic) can be used for T cell purification. B220⁻ cells can be isolated on an autoMACS Pro with bead depletion of B220⁺ cells (Miltenyi). Naive CD4⁺ T cells can be further purified as TCRb⁺CD8⁻ DAPI⁻ CD19⁻ CD4⁺CD25⁻ CD62L⁺CD44$^{low/int}$ by cell sorting on a FACSAria (BD).

Cell culture and T cell polarization may also be utilized for assaying compounds described herein. Accordingly, T cells can be cultivated in an incubator at 37° C. and 5% $CO_2$ in RPMI 1640 medium (Invitrogen) supplemented with 10% (vol/vol) heat-inactivated FBS (Hyclone), penicillin-streptomycin, 2 mM glutamine and 0.1 mM nonessential amino acids. Cells can be seeded on day 0 at a density of $0.4\times10^5$ cells per ml in 96-well plates coated with anti-CD3e (5 ug/ml) and anti-CD28 (10 ug/ml). Cells can be cultured for 4-5 days in Th17 inducing (TGFβ (0.3 ng/ml), IL6 (20 ng/ml), IL1β (10 ng/ml), anti-IFN-γ, and anti-IL4) conditions. At day 1, compounds dissolved in DMSO can be added. Cytokines and antibodies can be purchased from Ebioscience, Peprotech, or BD pharmingen.

Surface and intracellular staining can also be used for assaying compounds described herein. For intracellular cytokine staining, cells can be incubated for 5 h with phorbol ester (50 ng/ml; Sigma), ionomycin (500 ng/ml; Sigma) and GolgiStop (BD). When needed, surfaces can be stained by incubation for 15 min on ice with PECy7-conjugated CD4 (BD Biosciences). The Cytofix/Cytoperm buffer set (BD), for example, can be used for intracellular staining. Cells can be fixed and made permeable for 30 min on ice and stained for 30 min on ice in permeabilization buffer with, for example, Alexa647-conjugated anti-IL17 (eBioscience) antibodies. An LSR II (BD Biosciences) and FlowJo software (Tree Star) can be used for flow cytometry.

Testing compounds in in vivo mouse animal disease models. Compounds described herein can be tested for efficacy in various animal disease models (e.g., mouse disease models), including experimental autoimmune encephalomyelitis (EAE), collagen-induced arthritis (CIA), and inflammatory bowel disease (IBD). One approach is to expose ex vivo T cells to the compounds and then test the cells' differentiation potential by transferring them to mice with partially or completely compromised immune systems.

With aspects of the claimed invention now being generally described, these will be more readily understood by reference to the following examples, which are included merely for purposes of illustration of certain features and embodiments of the presently claimed invention and are not intended to be limiting.

Example 3

Detailed Methods

Development of S2 Cell Reporter Cell Lines.

The *Drosophila* S2 cell line was originally purchased from Invitrogen and was maintained in Schneider's *Drosophila* medium supplemented with 10% heat-inactivated bovine fetal calf serum and 1× antibiotic-antimycotic solution (Invitrogen). The Gal4 DNA binding domain (G4 DBD), corresponding to amino acids 1 through 147 of the Gal4 protein, was PCR amplified to make the fusion construct with murine RORγ (amino acids 79 to the carboxyl terminal end) lacking its DNA binding domain. The resulting chimeric gene was subcloned into the copper inducible pMT/V5-His A vector (Invitrogen) and into the constitutive pAc vector. Similar methods yielded fusion constructs between G4 DBD and murine RORα (amino acids 142 to end), *Drosophila* DHR3 (amino acids 120 to end), *C. elegans* Daf12 (amino acids 184 to end), and herpes simplex virus VP16 (amino acids 413 to end). Coding sequences for firefly luciferase (Promega) were PCR amplified and sub-cloned into the pUAST vector containing five Gal4 binding enhancer sequences. The Renilla luciferase construct under a pol III promoter and the pAc vector were obtained from R. Dasgupta (NYU School of Medicine). To generate cell lines stably expressing various chimeric proteins upon copper addition, S2 cells were co-transfected with pMT plasmids encoding individual G4 DBD chimeric constructs and the pCoHygro plasmid (Invitrogen), before screening for resistant colonies in the presence of hygromycin (0.3 mg/mL). Clones with genomic integration of G4 DBD-RORγ, G4 DBD-RORα, G4 DBD-DHR3, and G4 DBD-VP16 were further transfected with pUAST-firefly luciferase, polIII-Renilla luciferase, and pCoPuro [Iwaki et al. BioTechniques, Vol. 35 482-484, 486 (2003)], and resistant clones were selected with puromycin (2.5 μg/mL). The human androgen receptor (hAR) expression plasmid pMK33-hAR and its reporter TAT3-Luc were obtained from M. Garabedian (NYU School of Medicine). Fusion constructs were made between eYFP and wild-type or mutant (A325F) RORγ coding sequences, sub-cloned under the pMT promoter, and used for generating stable S2 cell lines as described above. R1881 (10 nM) and Dafachronic acid (10 μM) were used as ligands for hAR and Daf12. Upon treatment of cells with copper, in 384 well plates, there was specific increase in firefly luciferase activity versus normalized Renilla luciferase activity for all cell lines described above, validating the method for high-throughput screen. Interestingly, unlike RORα and RORγ, the other ROR family member, RORβ, did not transactivate firefly luciferase in *Drosophila* cells, suggesting that the ligand for RORβ is not produced in this system or derived from a precursor in serum.

Chemical Screen.

Transfections of firefly and Renilla reporter constructs were performed using the Effectene kit from Qiagen according to the manufacturer's protocol with some modifications. Briefly, 5 ng of pUAST-firefly luciferase and 7 ng of Pol III-Renilla luciferase were mixed with Enhancer/Effectene reagents in EC buffer (total volume: 6 μL), incubated for 10 to 15 minutes, and then the entire transfection mix was homogenously mixed with the stable G4 DBD-RORγt cell line in Schneider's *Drosophila* medium supplemented with heat inactivated fetal bovine serum, hygromycin, and Pen/Strep antibiotics (Invitrogen). A total volume of 30 μL, containing 6 μL of transfection mix and 10,000 cells was dispensed automatically into white bottom-tissue culture 384-well plates (Corning) with a high-speed, 8-channel microplate dispenser (Wellmate). Two days later, robot-mediated pin-transfer of small compounds (4,812 total compounds from the ICCB-Longwood chemical libraries, including Maybridge5, Bioactives and Prestwick collections) was performed, and after 6 hours, $Cu^{++}$ was added to the wells (700 μM). The following morning, cell culture medium was reduced to the final volume of 10 μL, and 10 μL of Dual-glo and 10 μL of Stop-glo luciferase substrates were sequentially added (Promega). Firefly and Renilla luciferase activities were determined by measuring luminescence signals, using an automated 384-well plate reader (Analyst GT).

*Drosophila*.

Coding sequences for G4 DBD-RORγ (wild-type) or G4 DBD-RORγ (A325F) were sub-cloned into the heat-shock inducible pCaSpeR-hs-act vector (obtained from C. Thummel, University of Utah). The resulting constructs were used to generate transgenic *Drosophila* lines (Rainbow Transgenic Flies, Inc). RORγ (WT) and RORγ (A325F) transgenic flies were crossed to the GAL4 reporter lines UASt-LacZ or UASt-GFP (Bloomington *Drosophila* Stock center) and were later heat-shocked at 37° C. for 30 minutes on three consecutive days. LacZ activity was measured using a beta-gal assay kit (Invitrogen), and GFP signals were analyzed by flow cytometry (BD LSRII).

Mice.

For the conditional targeting of RORγt, we have generated a line, RORγt$^{fl/fl}$, in which exons 3, 4, 5, 6 are flanked by LoxP sites. Cre-mediated recombination results in an out-of-frame mutation, abrogating productive protein translation (Kim and Littman, unpublished data). The IL-23R-GFP reporter line was provided by M. Oukka and V. Kuchroo (Harvard Medical School) [Awasthi et al. *J Immunol* 182, 5904-5908 (2009)].

S2 Cell Culture in Serum-Free Media.

S2 cells were maintained in Express Five SFM media (Invitrogen) and passaged in semi-synthetic (SSM-1) media (Santori et al., unpublished results) in the absence of sterol lipids [Silberkang et al. *J Biol Chem* 258, 8503-8511 (1983)] 4-7 days prior to transfection. $1.5 \times 10^5$ cells/well were plated in 96 well plates and incubated 1 hr at 25° C. After incubation, media was exchanged for 75 µl/well transfection mix. The transfection mix (in SSM-1) included 10 ng of G4 DBD-RORγ (pAc vector), 5 ng of destabilized firefly luciferase (Promega; pUAST), 2 ng of Pol III-Renilla luciferase and 0.5 µl of Cellfectin reagent (Invitrogen) per well. Following 4-5 hrs incubation at 25° C., the SSM-1 media was replaced with fresh media. Various cholesterol metabolites were added 24 hrs later and, after overnight incubation, cell lysate was prepared for analysis with the Dual Luciferase Reporter Kit (Promega). Luciferase activity was measured using the Viktor3 system (Perkin-Elmer).

In vitro Mouse T Cell Culture.

T cells were purified from lymph nodes and spleens of six to eight weeks old B6 mice (Taconic), by magnetically depleting B220$^+$ cells (autoMACS, Miltenyi), and then sorting CD8$^-$DAPI$^-$CD19$^-$CD4$^+$CD25$^-$CD62L$^+$CD44$^{low/Int}$ naive T cells on a FACSAria (BD). Cells were cultivated at 37° C. and 5% $CO_2$ in T cell media: RPMI 1640 (Invitrogen) supplemented with 10% (vol/vol) heat-inactivated FBS (Hyclone), 50 U penicillin-streptomycin (Invitrogen), 2 mM glutamine, and 50 µM β-mercaptoethanol. For T cell polarization, 200 µl cells were seeded at $0.4 \times 10^5$ cells per mL in 96-well plates pre-coated with anti-CD3ε (5 µg/mL) and anti-CD28 (10 µg/mL). Cells were cultured for 4-5 days in Th17 (TGF-β (0.3 ng/mL), IL-6 (20 ng/mL), and anti-IFN-γ and anti-IL-4 (2 ng/mL)), Th1 (IL-12 (10 ng/mL), IL-2 (10 U/mL) and anti-IL-4 (2 ng/mL)), or Th2 (IL-4 (10 ng/mL), and anti-P35 and anti-IFN-γ 2 ng/mL)) conditions. For ectopic expression ROR proteins, native CD4$^+$ T cells were infected with retroviral MIGr-control, MIGr-RORα or MIGr-RORγ 24 hrs after activation, and cultured without exogenous cytokines or only with IL-6. At day 1, compounds dissolved in DMSO were added. For cytokine analysis, cells were incubated for 5 hours with phorbol 12-myristate 13-acetate (50 ng/mL; Sigma), ionomycin (500 ng/mL; Sigma) and GolgiStop (BD). Intracellular cytokine staining was performed according to the manufacturer's protocol (Cytofix/Cytoperm buffer set from BD) with alexa647-conjugated anti-IL-17a (eBioscience), and PE-conjugated anti-IFN-γ or anti-IL-4 (eBioscience). An LSR II (BD Biosciences) and FlowJo software (Tree Star) were used for flow cytometry and analysis. Dead cells were excluded using the Live/Dead fixable aqua dead cell stain kit (Invitrogen).

In Vitro Human T Cell Culture.

Blood samples were obtained from the New York Blood Center. Mononuclear cells were prepared from buffy coats from healthy adult donors or from cord blood, using Ficol-lPAQUE gradients. CD4$^+$ T cells were magnetically selected (autoMACS, Miltenyi). Adult memory CD4+ T cell subsets were further purified as CD3$^+$CD4$^+$CD25$^-$CD45RO$^+$CCR6$^+$ CD161$^+$ by cell sorting on a FACSAria (BD). Naive CD4$^+$ T cells were isolated from cord blood as CD3$^+$CD4$^+$ CD45RA$^+$HLA$^-$DR$^-$CD25$^-$DAPI$^-$. Memory cells were activated with anti-CD3/CD28 coated beads (1 bead/cell) in T cell media (see above) supplemented with 100 U/mL IL-2 (Peprotech), 10 ng/mL IL-1β and 10 ng/mL IL-23 (eBioscience). Naive cells were activated with anti-CD3/CD28 beads and cultured with the same cytokines, and TGF-β (0, 0.1, 1, or, 10 ng/mL) (Peprotech), in XVIVO-20 (Lonza) media. For ectopic expression of ATP1A1, cells were first transduced with a lentiviral GFP vector, HDVIRESGFP, encoding murine ATP1A1 (Origene clone image 4950746). On day 2, cells were transduced with empty HDVIRESHSA vector or ones encoding human RORαd, RORβ or RORγT [Manel et al. *Nat Immunol* 9, 641-649 (2008)], and compounds were added at 10 or 20 µM. On day 6, cells were treated with PMA, ionomycin and GolgiStop, surface stained with anti-HSA-PE, and intracellularly stained with anti-IL-17a-Alexa 647 and anti-IFN-γ-PECy7. Viral supernatants were produced by transient transfection of HEK293T cells with HDVIRESGFP or HDVIRESHSA vectors, a VSV-G expression plasmid and the packaging plasmid pCMVR8.9. Naive CD4+ T cells, cultured in XVIVO-20 media supplemented with 100 U/mL IL-2 (Peprotech), were transduced with RORαd-IRES-GFP or RORγt-IRES-GFP on day 1 and analyzed on day 6. GFP expressing cells were gated for analysis. DMSO or compounds were added 6-8 hours after the viral transduction. For flow cytometry, the following human specific antibodies were used: CCR6-biotin (11A9 BD), CD3-Alexa750Cy7 (UCHT1 eBioscience), CD4-PacBlue (OKT4 eBioscience), CD25-APC (555434 BD), CD45RAPE (HI100 eBioscience), CD45RO-APC (UCHL1 eBioscience), IL-17a-APC (eBio64CAP17 eBioscience), IFN-γ-PECy7 (45.B3 eBioscience), HLA-DR-FITC (555558 BD), CD3 purified (UCHT1 eBioscience), and CD28 purified (CD28.2 eBioscience).

qPCR Analysis.

Complementary DNAs (cDNAs) were synthesized from TRIzol (Invitrogen) isolated RNA, using M-MLV Reverse Transcriptase (Promega). Real-time RT-PCR was performed with SYBRgreen master mix (Roche) and the Roche real-time PCR system (Roche480). Gene specific values were normalized to Actb for each sample. Primer sequences are the following: Actb (TACAGCTTCACCACCACAGC; SEQ ID NO: 1 and TCTCCAGGGAGGAAGAGGAT; SEQ ID NO: 2), IL-17a (CTCCAGAAGGCCCTCAGACTAC; SEQ ID NO: 3 and AGCTTTCCCTCCGCATTGACACAG; SEQ ID NO: 4), RORγt (CCGCTGAGAGGGCTTCAC; SEQ ID NO: 5 and TGCAGGAGTAGGCCACATTACA; SEQ ID NO: 6) and IL-23R (GCCAAGAAGACCATTCCCGA; SEQ ID NO: 7 and TGCAGGAGTAGGCCACATTACA; SEQ ID NO: 8).

Gene Chip Analysis.

RNA was prepared from in vitro cultured and GFP+ sorted T cells as described [Zhou et al. *Nat Immunol* 8, 967-974 (2007)]. For microarray analysis, RNA was labeled and hybridized to GeneChip Mouse Genome 430 2.0 arrays according to Affymetrix protocols. Data were analyzed with GeneSpring GX10 software. Significant genes with p-values smaller than 0.05 and fold changes greater than 2 were selected.

Mouse EAE.

For induction of active EAE, mice were immunized subcutaneously on day 0 with 70 μg MOG 35-55 peptides, emulsified in CFA (CFA supplemented with 200 mg/mL *Mycobacterium tuberculosis*), and injected (IP) on days 0 and 2 with 100 ng/mouse of pertussis toxin (Calbiochem). Alternatively, the MOG$_{35-55}$/CFA Emulsion PTX kit (Hooke Laboratories) was used. The EAE scoring system was as follows: O-no disease, 1-limp tail; 2-weak/partially paralyzed hind legs; 3-completely paralyzed hind legs; 4-complete hind and partial front leg paralysis; 5-complete paralysis/death. For induction of passive EAE, splenocytes derived from MBP transgenic, IFN-γ knock-out mice [Wensky et al. *J Immunol* 174, 1416-1423 (2005)] were cultured under Th17 conditions (T cell media, 20 ng/mL IL-6, 0.9 ng/mL TGF-β, 10 μg/mL anti-IL-4 antibodies). After 4 days, cells were re-stimulated with 10 ng/mL IL-23 and irradiated APCs (3000 rad) from TCRαβ-deficient mice. On day 7, $2\times10^6$ MBP-specific CD4+ T cells were transferred into B10.PL RAG-1 deficient recipients. Non-classical EAE was scored as follows: level 2-head tilt; level 3-ataxia; level 4-uncontrollable rolling; level 5-moribund. DMSO or digoxin (40 μg/mouse) was injected I.P. daily starting on day 2. Body weight and EAE scores were monitored daily.

Histology Protocol.

Animals were purfused with PBS+5 mM EDTA before spinal cord removal. Spinal cords were treated with 10% formalin for 24-48 hours and placed into histology cassettes. Samples were quickly washed 3× with PBS, then with 50% EtOH for 30 min on a shaker. Samples were placed in 70% EtOH until processed by the NYU core histology unit.

In Vitro Binding and Competition Assay.

Human RORγ LBD (residues 262-518), flanked by an N-terminal 6×His-tag and a thrombin cleavage site, was expressed from a pET46 Ek/Lic vector in BL21-CodonPlus (DE3)-RIL *E. coli* cells (Stratagene). The cells were induced with 0.5 mM IPTG at 16° C. overnight, then collected and lysed in 20 mM Tris-HCl (pH 8.0), 500 mM NaCl, 20 mM imidazole and 10% glycerol. Supernatant was loaded onto a HisTrap™ FF crude 5 mL column on an AKTAxpress HPLC system. The protein was eluted with a 20-500 mM imidazole gradient, dialyzed overnight against 20 mM Tris-HCl (pH 8.0) and 200 mM NaCl, and further purified on a Q Sepharose™ Fast Flow anion exchange column (Amersham Biosciences). The flow-through fraction containing pure RORγ LBD protein was collected, and DTT was added to 10 mM immediately after calculating protein concentration by $OD_{280}$. For the binding assay, 2 nM Fluorescein-labeled 25-hydroxycholesterol was incubated with purified RORγ LBD protein for 2 hrs at room temperature. Protein concentration was varied by serial dilution in binding buffer (20 mM Tris-HCl (pH 8.0), 200 mM NaCl, 10 mM DTT). Fluorescent polarization signals were measured with a Beacon 2000 (PanVera). The data were later converted to fluorescent anisotropy values, and the curve was fitted using the equation $A=Af+(Ab-Af)*[Protein]/([Protein]+Kd)$, where Af and Ab are the anisotropy values of the free and bound fluorescein-labeled 25-hydroxycholesterol, respectively, and Kd is the dissociation constant. For competition assays, 109 nM RORγ LBD protein and 2 nM Fluorescein-labeled 25-hydroxycholesterol were added to a dilution series of individual chemical compounds. After 3 hrs at room temperature, the data were recorded and $IC_{50}$ was calculated by GraphPad Prism 5 software using the fitting equation $Y=Bottom+(Top-Bottom)/(1+10^{\wedge}(X-Log\ IC50))$, where X is log molar concentration of the synthetic compound.

Random Mutagenesis.

The ligand binding domain of RORγt in G4 DBD-RORγt was PCR amplified (primers: tgccccagaggtaccatatgc; SEQ ID NO: 9 and tcactttgacagcccctcagg; SEQ ID NO: 10) in error prone conditions using the GeneMorph® II EZClone Domain Mutagenesis kit (Stratagene), and were individually subcloned into the pMT vector. Their transcriptional activities in the presence or absence of 15 μM digoxin were compared, and clones exhibiting ≥20-fold decreases in digoxin inhibition, compared to wild-type RORγ, were selected for the full sequencing and further analysis.

Immunoblot and Histochemistry.

For immunoblot analysis, wild-type or RORγ knockout T cells cultured in Th17 conditions were lysed with cell lysis buffer (20 mM HEPES-KOH/7.6, 150 mM NaCl, 10% glycerol, 1% Triton X-100, 2 mM EDTA, 1× protease inhibitor (Roche) and 1 mM DTT). 20 μg protein was used for the immunoblot analysis with 1:2,000 rabbit anti-RORγt (M. Ciofani and D. R. Littman, unpublished) and 1:1,000 anti-tubulin (The Developmental Studies Hybridoma Bank). For the immunostaining, T cells were plated on 8-well glass slides (Lab-Tek II Chamber Slide System) and fixed for 15 min in 2% paraformaldehyde in PBS. Cells were blocked and permeabilized in PBSt (5% BSA (Sigma) in PBS containing 0.3% Triton X-100) for 30 minutes at room temperature. Cells were then incubated for 12-16 hrs at 4° C. with 1:50 rabbit anti-RORγt. After three washes in PBSt, the cells were incubated for 1 h at room temperature with Cy5-conjugated goat anti-rabbit antibody (Jackson ImmunoResearch Laboratory) (1:500 in PBSt). After 3 washes in PBSt, samples mounted in Vectashield mounting medium supplemented with DAPI (Vector lab). Samples were examined with a Zeiss ZMD510 microscope with a CCD camera, and images were processed with Zeiss LSM Image Browser 4.0 and Adobe Photoshop 7.0.

Induced Animal Model Relating to Intestinal Bowel Diseases.

B6 wild-type mice received 2% DSS (Dextran Sulfate Sodium) ad libitum in drinking water for 7 days. From day 1, mice were IP injected with either DMSO or digoxin (40 mg/mouse) every day. Gut associated cells were collected and activated for cytokine straining on day 7. To isolate cells from the small intestinal lamina propria, Peyer's patches, fat and mesenterium were removed before opening the intestine longitudinally. The tissue was cut into 2 cm pieces and washed in calcium- and magnesium-free PBS (Gibco). The tissue was then washed for 10 minutes in cold 1 mM DTT (Sigma) in PBS then two 10 minute washes in 30 mM EDTA, 10 mM HEPES (Gibco) in PBS at 37° C. The tissue was washed with complete RPMI and digested for 1.5 hr at 37° C. in 5% $CO_2$, humidified atmosphere, in complete RPMI containing 100 U ml-1 type VIII collagenase (Sigma) and 150 μg ml—1 DNaseI (Sigma). After digestion, cells were eluted from the tissue by shaking. Live cells were isolated using a Percoll (Pharmacia) gradient. IL-17a and IFN-γ staining were done as described previously.

Results and Discussion

CD4+ T helper lymphocytes that express interleukin-17 (Th17 cells) have critical roles in mouse models of autoimmunity, and there is mounting evidence that they also influence inflammatory processes in humans. Genome-wide association studies in humans have linked genes involved in Th17 cell differentiation and function with susceptibility to Crohn's disease, rheumatoid arthritis, and psoriasis [Duerr et al. *Science* 314, 1461-1463 (2006); Nair et al. *Nat Genet* 41, 199-204 (2009); Stahl et al. *Nat Genet* 42, 508-514 (2010)]. Thus, the pathway towards differentiation of Th17 cells and, perhaps, of related innate lymphoid cells with similar effector functions [Buonocore et al. *Nature* 464, 1371-1375 (2010); Colonna *Immunity* 31, 15-23 (2009)], is an attractive target for therapeutic applications. Mouse and human Th17 cells are distinguished by expression of the retinoic acid receptor related orphan nuclear receptor RORγt, which is required for induction of IL-17 transcription and for the manifestation of Th17-dependent autoimmune disease in mice [Ivanov et al. *Cell* 126, 1121-1133 (2006)]. By performing a chemical screen with an insect cell-based reporter system, the present inventors identified the cardiac glycoside digoxin as a specific inhibitor of RORγt transcriptional activity. Digoxin inhibited murine Th17 cell differentiation without affecting differentiation of other T cell lineages and was effective in delaying the onset and reducing the severity of autoimmune disease in mice. At high concentrations, digoxin is toxic for human cells, but as shown herein, non-toxic synthetic derivatives, 20,22-dihydrodigoxin-21,23-diol (Dig(dhd)) and digoxin-21-salicylidene (Dig(sal)), specifically inhibited induction of IL-17 in human CD4+ T cells. Using these small molecule compounds, the present inventors demonstrated that RORγt is required for the maintenance of IL-17 expression in mouse and human effector T cells. These data suggest that derivatives of digoxin can be used as therapeutic agents that attenuate inflammatory lymphocyte function and autoimmune disease and, further, as chemical probes for development of additional RORγt-targeted therapeutic agents that attenuate inflammatory lymphocyte function and autoimmune disease.

To identify small molecules that specifically inhibit RORγ transcriptional activity, the present inventors prepared *Drosophila* S2 cells stably expressing fusions of the GAL4 DNA binding domain (DBD) and the ligand binding domains (LBDs) of murine RORγ, RORα (mouse homolog of RORγ), and DHR3 (*Drosophila* orthologue for ROR family proteins), as well as the activation domain of the general transcriptional activator VP16. Expression of RORγ and the other fusion proteins led to robust expression of a firefly luciferase reporter. Next, the present inventors investigated whether RORγ activity in the *Drosophila* system is ligand-dependent. A single amino acid change in the putative ligand binding pocket [Stehlin et al. *Embo J* 20, 5822-5831 (2001)] of RORγ completely abrogated its function as a transcriptional activator despite comparable levels of protein expression both in S2 cells and in transgenic fly models. In addition, *Drosophila* cells grown in serum-free media completely lacked RORγ activity, unless serum or cholesterol metabolites were supplemented into the cell culture, suggesting that as yet unidentified ligands are required for RORγ reporter activity. These data justify utilization of the heterologous system to identify small molecules that modulate RORγ activity.

Figure 1B:
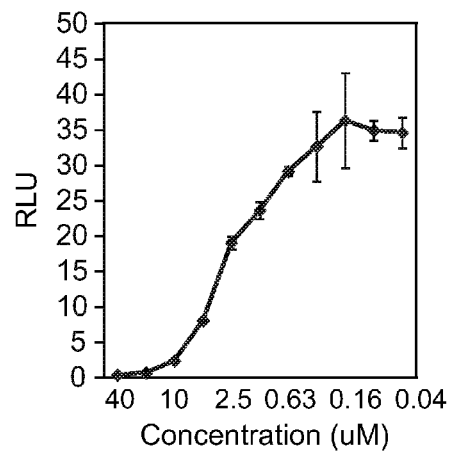
Figure 1C:
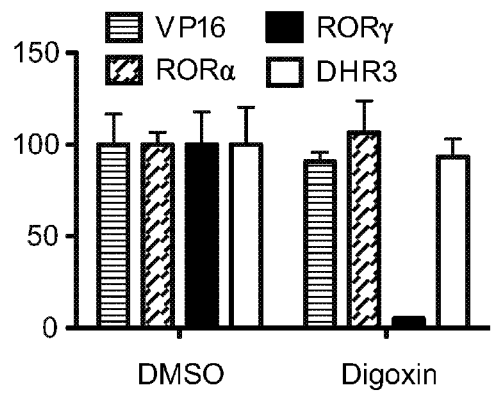
Figure 1D:
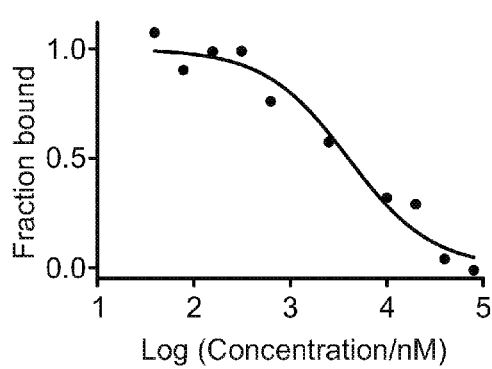

The present inventors next performed a chemical screen with 4,812 compounds and identified digoxin as a specific inhibitor for RORγ transcriptional activity (FIG. 1a). Digoxin inhibited RORγ with an $IC_{50}$ (half-maximal inhibitory concentration) value of 1.98 μM (FIG. 1b). Other cardiac glycosides with structures related to digoxin, including proscillaridin A, deslanoside, erysimoside, oleandrin, ouabain, ouabagenin, digitoxigenin, digoxigenin, and lanatoside C, had no significant effect on RORγ transcriptional activity. Inhibition of RORγ activity by digoxin was specific, as there was no effect on the transcriptional activity of VP16 or of the related nuclear hormone receptors RORα and DHR3 (FIG. 1c). Digoxin did not inhibit the activity of other nuclear hormone receptors, including C. elegans Daf12 and human androgen receptor. Digitoxin and β-acetyldigoxin also selectively inhibited RORγ with similar $IC_{50}$ values. Next, the present inventors examined if digoxin targets RORγ directly. 25-Hydroxycholesterol has been shown to bind to the RORγ LBD [Jin et al. Mol Endocrinol 24, 923-929 (2010)], and conjugation of fluorescein to this surrogate ligand did not affect its ability to bind to human RORγ LBD (with a $K_d$ of 109 nM). Addition of digoxin led to a dose-dependent decrease in fluorescence polarization values, demonstrating that digoxin can displace the sterol ligand by direct binding to RORγ, with an $IC_{50}$ of 4.1 μM (FIG. 1d). The present inventors further investigated whether digoxin binds inside the ligand binding pocket of RORγ by performing random mutagenesis on the LBD and screened 200 clones to identify those that were resistant to digoxin-mediated inhibition. Two clones with this property were identified and shared mutation of amino acid 290 (L290P/A494T and L290F/C318S). RORγ harboring mutations at all three residues exhibited much less sensitivity to digoxin, in spite of transcriptional activity similar to that of the wild-type molecule. Two of the mutations mapped to the ligand binding pocket (L290 and C318) and one to helix 11 (A494) [Jin et al. Mol Endocrinol 24, 923-929 (2010)], consistent with digoxin binding inside the pocket.

Figure 2A:
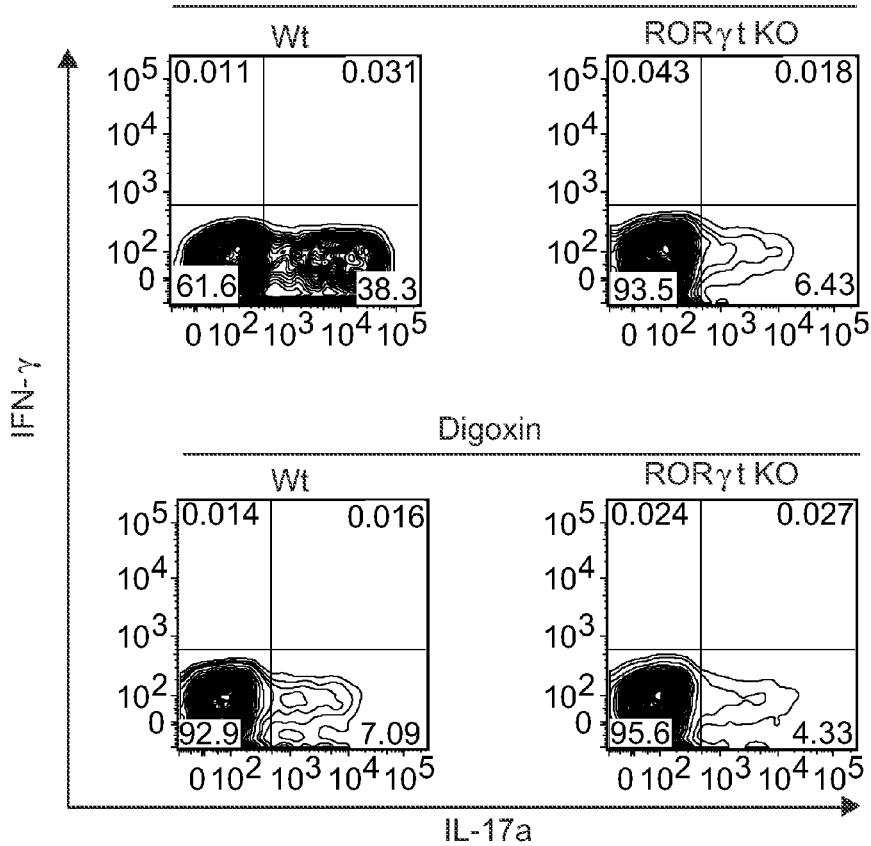
FIG. 2 reveals that digoxin inhibits mouse Th17 cell differentiation and ameliorates Th17-mediated autoimmune disease. a, Flow cytometry of intracellular staining for IL-17a and IFN-γ in sorted naive T cell populations activated and expanded in the presence of mouse Th17 polarizing cytokines (IL-6, TGF-β, and anti-TCR stimulation). Naive $CD25^-CD62L^+CD44^{low/int}$ cells were sorted from $RORγt^{fl/fl}$ mice and transduced with control-IRES-GFP (WT) or CRE-IRES-GFP (KO) retrovirus. DMSO or 10 μM digoxin was added at 6 hours after viral transduction on day 1 and GFP expressing cells were gated for analysis on day 5. b, Real-time PCR analysis of relative expression of indicated genes as compared to β-actin in WT T cells grown under Th0 or Th17 conditions. The results represent mean and standard deviation in two independent experiments. For each probe set, one of the DMSO-treated samples under Th17 polarization conditions was set at 100%. c, Gene expression profiles of Th17-polarized cells, comparing RORγt deficiency with digoxin treatment. Shown are the heat-maps for selected genes (338 genes that were differentially regulated in digoxin-treated WT cells compared to DMSO-treated WT control cells, among 45,101 probes on the Affymetrix microarrays) from duplicate samples, whose change in expression was statistically significant (Fold change>2, p<0.05). d, Selective inhibition by digoxin of RORγt-regulated IL-17a expression. FACS-sorted naive T cells were transduced with retroviral vectors encoding murine RORα-IRES-GFP or RORγt-IRES-GFP on Day 1 (16 h after TCR stimulation) and GFP expressing cells were gated for analysis on Day 5. DMSO or 10 μM digoxin was added 6-8 h after transduction. e, Digoxin inhibits binding of RORγt to target genes. Chromatin obtained from Th17-polarized cells treated with DMSO or digoxin (at 10 and 20 μM) was immunoprecipitated with IgG or anti-RORγ antibodies, followed by real-time PCR analysis. The int8 region of the Il23r locus served as a negative control. f, EAE disease course in B6 wild-type mice that were IP injected with either DMSO or digoxin every day starting from day 2 after disease induction with MOG(35-55)/CFA (complete Freund's adjuvant). Shown is averaged curve shape from seven experiments (10 or 20 mice were used per trial). * indicates statistical significance (p<0.05). g, Th1 and Th17 cells in spinal cord of EAE mice treated with DMSO or digoxin. Lymphocytes were isolated on day 21 after disease induction. The cells were stimulated for 4 h with PMA/Ionomycin and stained for surface markers and intracellular cytokines. Representative FACS plots (gated on $CD45^+CD11b^-CD4^+$ cells) from mice from each group are shown (top). T cells isolated from spinal cords of DMSO (n=7) or digoxin treated mice (n=7) were stained intracellularly for IFN-γ or IL-17a. Statistical analysis was by a two-tailed unpaired Student's t test; NS, not significant and p=0.014 (bottom).
Figure 2B:
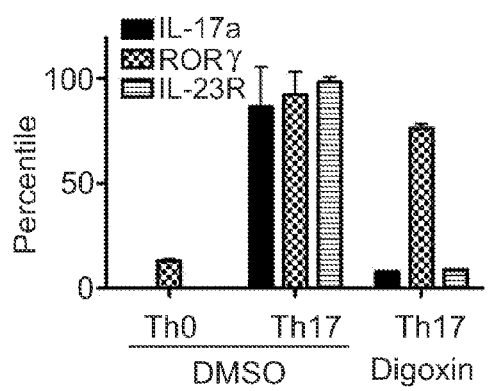
Figure 2C:
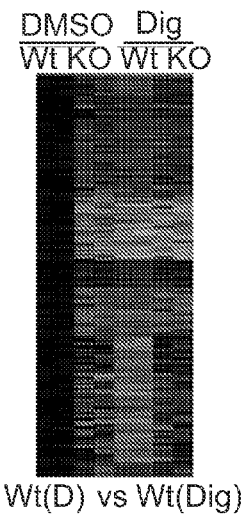
Figure 2D:
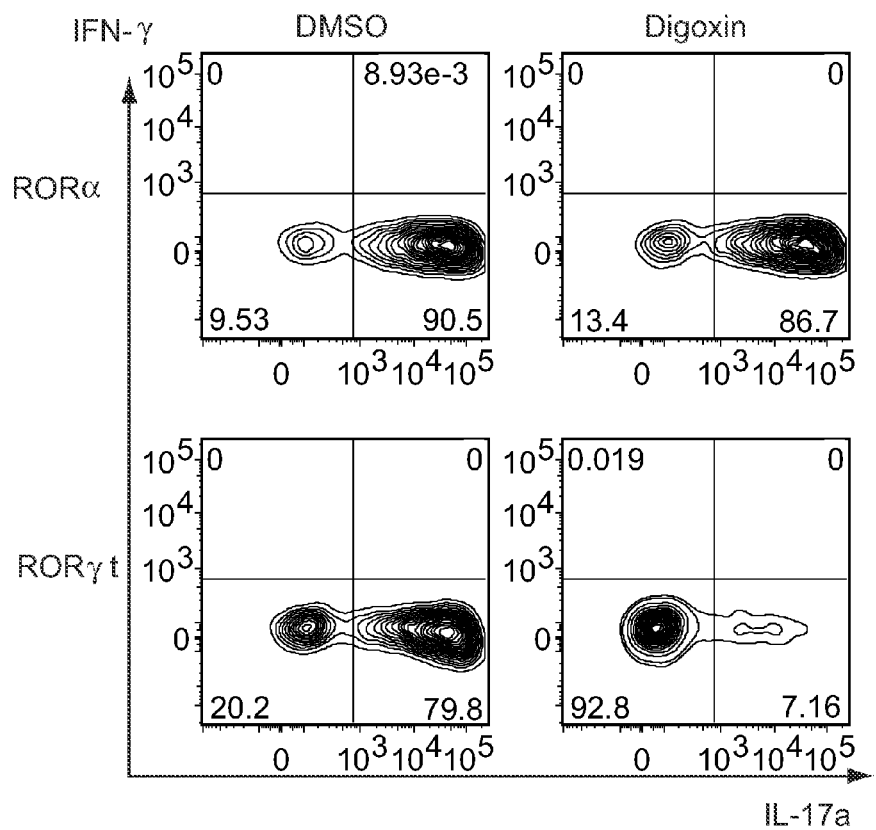
Figure 2E:
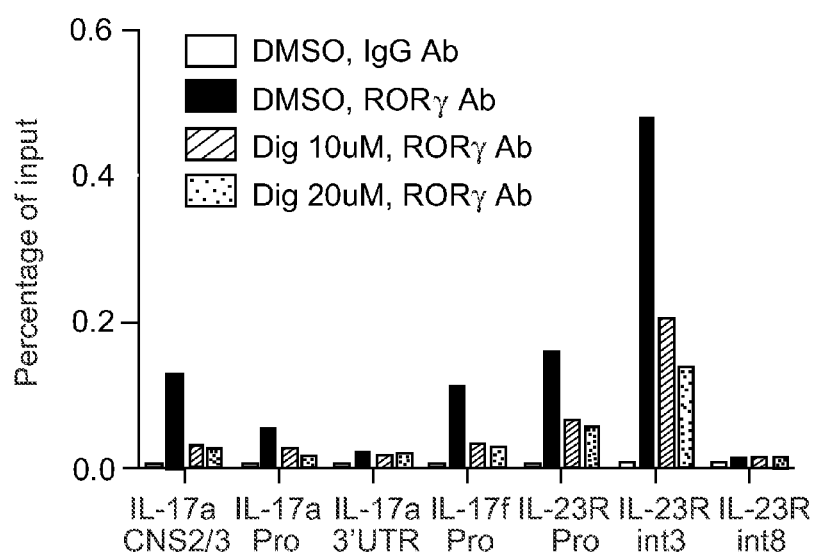

When naive mouse CD4+ T cells were cultured under Th17 polarizing conditions, treatment with digoxin led to markedly reduced expression of both IL-17a mRNA and protein (FIGS. 2a and b). Transcriptional up-regulation of the gene encoding IL-23 receptor (IL-23R), a key component of the Th17 cell differentiation program, was also strongly inhibited (FIG. 2b). Reduction of Th17 cell differentiation following treatment of wildtype cells with digoxin was similar to that observed upon targeted inactivation of Rorc(t) (FIG. 2a). Importantly, digoxin had no effect on differentiation of naive CD4+ T cells into other lineages, including Th1, Th2, and regulatory T cells.

To investigate if RORγt is the major target of digoxin or if another dominant cellular target exists, gene expression profiling was performed with total RNA samples isolated from DMSO- or digoxin-treated wild-type or RORγt-deficient cells cultured in Th17 conditions. Treatment with digoxin resulted in changes in gene expression that were very similar to those observed in RORγt-deficient cells, suggesting that the effects of digoxin are predominantly mediated through RORγt. Induction of RORγt mRNA and protein expression was not affected by digoxin (FIG. 2b). To rule out the possibility that digoxin blocks steps downstream of RORγt activity during Th17 cell differentiation (e.g. IL-17a production), its effect upon RORγt or RORα expressed ectopically in naive CD4+ T cells was examined. Both nuclear receptors were previously shown to be sufficient to induce IL-17a expression [Yang et al. Immunity 28, 29-39 (2008)], presumably by binding to the same cis-acting elements [Sato et al. Neuron 43, 527-537 (2004)]. Digoxin suppressed RORγt—but not RORα-mediated induction of IL-17a (FIG. 2d), confirming that it acts selectively on RORγt in mouse T cells. Digitoxin and β-acetyldigoxin also selectively inhibited RORγt-dependent Th17 cell differentiation. The aryl hydrocarbon receptor (AHR) is another ligand-dependent transcription factor that augments Th17 responses [Veldhoen et al. Nature 453, 106-109 (2008)]. Its activity was unaffected by digoxin, as addition of the AHR ligand FICZ increased RORα-dependent IL-17a expression even in the presence of digoxin. RORγt is predominantly found in the nucleus of Th17 cells [Zhou et al. Nature 453, 236-240 (2008)]. Digoxin treatment did not inhibit its nuclear localization in Drosophila cells or in in vitro differentiated Th17 cells. These data raise the question of how digoxin suppresses RORγt transcriptional activity. Chromatin immunoprecipitation-sequencing (ChIP-Seq) analysis with an anti-RORγt antibody was used for genome-wide identification of its transcriptional target sites in Th17 cells (M. Ciofani and D. R. L., unpublished results). The effect of digoxin on binding of RORγt to sites in two relevant loci, Il17a/f and Il23r was evaluated. RORγt binding to these sites was substantially reduced upon treatment with digoxin (FIG. 2e), demonstrating one mode of its activity.

Figure 2F:
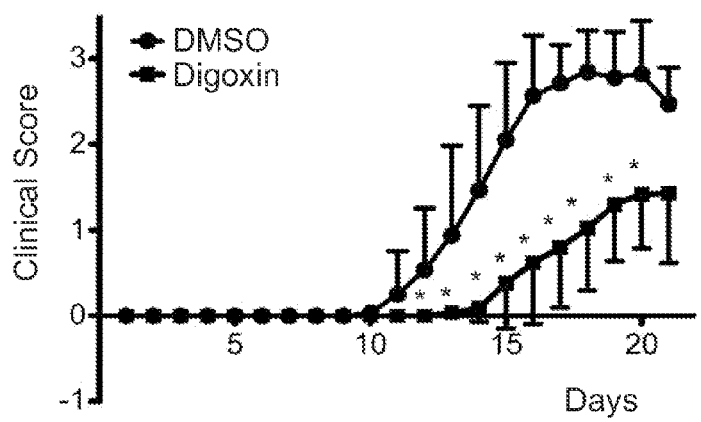
Figure 2G:
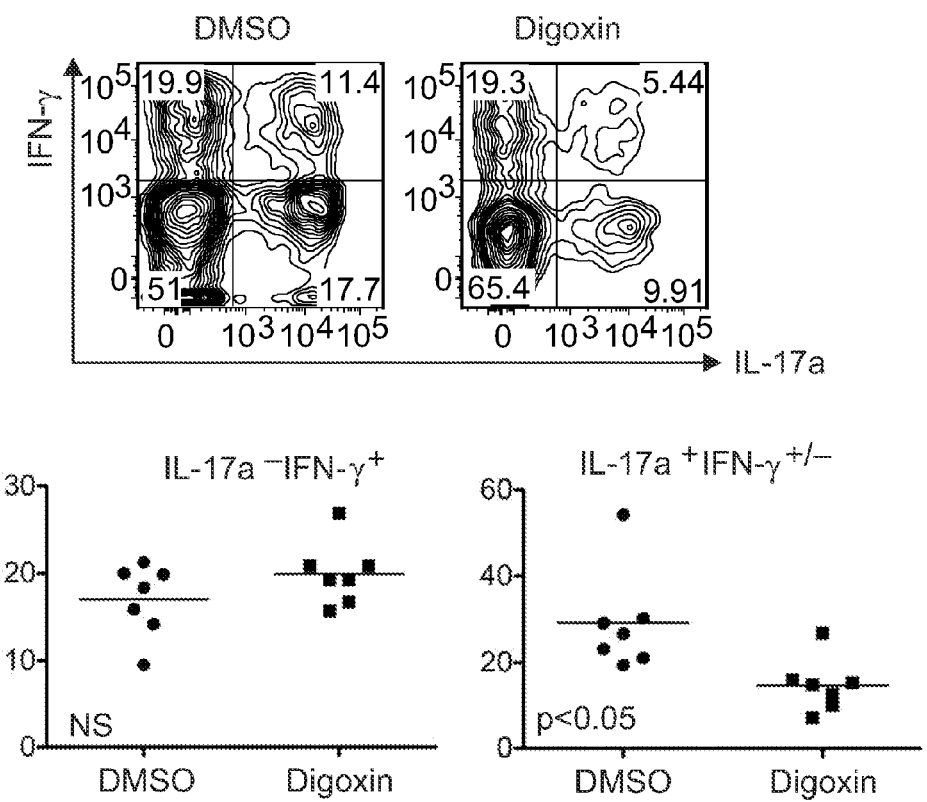
Figure 5:
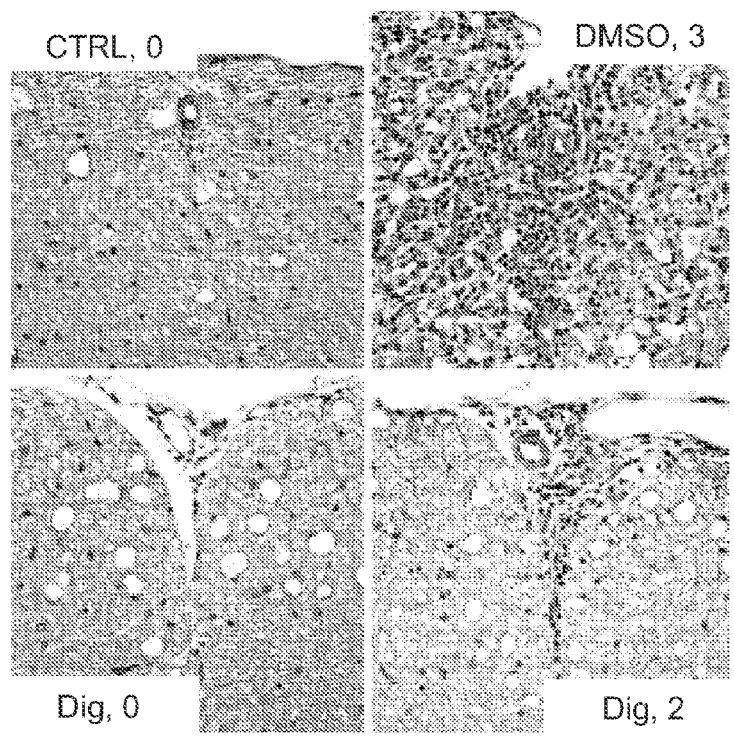
FIG. 5 shows histological sections of H&E-stained lumbar spinal cords from DMSO- or digoxin-treated animals with different EAE scores on day 14 after disease induction. Monocytic infiltration is rare in digoxin-treated, asymptomatic animals (clinical score 0).

The present inventors next examined if digoxin can exert an anti-inflammatory effect in mice. Accordingly, the present inventors induced experimental autoimmune encephalomyelitis (EAE), a Th17-mediated autoimmune inflammatory disease, in C57BL/6 wild-type mice [Langrish et al. J Exp Med 201, 233-240 (2005); Cua et al. Nature 421, 744-748 (2003)] in conjunction with intraperitoneal (IP) injections of digoxin or carrier each day from day 2. Digoxin treatment not only delayed onset, but also reduced severity of EAE progression (FIG. 2f). Also, the total number of mononuclear cells infiltrating the spinal cord was markedly reduced in mice treated with digoxin (FIG. 5). Importantly, the percentage of IL-17-producing T cells infiltrating the spinal cord in digoxin-treated mice was reduced by more than 50%, as compared to DMSO-treated mice, whereas that of IFN-γ-producing Th1 cells was approximately the same (FIG. 2g). Administration of digoxigenin, the aglycone of digoxin that does not inhibit RORγt activity in Drosophila cells and does not bind to the RORγt LBD, had no effect on progression of EAE, indicating that the cardiac glycoside activity [Paula et al. Biochemistry 44, 498-510 (2005)] has no role in the observed amelioration of disease.

Figure 6A:
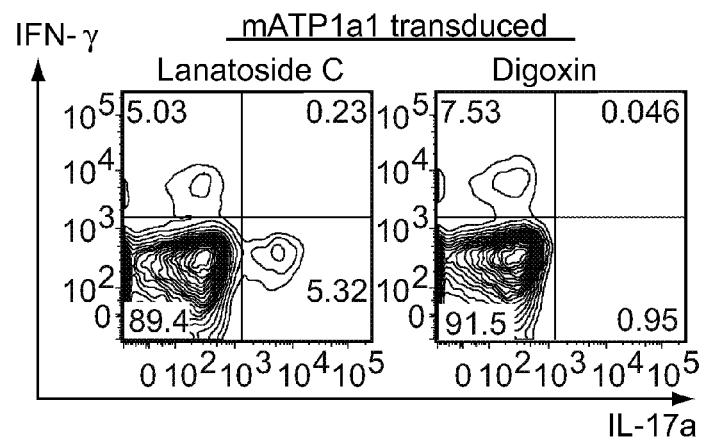
FIG. 6 reveals that ectopic expression of murine ATP1a1 confers resistance to digoxin-mediated cytotoxicity and demonstrates digoxin-mediated suppression of human Th17 cell differentiation. a, Human cord blood $CD4^+$ T cells, transduced with murine ATP1a1, were cultured with anti-CD3/CD28 beads along with IL-2, IL-23, IL-1β, and TGF-β in the presence of lanatoside C or digoxin (10 µM), and intracellular cytokine staining was performed on day 6. b, $CD4^+$ T cells isolated from peripheral blood of healthy adult donors were co-transduced with mATP1a1-IRES-HSA and control-IRESGFP or ROR αd, β, γt-IRES-GFP. After 6 days, cells were intracellularly stained for IFN-γ or IL-17a, and FACS plots gated on HSA and GFP positive cells are shown. Lanatoside C or digoxin was added 6-8 hours after viral transduction.
Figure 6B:
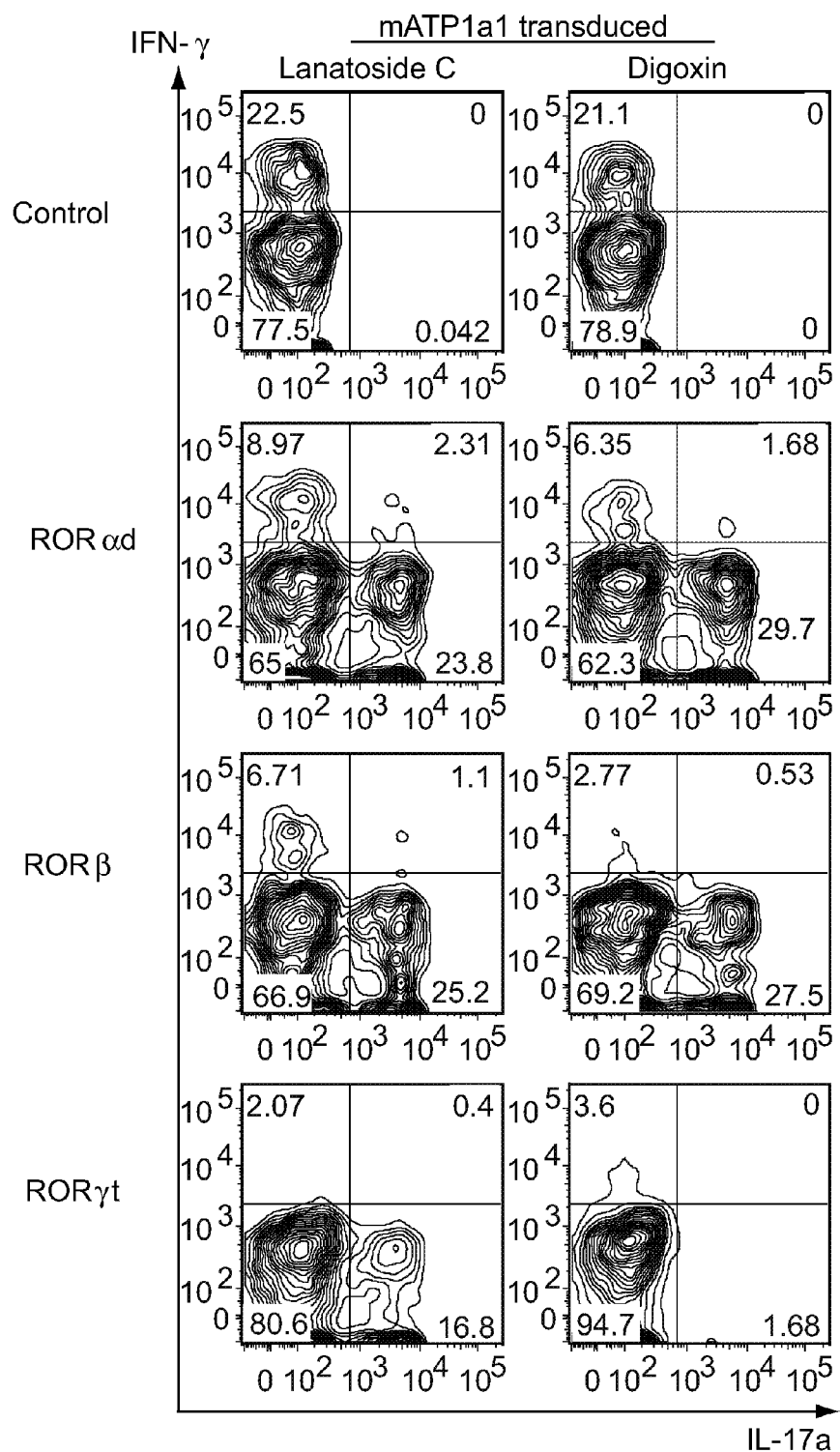

Digoxin, an inhibitor of the Na+/K+-ATPase, has long been used for treatment of congestive heart failure [Paula et al. Biochemistry 44, 498-510 (2005); Nesher et al. Life Sci 80, 2093-2107 (2007)], but is toxic for human cells at concentrations >300 nM [Johansson et al. Anticancer Drugs 12, 475-483 (2001)], well below those required for RORγt inhibition. Expression of the catalytic α1 subunit of murine Na+/K+-ATPase, which binds digoxin poorly, rendered human cells much less sensitive to digoxin-mediated cytotoxicity [Price et al. *Biochemistry* 27, 8400-8408 (1988); Zavareh et al. *Cancer Res* 68, 6688-6697 (2008)]. To take advantage of this property, the present inventors ectopically expressed in human cord blood CD4+ T cells the α1 subunit of murine Na+/K+-ATPase in the presence of cardiac glycosides. Lanatoside C, which has inhibitory activity on Na+/K+-ATPase similar to digoxin [Paula et al. *Biochemistry* 44, 498-510 (2005)], but does not inhibit RORγt activity, had no effect on IL-17a expression. However, digoxin suppressed IL-17a production without affecting IFN-γ expression (FIG. 6a). Next, human T cells expressing the murine Na+/K+-ATPase were further transduced with lentivirus encoding human RORαd, β, or γt, all of which are sufficient to induce IL-17 expression [Manel et al. *Nat Immunol* 9, 641-649 (2008); the content of which is incorporated herein by reference in its entirety]. Digoxin inhibited only RORγt-mediated induction of IL-17a (FIG. 6b), demonstrating its direct and selective activity on human RORγt.

Figure 3A:
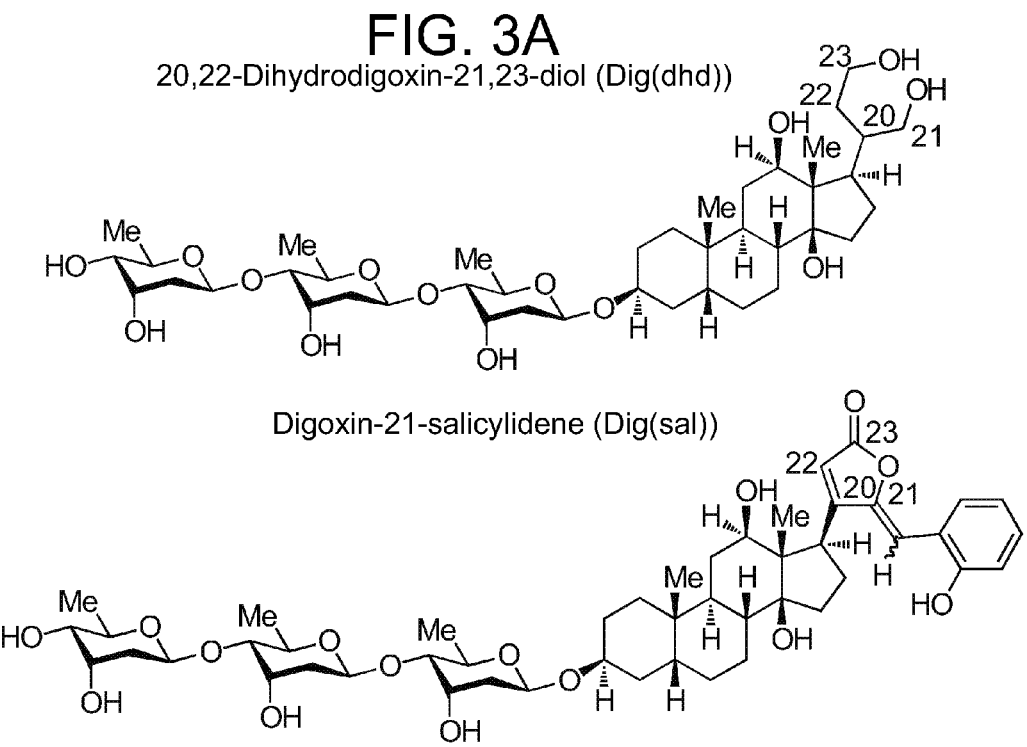
FIG. 3 shows that 20,22-Dihydrodigoxin-21,23-diol and digoxin-25-salicylidene inhibit human Th17 cell differentiation. a, Chemical structures of 20,22-dihydrodigoxin-21,23-diol and digoxin-21-salicylidene. b, Flow cytometry of IL-17a and IFN-γ production by cord blood naive CD4+ T cells $(CD45RO^-CD45RA^+CD3^+CD4^+CD25^-HLA-DR^-)$ transduced with RORαd-IRES-GFP or RORγt-IRES-GFP on day 1 and analyzed on day 6. GFP expressing cells were gated for analysis. DMSO, Dig(dhd) (40 μM) or Dig(sal) (10 μM) was added 6-8 h after viral transduction. c, Flow cytometry of the production of IL-17a and IFN-γ by human naive cord blood T cells cultured for six days in the presence of IL-2, IL-23, and IL-1β, with various concentrations of TGF-β. DMSO, Dig(dhd), or Dig(sal) at indicated concentrations (μM) was added 16 h after cytokine addition.
Figure 3B:
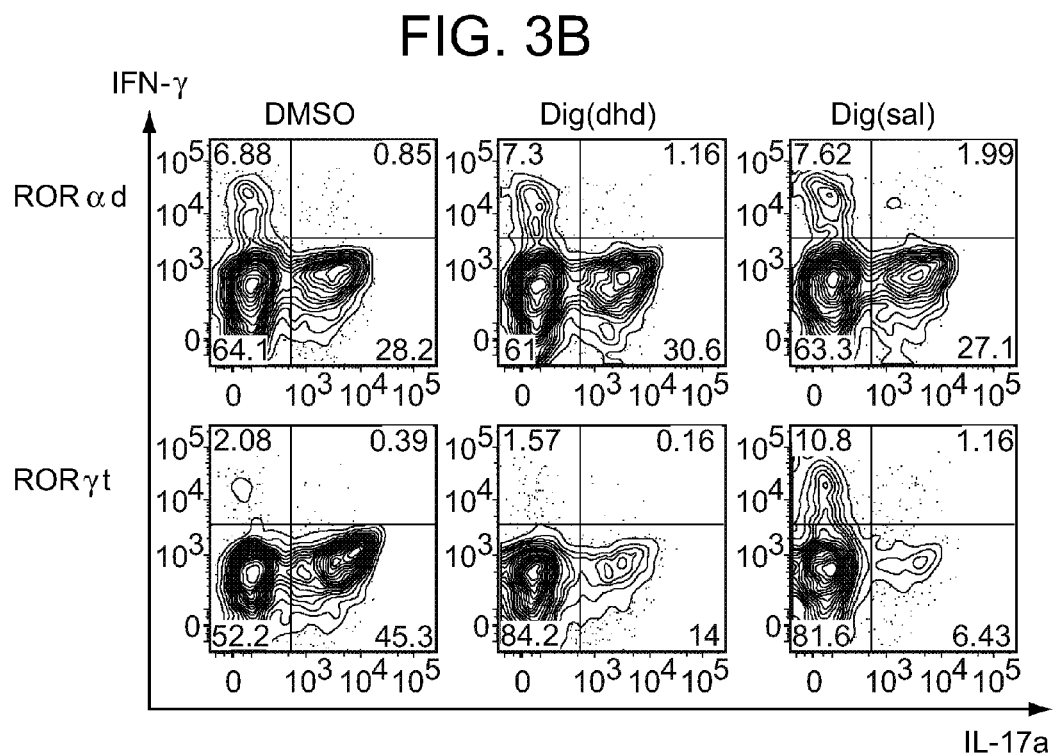
Figure 3C:
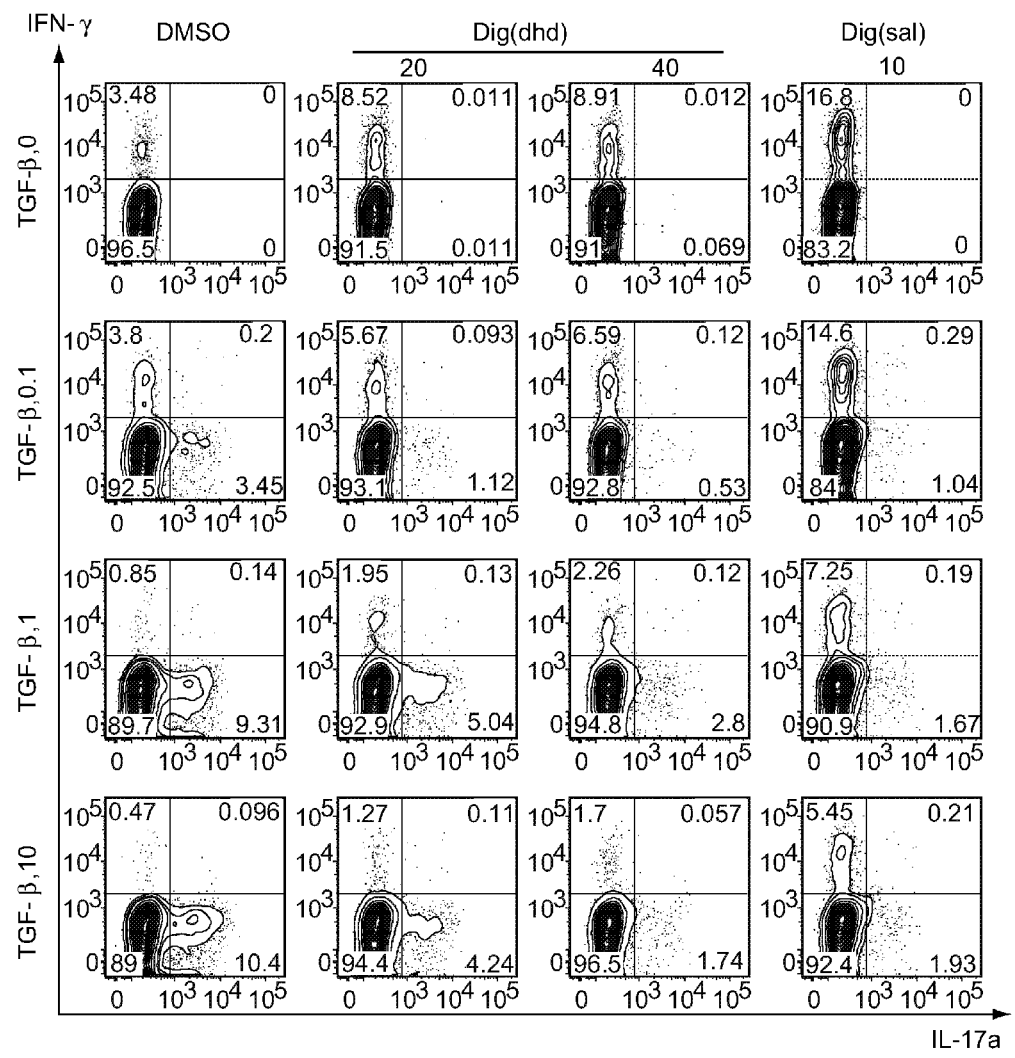

Cardiac glycosides of the cardenolide class comprise three common structural motifs, namely a steroidal core fused with a butenolide and various sugars [Prassas et al. *Nat Rev Drug Discov* 7, 926-935 (2008); Mijatovic et al. *Biochim Biophys Acta* 1776, 32-57 (2007)]. The glycans are dispensable, since digoxigenin still inhibits Na+/K+-ATPase [Paula et al. *Biochemistry* 44, 498-510 (2005)]. 20,22-Dihydrodigoxin, which was derived upon butenolide reduction of digoxin by the intestinal commensal *Eubacterium lentum* [Robertson et al. *Appl Environ Microbiol* 51, 1300-1303 (1986)], has weak cardiac glycoside activity with much lower binding affinity than that of digoxin for Na+/K+-ATPase [Paula et al. *Biochemistry* 44, 498-510 (2005); Lindenbaum et al. *N Engl J Med* 305, 789-794 (1981)], yet it inhibited RORγ activity in the S2 reporter system. Since 20,22-dihydrodigoxin was still cytotoxic for human cells at 2.5 μM, digoxin was further modified by complete reduction of the butenolide to generate Dig(dhd) (FIG. 3a). Dig(dhd) lacked cytotoxic activity on human cells at concentrations up to 40 μM, but it still possessed RORγ inhibitory activity and bound directly to RORγ in the in vitro competition assay ($IC_{50}$ of 12 μM). Additional derivatization of digoxin was achieved by aldol condensation of the butenolide with salicylaldehyde to produce Dig(sal) (FIG. 3a). When tested on human CD4+ T cells transduced with viruses encoding RORαd or RORγt, Dig(dhd) or Dig(sal) treatment selectively suppressed RORγt-mediated IL-17a induction (FIG. 3b). Intriguingly, addition of either compound blocked Th17 cell differentiation [Manel et al. *Nat Immunol* 9, 641-649 (2008)] (FIG. 3c) and induced reciprocal increases of IFN-γ expression in T cells (FIG. 3c), suggesting that functional RORγt or its downstream events may normally suppress development into other T cell lineages. Expression of another human Th17 cell-associated surface marker, CCR6, was also reduced in Dig(dhd) treated cells.

Figure 4A:
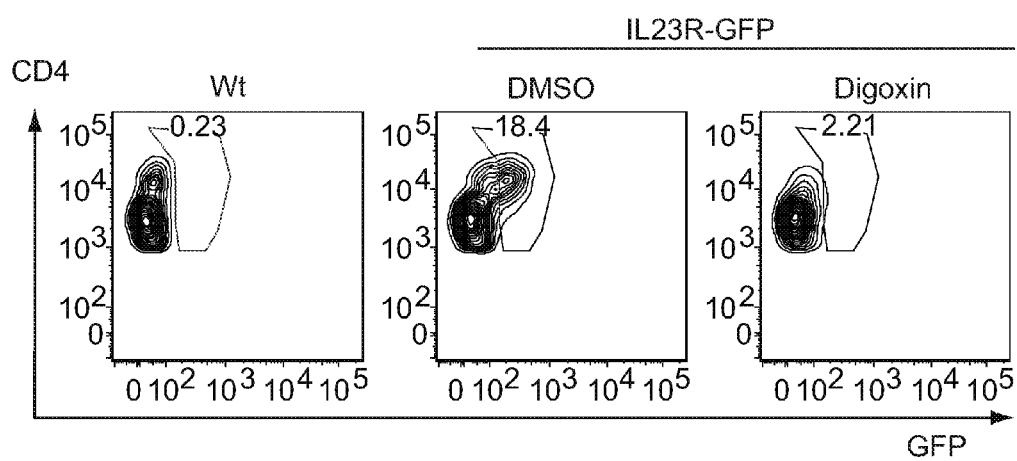
FIG. 4 demonstrates that RORγt activity is necessary for maintenance of mouse and human Th17 cells. a, b, Flow cytometry of intracellular staining for IL-17a and IFN-γ by CD4+ T cells. Mononuclear cells were collected from draining lymph nodes of wild-type or IL-23RGFP knock-in heterozygous mice 7 days after MOG(35-55)/CFA injection. Cells were cultured for four more days with MOG(35-55) peptide and exogenous IL-23 or IL-12, in the presence of DMSO or 10 μM digoxin. Without pre-immunization, addition of IL-23 and MOG(35-55) peptide to culture did not lead to de novo Th17 cell differentiation. Digoxin treatment suppressed expansion of in vivo differentiated Th17 cells, assayed by IL-23R reporter GFP expression (a) or by IL-17a production (b). c, d, Human naive ($CD45RA^+CD3^+CD4^+$) or memory ($CD45RO^+CD45RA^-CD3^+CD4^+CCR6^+CD161^+$) cells were purified from healthy donor peripheral blood samples and were cultured in the presence of IL-1β, IL-23 and IL-2 for 6 days with or without 40 µM Dig(dhd). Intracellular staining for IFN-γ or IL-17a in memory CD4+ T cells from multiple donors (n=11) in the presence of IL-1β, IL-23, and IL-2, assessed on day 6. c, Representative FACS plots from one donor are shown. d, Each symbol indicates a separate donor. Statistical analysis was by a two-tailed unpaired Student's t test; $IL-17a^-IFN-γ^+$, not significant and $IL-17a^+IFN-γ^{+/-}$, p=0.02.
Figure 4B:
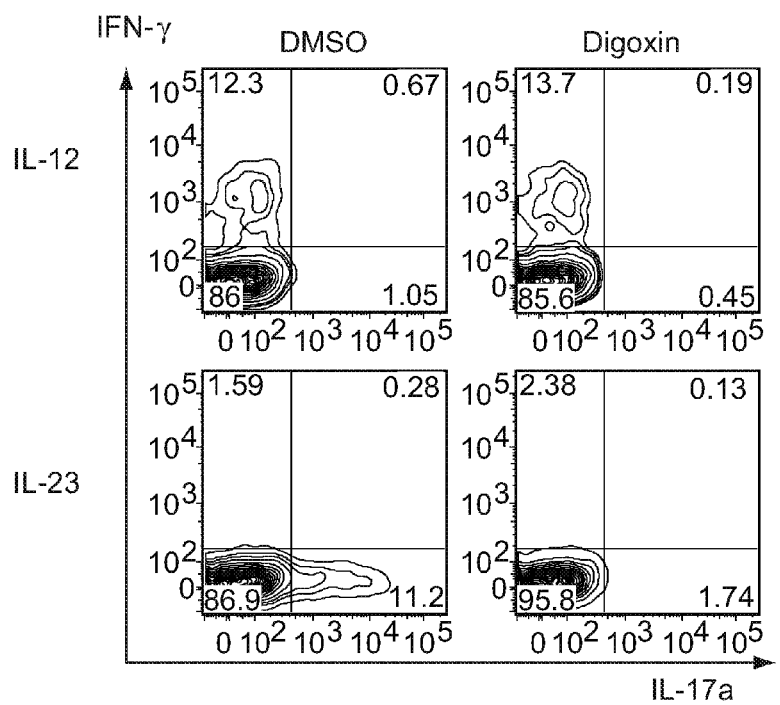
Figure 4C:
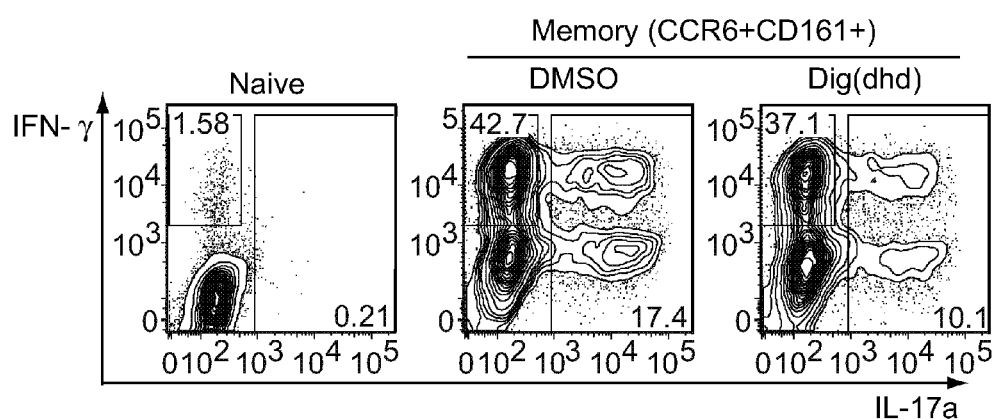
Figure 4D:
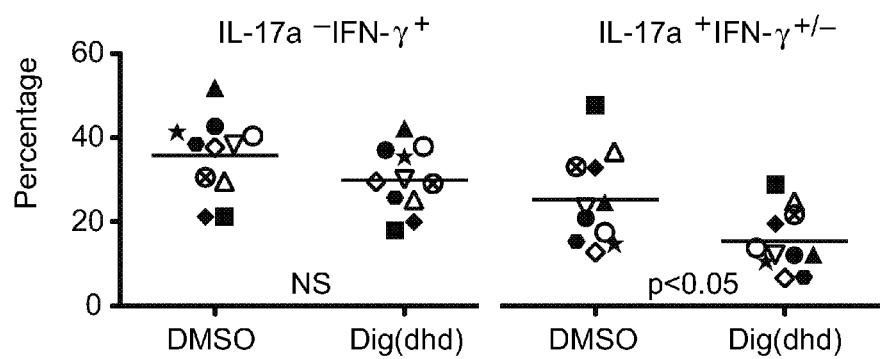
Figure 7A:
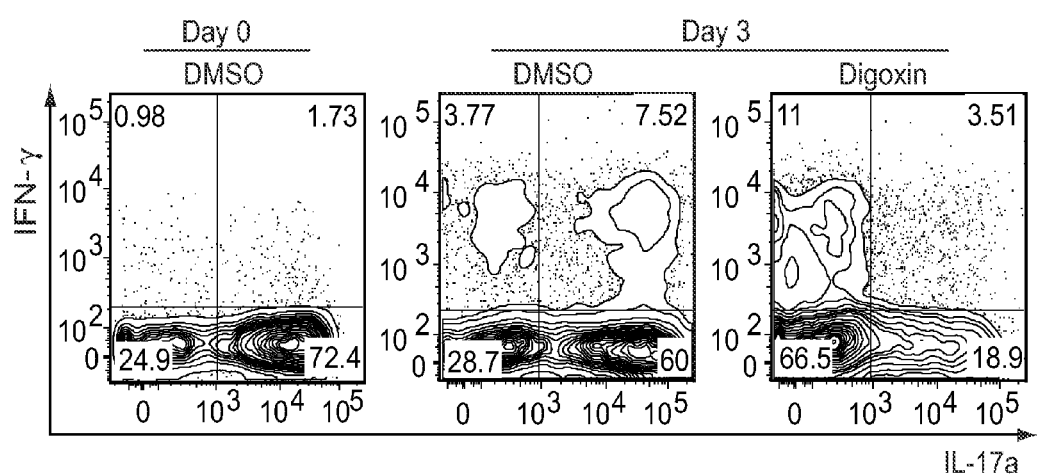
FIG. 7 shows that digoxin suppresses pre-differentiated Th17 cells both in vitro and in vivo. a, Mononuclear cells were collected from draining lymph nodes of IL-23R-GFP knock-in heterozygous mice 7 days after MOG/CFA injection and cultured for four days in the presence of IL-23 and MOG(35-55) peptide. IL-23R+ cells were FACS sorted based on GFP expression and cultured for three more days in the presence of IL-23 and DMSO or digoxin (10 µM). Intracellular staining for IL-17a and IFN-γ is shown after stimulation with phorbol 12-myristate 13-acetate (PMA) and ionomycin for 4 h. b, In vitro TH 17 polarized $CD4^+$ T cells, isolated from IFN-γ-deficient MBP (Myelin Basic Protein) TCR transgenic mice, were transferred to RAG-2 deficient mice, resulting in the development of non-classical EAE. DMSO or digoxin treatment was given to mice daily starting on day 2 (n=5). Clinical scores from one experiment are shown (representative of two independent experiments).
Figure 7B:
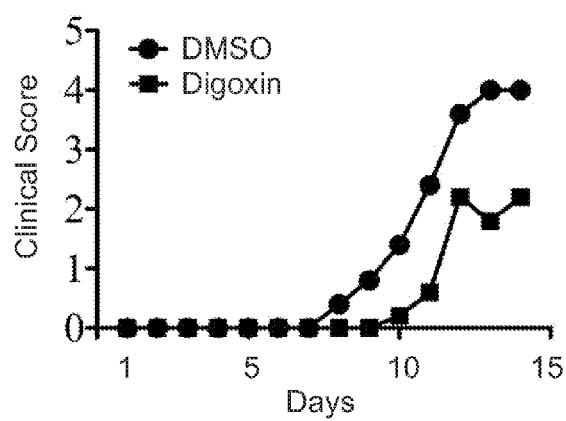

The present inventors next investigated if digoxin can inhibit IL-17 production from predifferentiated Th17 cells. In vitro digoxin treatment of expanded mouse Th17 cells derived from immunized mice inhibited both IL-23R (FIG. 4a) and IL-17a (FIG. 4b, bottom) expression without affecting IFN-γ expression (FIG. 4b, top). GFP-positive Th17 cells were also purified from MOG-immunized Il23gfp/+ mice25 after 4-day in vitro culture with IL-23 and MOG peptide. More than 70% of the sorted GFP-positive cells expressed IL-17a (FIG. 7a, day 0). GFP-positive cells were then treated with DMSO or digoxin for an additional 3 days. Digoxin treatment reduced IL-17a-expressing cells by more than 70% (FIG. 7a, day 3), confirming that mouse Th17 cells generated in vivo and expanded in vitro require continuous RORγt activity to maintain their identity. To test if digoxin suppresses the activity of pre-existing Th17 cells in vivo, IFN-γ-deficient, MBP-specific Th17 cells were transferred into lymphopenic RAG-2-deficient mice and EAE manifestation was assessed following daily administration of digoxin. Since the transferred cells lack IFN-γ, the EAE phenotype observed in these mice is entirely attributed to the function of Th17 cells. Digoxin treatment from day 2 delayed onset and reduced severity of Th17 cell transfer-mediated EAE, which further confirms a requirement for continuous RORγt activity in Th17 cells (FIG. 7b). The present inventors then examined if RORγt activity is also required for sustained expression of IL-17a in human CD4+ T cells. Human memory Th17 cells were purified from peripheral blood samples and enriched by in vitro culture. Naive CD4+ T cells cultured in the same cytokine conditions did not produce IL-17a (FIG. 4c, left plot). Dig(dhd) treatment led to 40-50% reduction of IL-17a-expressing cells with little effect on IFN-γ-expressing cells (FIGS. 4c and d). These data demonstrate that human RORγt activity plays an indispensable role in maintaining the human Th17 cell population.

Figure 8:
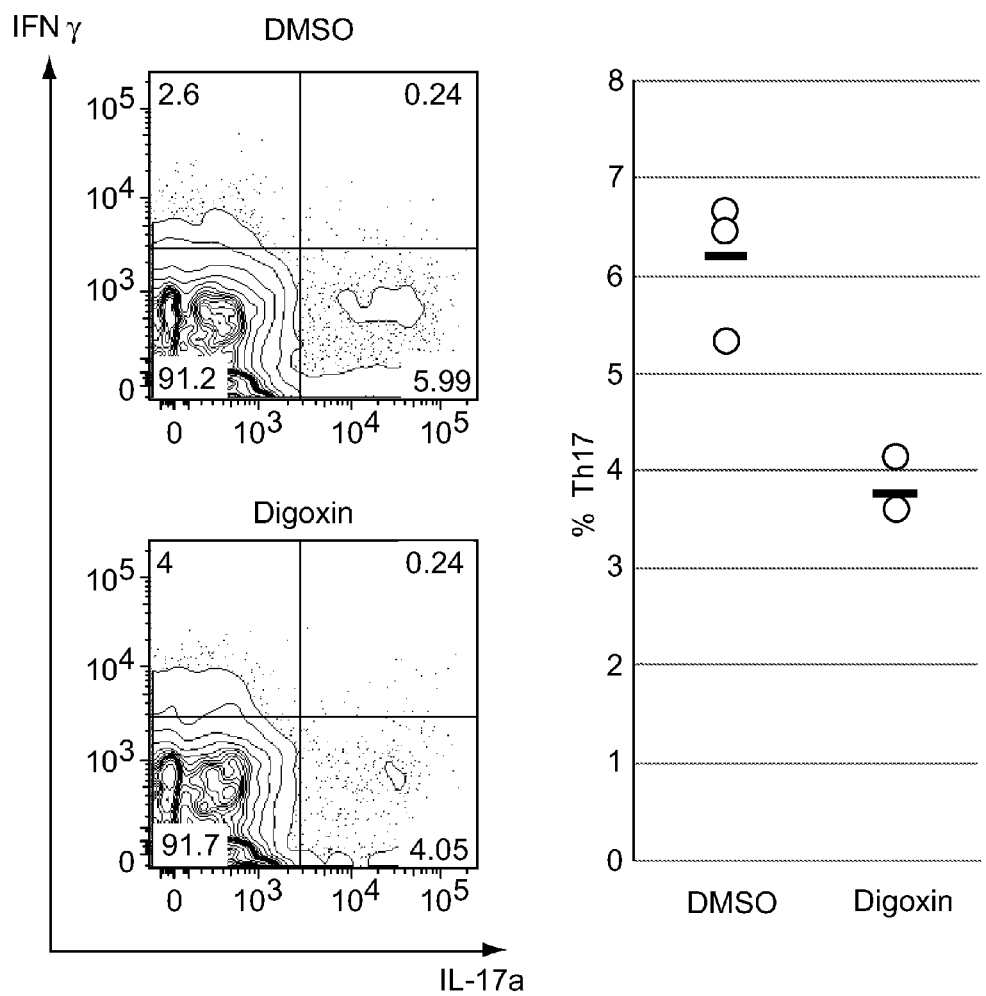

FIG. 8 reveals that digoxin treatment also leads to a reduction in the number of gut (large intestine) Th17 cells. These Th17 cells were induced following DSS treatment, a chemical agent that induces intestinal epithelial injury, and which is often used in an animal model for the intestinal bowel diseases. B6 wild-type mice were IP injected with either DMSO or digoxin every day starting from day 1.2% DSS was added to drinking water on day 1. Gut associated mononuclear cells were collected and their cytokine expression was analyzed on day 7. Representative FACS plots (gated on $CD4^+CD3^+TCR\beta^+CD19^-$ cells) from each group are shown (left). T cells isolated from large intestine of DMSO (n=3) or digoxin treated mice (n=3) were stained intracellularly for IFN-γ or IL-17a.

T cells and innate lymphocytes that produce IL-17a and IL-22 are recognized for having key roles in maintenance of barrier function at mucosal surfaces and also in the pathophysiology of autoimmune disease. All such cells, which include Th17 cells, other TCRαβ cells, TCRγδ cells, lymphoid tissue inducer cells, and NK-like cells (also referred to as NK22 cells) share in the property of requiring expression of RORγt for their differentiation. Abrogation of RORγt expression results in marked reduction or complete depletion of these cell types and in resistance to Th17-mediated autoimmune disease in mouse models [Buonocore et al. *Nature* 464, 1371-1375 (2010); Ivanov et al. *Cell* 126, 1121-1133 (2006); Eberl et al. *Science* 305, 248-251 (2004); Luci et al. *Nat Immunol* 10, 75-82 (2009)]. Therefore, RORγt antagonists digoxin, Dig(dhd), and Dig(sal) are at the least good chemical templates for the development of potent therapeutic compounds to treat various diseases associated with inflammatory lymphocyte dysfunction.

The digitalis-like compounds were originally identified in plants. A body of evidence indicates the presence of endogenous digitalis-like compounds in mammals and humans [Nesher et al. *Life Sci* 80, 2093-2107 (2007); Bagrov et al. *Nat Clin Pract Nephrol* 4, 378-392 (2008)]. Identification of digoxin as a RORγt antagonist suggests that related molecules in mammals may modulate RORγ- and RORγt-mediated functions. However, it would be derivative compounds with better $IC_{50}$ values that would have such roles. In light of recent findings of the roles of microbiota in generation of Th17 cells in the small intestine [Ivanov et al *Cell* 139, 485-498 (2009)], it is interesting that *Eubacterium lentum*, another commensal bacterium, has the capacity to metabolize digoxin into dihydrodigoxin. The possibility of endogenous digitalis-like compounds in host organisms and of their modification by microbes may present additional opportunities for modulating the function of RORγt and Th17 cell differentiation.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

The chemical names of compounds of invention given in this application are generated using Open Eye Software's Lexichem naming tool, Symyx Renassance Software's Reaction Planner or MDL's ISIS Draw Autonom Software tool and not verified. Preferably, in the event of inconsistency, the depicted structure governs.

What is claimed is:

1. A method for treating or ameliorating in a mammal a disease or condition that is causally related to RORγt activity in vivo, wherein the disease or condition is arthritis, diabetes, multiple sclerosis, uveitis, psoriasis, asthma, bronchitis, allergic rhinitis, chronic obstructive pulmonary disease, atherosclerosis, *H. pylori* infections, ulcers, inflammatory bowel disease, Crohn's disease, ulcerative colitis, sprue, food allergies or, experimental autoimmune encephalomyelitis (EAE), which comprises administering to the mammal an effective disease-treating or condition-treating amount of a compound according to formula III:

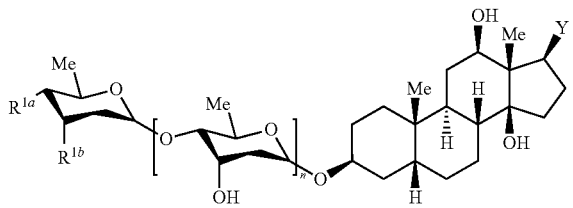

wherein
Y is $CO_2R^8$, $CH_2OH$,

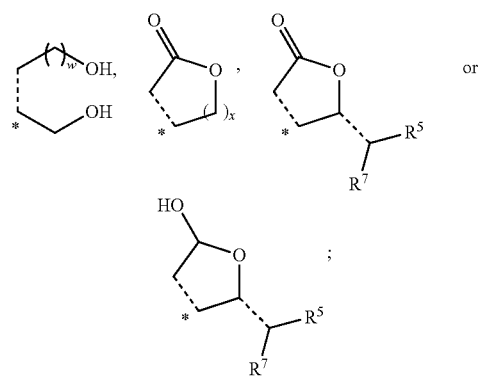

* denotes the attachment point; the subscript w is 0, 1, or 2;

the subscript x is 1, 2, or 3;

each $R^5$ and $R^7$ is independently H, substituted or unsubstituted alkyl, alkenyl, cycloalkyl, heterocycloalkyl, aryl, or heteroaryl;

$R^8$ is H or substituted or unsubstituted alkyl;

each $R^{1a}$ and $R^{1b}$ is independently OH, or O-acyl; or $R^{1a}$ and $R^{1b}$ together form

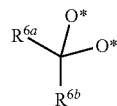

* denote the attachment points;

each $R^{6a}$ and $R^{6b}$ is independently H, substituted or unsubstituted alkyl, cycloalkyl, aryl or heteroaryl;

each subscript n is independently 0, 1, 2, 3, 4, or 5; and each dotted bond is independently a single or a double bond;

or a pharmaceutically acceptable salt, solvate or prodrug thereof;

and stereoisomers, isotopic variants and tautomers thereof.

2. The method according to claim 1, wherein Y is $CH_2OH$, $CO_2H$, $CO_2Me$, $CO_2Et$,

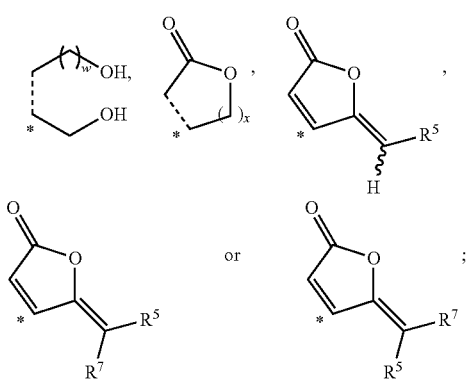

* denotes the attachment point; the subscript w is 0, 1, or 2;

the subscript x is 1, 2, or 3; and $R^5$ and $R^7$ are as in claim 1.

3. The method according to claim 1, wherein Y is

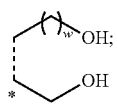

* denotes the attachment point; and the subscript w is 0, 1, or 2.

4. The method according to claim 1, wherein Y is

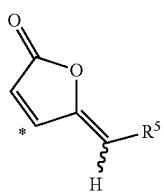

and $R^5$ is substituted or unsubstituted alkyl, substituted or unsubstituted alkenyl, substituted or unsubstituted aryl, substituted or unsubstituted heteroaryl, or substituted or unsubstituted cycloalkyl, and * denotes the attachment point.

5. The method according to claim 1, wherein Y is

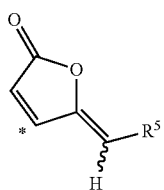

and $R^5$ is alkyl, unsubstituted, or substituted with halo, phenyl, hydroxyl or methoxy;

alkenyl, unsubstituted, or substituted with alkyl, or phenyl;

cycloalkyl, unsubstituted, or substituted with hydroxyl or methoxy; or aryl, unsubstituted, or substituted with substituted or unsubstituted alkyl, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted heterocycloalkyl, substituted or unsubstituted dialkylamino, halo, nitro, and thiol, and * denotes the attachment point.

6. The method according to claim 1, wherein Y is

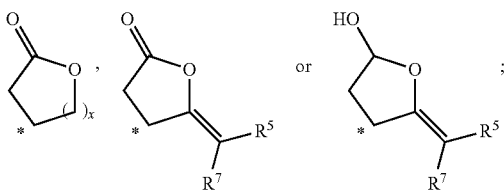

* denotes the attachment point;

the subscript x is 1, 2, or 3; and $R^5$ and $R^7$ are as in claim 1.

7. The method according to claim 6, wherein $R^5$ is alkyl, unsubstituted, or substituted with halo, phenyl, hydroxyl or methoxy, alkenyl, unsubstituted, or substituted with alkyl, or phenyl;

cycloalkyl, unsubstituted, or substituted with hydroxyl or methoxy; or aryl, unsubstituted, or substituted with substituted or unsubstituted alkyl, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted cycloalkyl, substituted or unsubstituted heterocycloalkyl, substituted or unsubstituted dialkylamino, halo, nitro, and thiol.
8. The method according to claim 6, wherein $R^7$ is H.
9. The method according to claim 1, wherein the compound is according to formula IVa, IVb, Va, Vb, VIa, VIb, VIc, or VId:
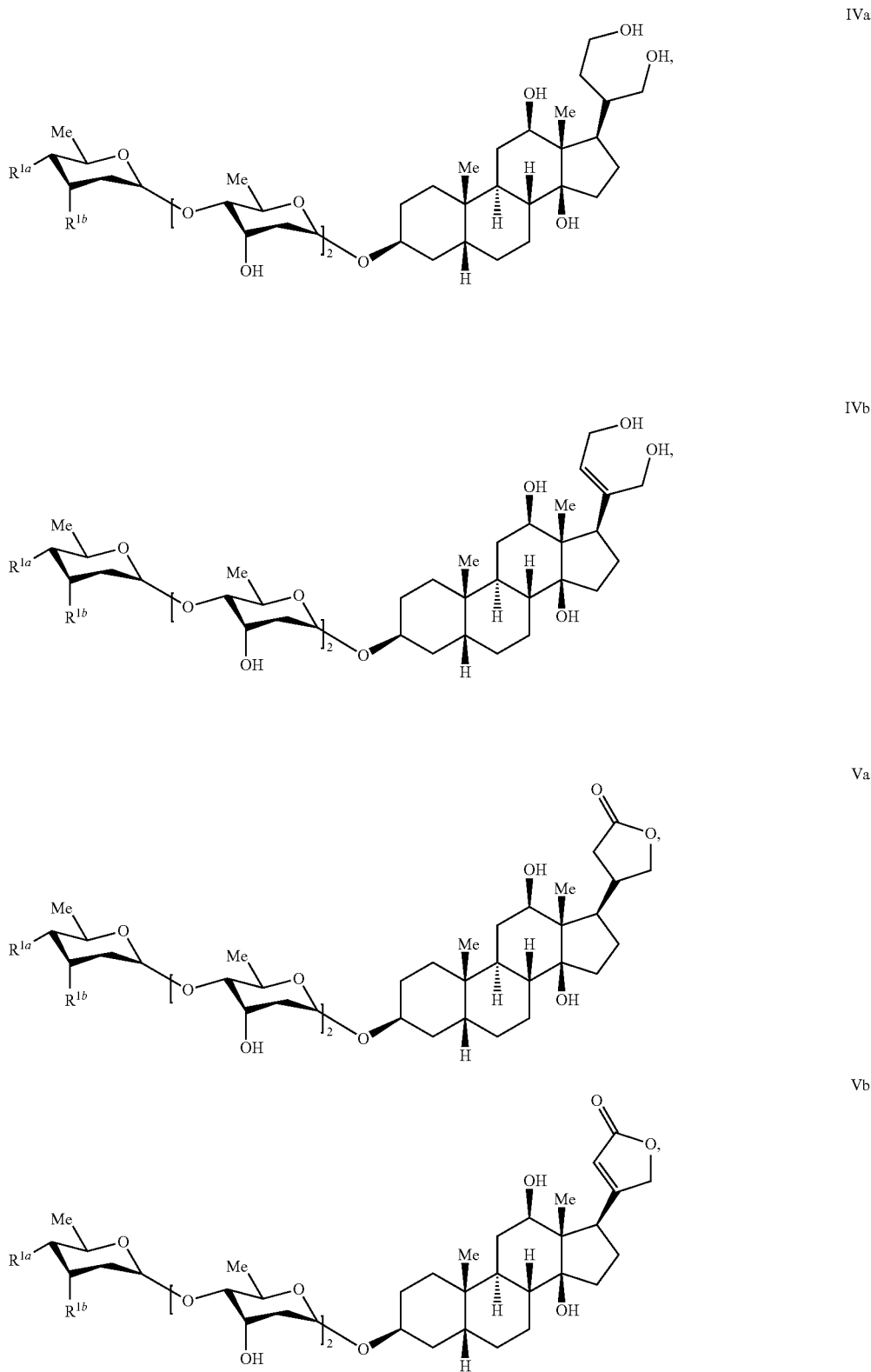

-continued
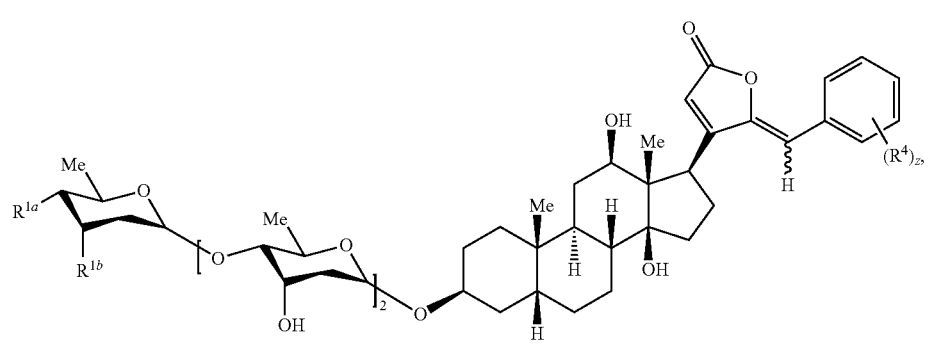
VIa
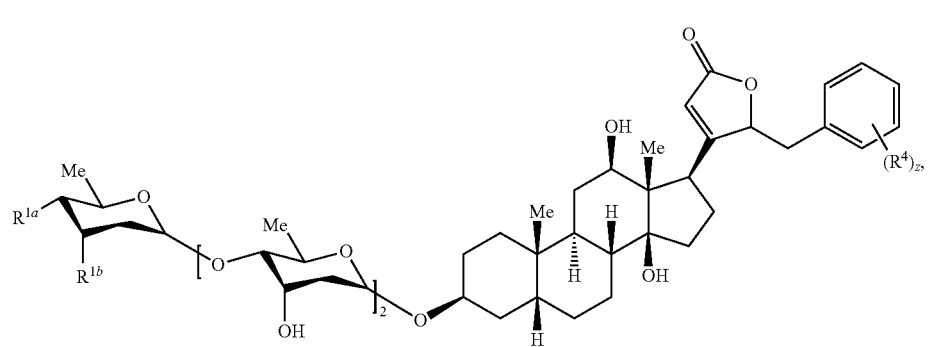
VIb
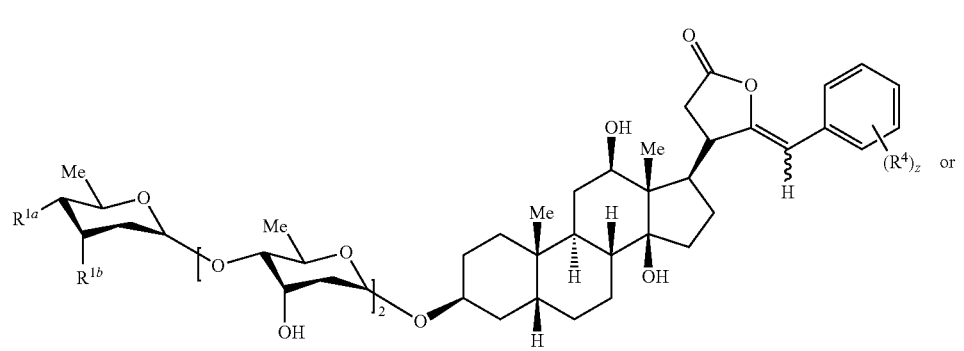
VIc or
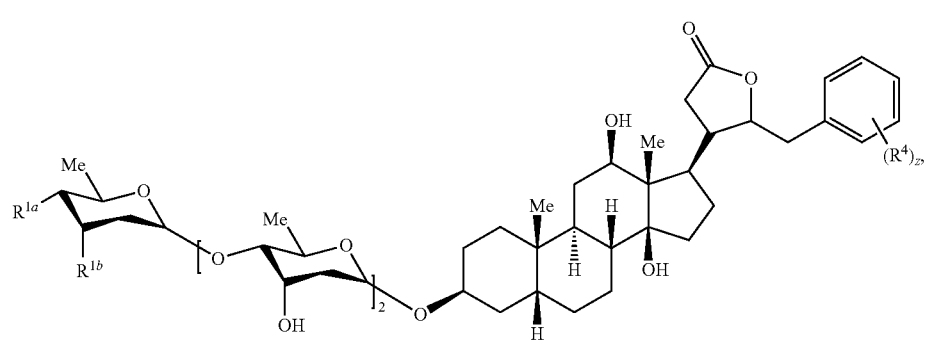
VId wherein
$R^{1a}$ and $R^{1b}$ are as in claim 1; z is 0, 1, 2, 3, 4, or 5; and each $R^4$ is independently selected from substituted or unsubstituted alkyl, substituted or unsubstituted acyl, substituted or unsubstituted acylamino, substituted or unsubstituted alkylamino, substituted or unsubstituted alkythio, substituted or unsubstituted alkoxy; substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkyl sulfonyl, substituted or unsubstituted aryl sulfonyl, azido, substituted or unsubstituted carbamoyl, carboxyl, cyano, substituted or unsubstituted cycloalkyl, substituted or unsubstituted heterocycloalkyl, substituted or unsubstituted dialkylamino, halo, nitro, hydroxyl, and thiol;
or a pharmaceutically acceptable salt, solvate or prodrug thereof;
and stereoisomers, isotopic variants and tautomers thereof.

10. The method according claim 9, wherein z is 1 or 2; and each $R^4$ is independently selected from F, Br, Cl, I, OH, Me, Et, $CF_3$, $OCF_3$, $CF_3$, $NMe_2$, OMe, OEt, $NO_2$, OPh, and SMe.

11. The method according to claim 1, wherein each $R^{1a}$ and $R^{1b}$ is independently OH or OAc.

12. The method according to claim 1, wherein $R^{1a}$ and $R^{1b}$ together form

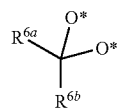

* denote the attachment points;
each $R^{6a}$ and $R^{6b}$ is independently H, substituted or unsubstituted alkyl, cycloalkyl, aryl or heteroaryl.

13. The method according to claim 1, wherein the compound is according to formula VIIa, VIIb, VIIc, VIIIa, VIIIb, VIIIc, IXa, IXb, IXc, Xa, Xb, Xc, XIa, XIb, XIc, XIIa, XIIb, or XIIc:

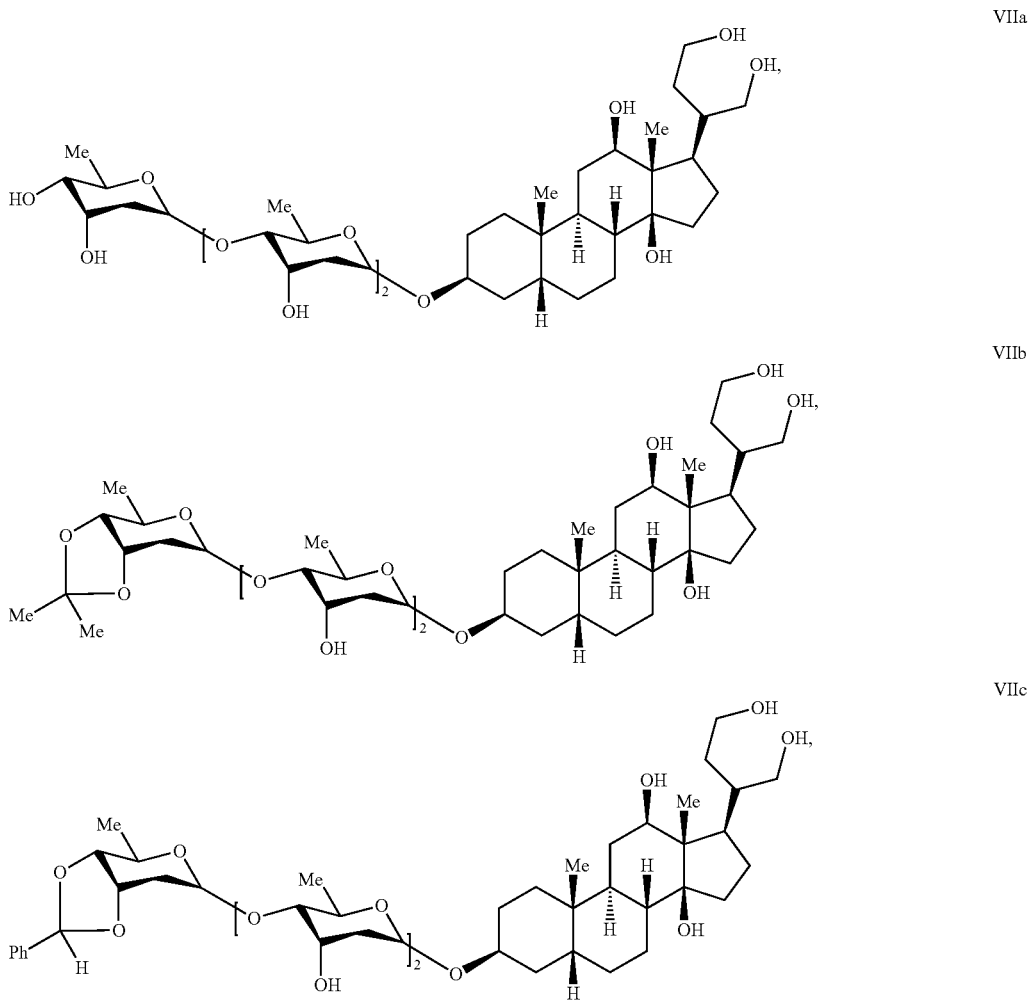

-continued
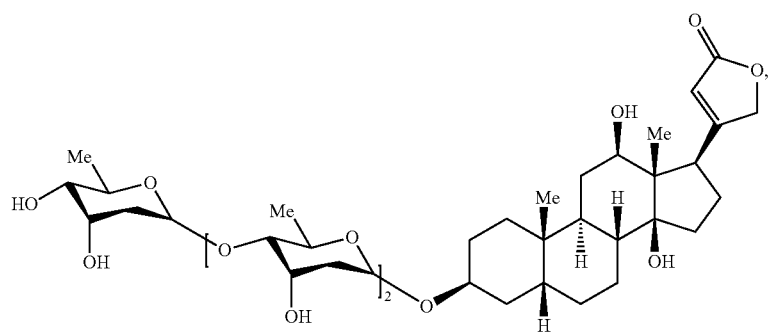
VIIIa
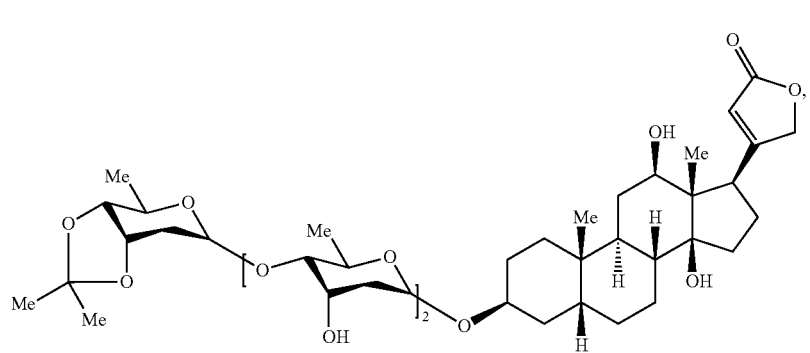
VIIIb
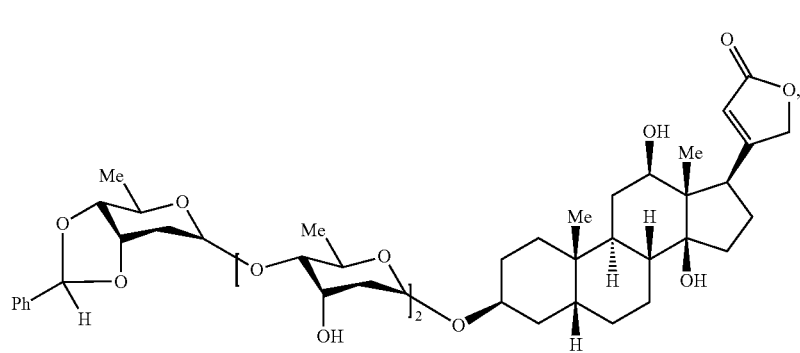
VIIIc
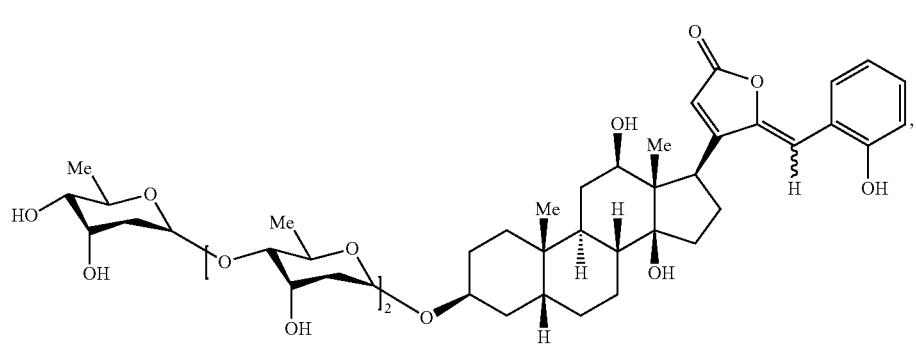
IXa -continued
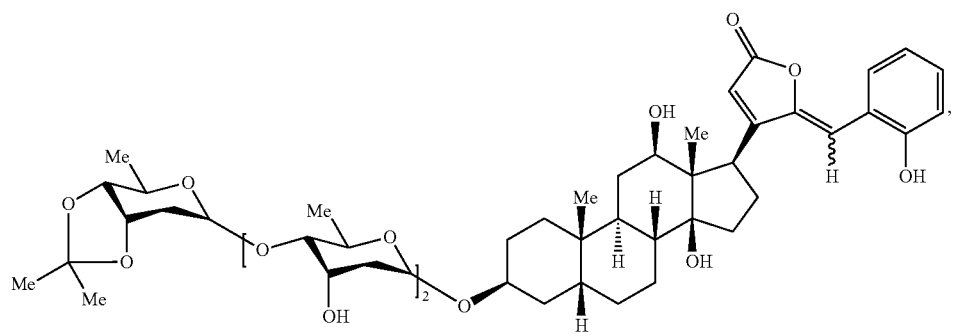
IXb
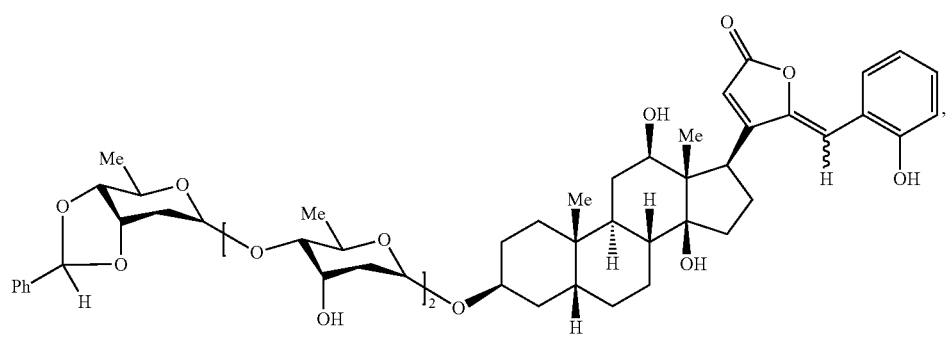
IXc
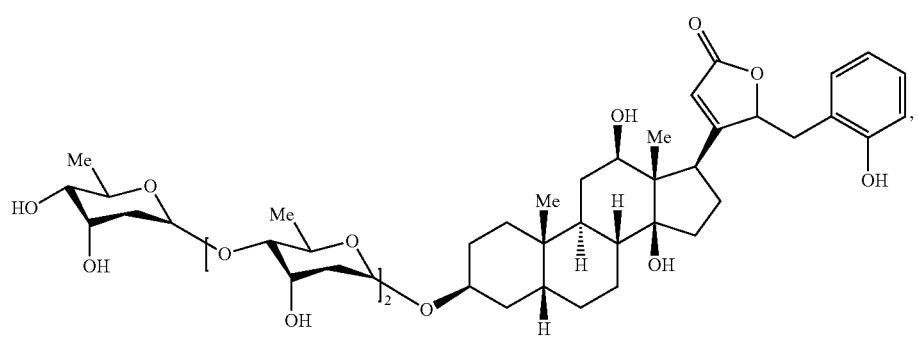
Xa
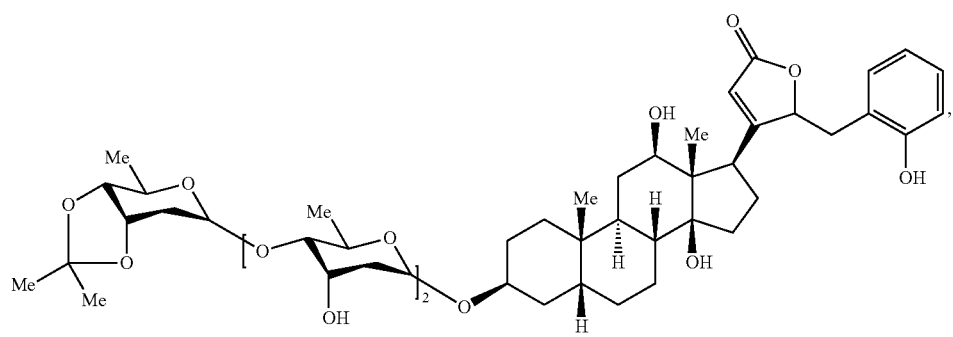
Xb -continued
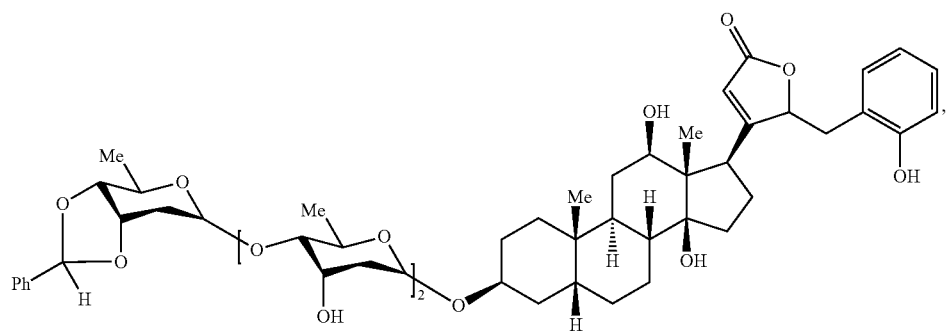
Xc
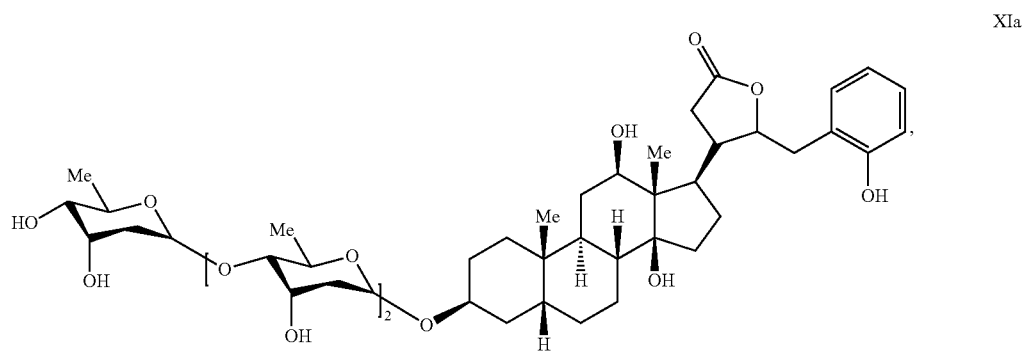
XIa
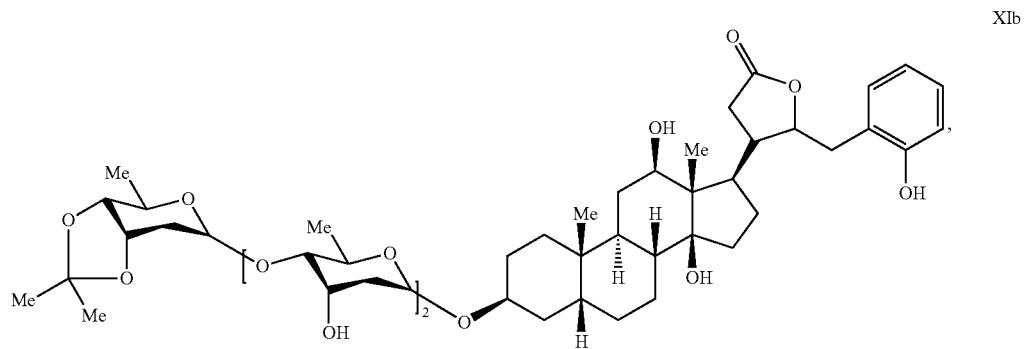
XIb
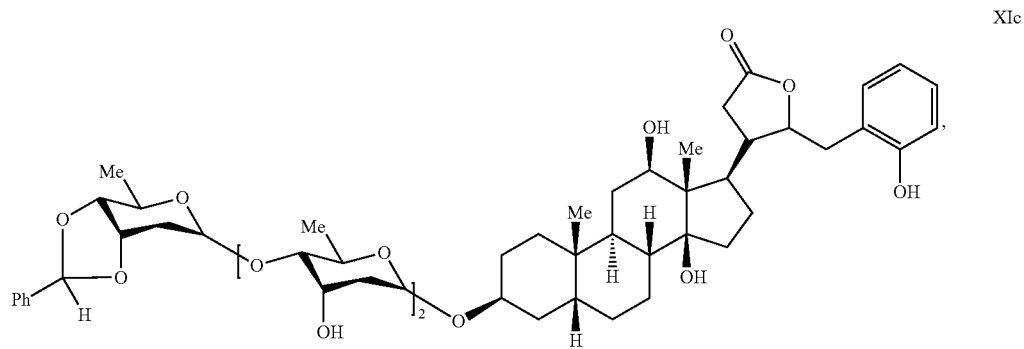
XIc -continued
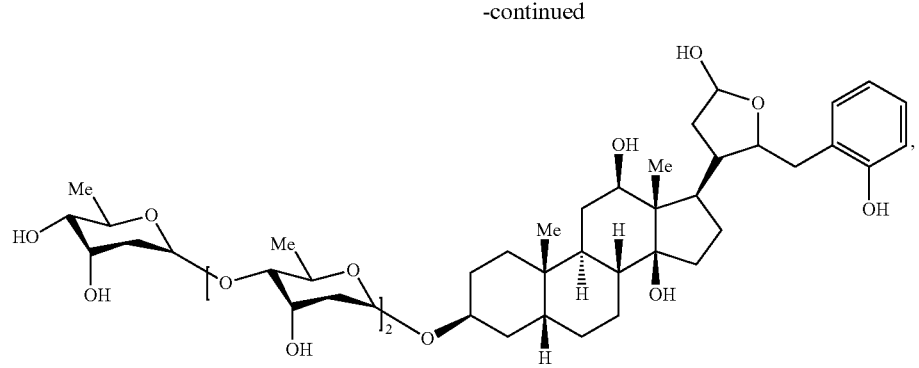
XIIIa
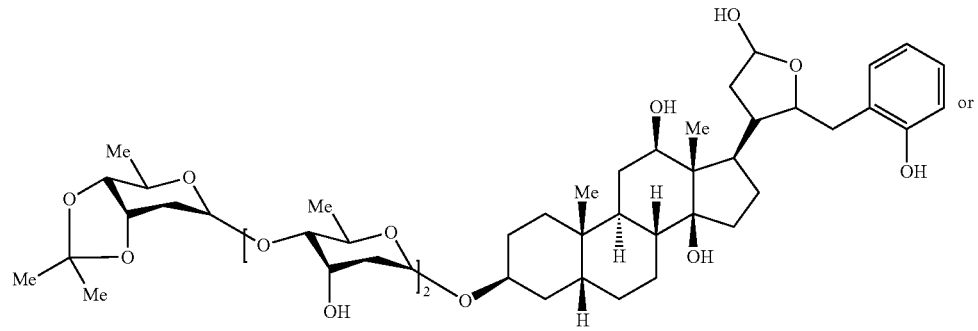
XIIIb
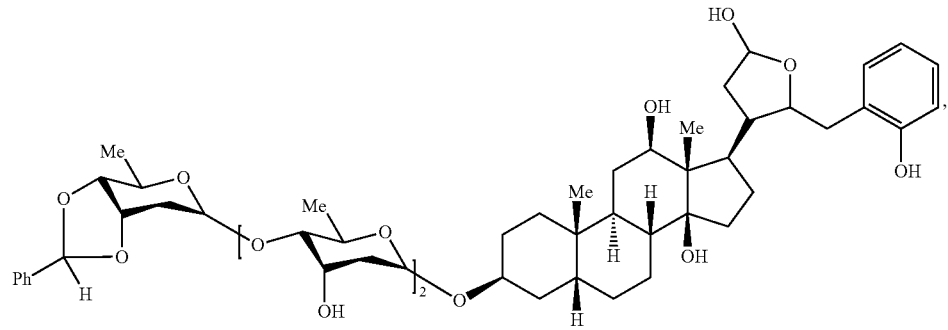
XIIIc
or a pharmaceutically acceptable salt, solvate or prodrug thereof;
and stereoisomers, isotopic variants and tautomers thereof.
14. The method according to claim 1, wherein the compound is according to formula XIIIa, XIIIb, or XIIIc:
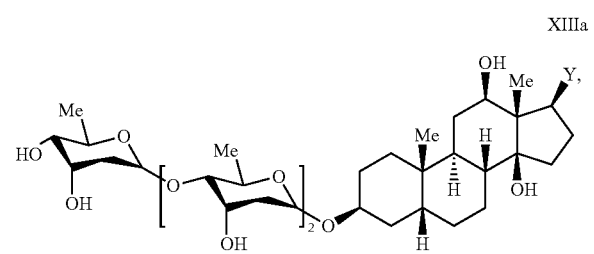
XIIIa
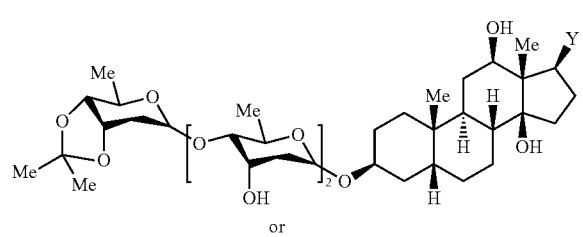
XIIIb
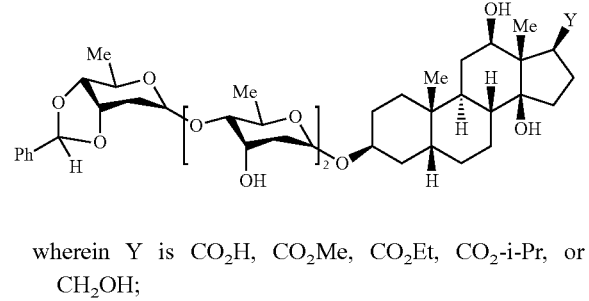
XIIIc
wherein Y is $CO_2H$, $CO_2Me$, $CO_2Et$, $CO_2\text{-i-Pr}$, or $CH_2OH$;

or a pharmaceutically acceptable salt, solvate or prodrug thereof;

and stereoisomers, isotopic variants and tautomers thereof.

15. The method according to claim 1, wherein the compound is according to formula III;

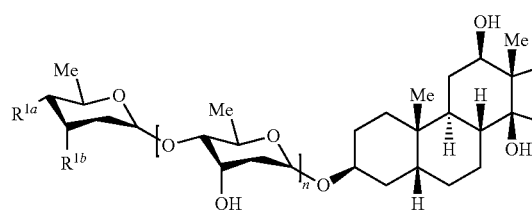

III and wherein

1. $R^{1a} = R^{1b} = OH$; n = 2; Y = 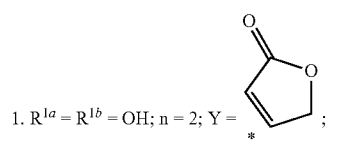;

2. $Y = R^{1a} = R^{1b} = OH$; n = 1; Y = 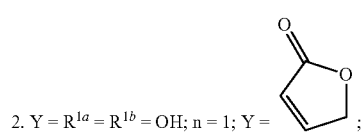;

3. $R^{1a} = R^{1b} = OH$; n = 0; Y = 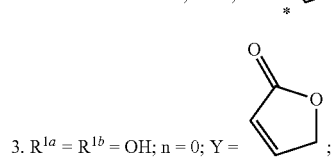;

4. $R^{1a} = R^{1b} = OH$; n = 2; Y = 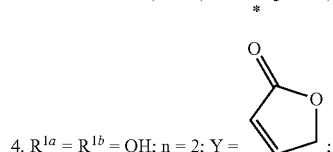;

5. 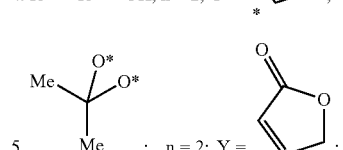;

6. 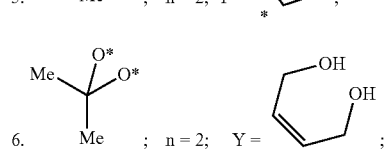;

7. 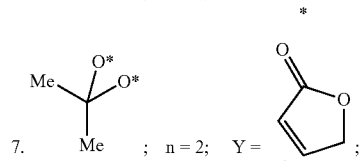;

8. 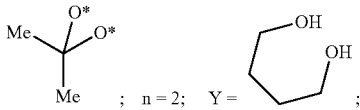;

9. 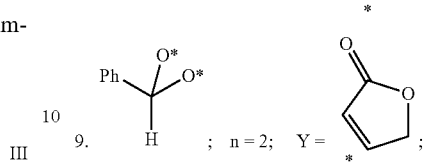;

10. 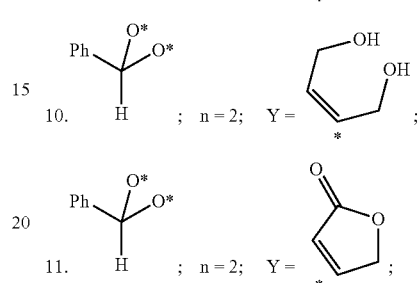

11. 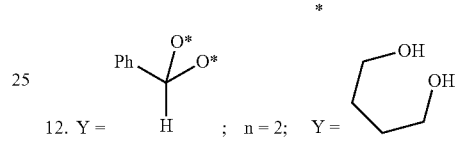

12. 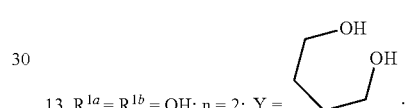;

13. $R^{1a} = R^{1b} = OH$; n = 2; Y = 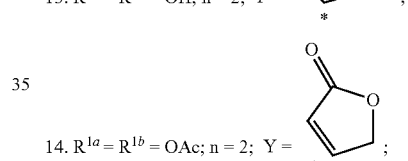;

14. $R^{1a} = R^{1b} = OAc$; n = 2; Y = 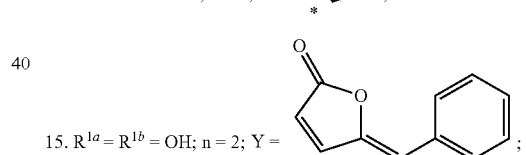;

15. $R^{1a} = R^{1b} = OH$; n = 2; Y = 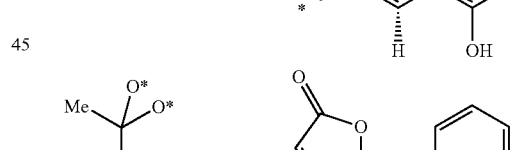;

16. 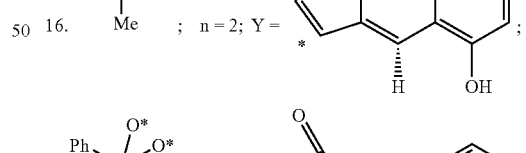;

17. 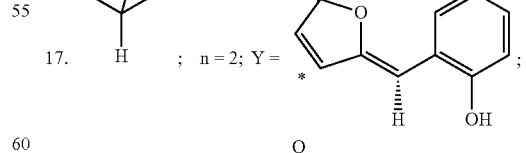;

18. $R^{1a} = R^{1b} = OH$; n = 2; Y = 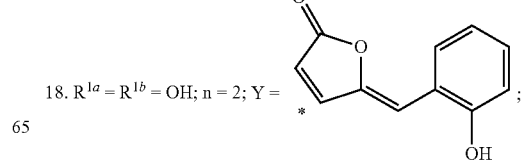;

-continued

19. $R^{1a} = R^{1b} = OH$; n = 2; Y = 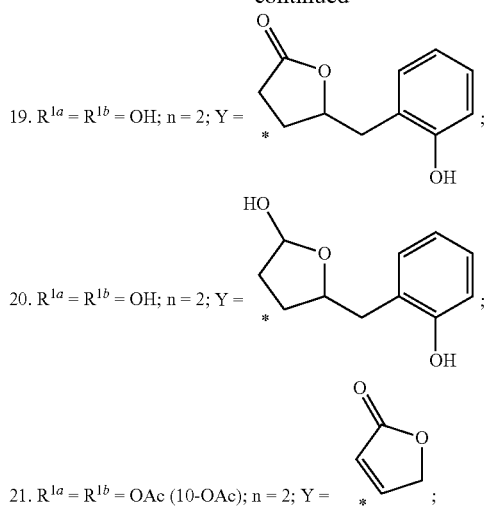

20. $R^{1a} = R^{1b} = OH$; n = 2; Y =

21. $R^{1a} = R^{1b} = OAc$ (10-OAc); n = 2; Y =

-continued

22. $Y = R^{1a} = R^{1b} = OAc$ (10-OAc); n = 2; $Y = CO_2H$;

23. $R^{1a} = R^{1b} = OH$; n = 2; $Y = CO_2H$;

24. $R^{1a} = R^{1b} = OH$; n = 2; $Y = CO_2Me$; or

25. $R^{1a} = R^{1b} = OH$; n = 2; $Y = CH_2OH$;

and *denotes the attachment point;

or a pharmaceutically acceptable salt, solvate or prodrug thereof;

and stereoisomers, isotopic variants and tautomers thereof.

16. The method of claim 1, wherein the arthritis is rheumatoid arthritis or collagen-induced arthritis (CIA).

17. The method according claim 9, wherein z is 1 or 2; and each $R^4$ is independently selected from F, Br, Cl, I, OH, Me, Et, $CF_3$, $OCF_3$, $CF_3$, $NMe_2$, OMe, OEt, $NO_2$, OPh, and SMe.

* * * * *

UNITED STATES PATENT AND TRADEMARK OFFICE
CERTIFICATE OF CORRECTION

PATENT NO. : 9,505,798 B2  
APPLICATION NO. : 13/989973  
DATED : November 29, 2016  
INVENTOR(S) : Dan R. Littman Page 1 of 1

It is certified that error appears in the above-identified patent and that said Letters Patent is hereby corrected as shown below:

In the Specification

In Column 1, beginning at Line 16 and ending at Line 20, please delete:

"The research leading to the present invention was funded in part by National Institutes of Health grants F32GM0860552, R01GM058833, R01GM067659, and ROIAI080885. The United States government has certain rights in the invention."

And insert:

--"This invention was made with government support under grants GM058833 and GM067659 awarded by the National Institutes of Health. The government has certain rights in the invention."--

Signed and Sealed this  
Eighth Day of May, 2018

Andrei Iancu  
*Director of the United States Patent and Trademark Office*